US010290070B2

(12) United States Patent
Gordon et al.

(10) Patent No.: US 10,290,070 B2
(45) Date of Patent: May 14, 2019

(54) SYSTEM AND METHOD FOR INTEGRATING DATA WITH GUIDELINES TO GENERATE DISPLAYS CONTAINING THE GUIDELINES AND DATA

(75) Inventors: Tim H. Gordon, River Vale, NJ (US); Janet Davidson, Eden Prairie, MN (US); Nancy A. Dunne, Ridgewood, NJ (US); Roger Mazze, Shorewood, MN (US); Rachel Robinson, Golden Valley, MN (US); Gregg Simonson, Bloomington, IN (US); Paul A. Upham, Edgewater, NJ (US); Todd Weaver, St. Paul, MN (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 166 days.

(21) Appl. No.: 12/232,907

(22) Filed: Sep. 25, 2008

(65) Prior Publication Data

US 2009/0099872 A1    Apr. 16, 2009

Related U.S. Application Data

(63) Continuation of application No. 09/985,173, filed on Nov. 1, 2001, now abandoned.

(51) Int. Cl.
*G16H 10/60* (2018.01)
*G06Q 50/22* (2018.01)
(Continued)

(52) U.S. Cl.
CPC ........... *G06Q 50/22* (2013.01); *G06F 16/972* (2019.01); *G06F 19/325* (2013.01);
(Continued)

(58) Field of Classification Search
CPC .............................. G06Q 50/24; G06Q 50/22
(Continued)

(56) References Cited

U.S. PATENT DOCUMENTS 5,574,828 A * 11/1996 Hayward et al. ............... 706/45
5,583,758 A    12/1996 McIlroy et al.
(Continued)

OTHER PUBLICATIONS

Gomez et al.: "A Telemedicine Distributed Decision-Support System for Diabetes Management" Proceedings of the Annual International Conference of the Engineering in Medicine and Biology Society, Paris, Oct. 29-Nov. 1, 1992, New York, IEEE, US, vol. 3 Conf. 14, Oct. 29, 1992 (Oct. 29, 1992), pp. 1238-1239.
(Continued)

*Primary Examiner* — Lena Najarian
(74) *Attorney, Agent, or Firm* — Dickinson Wright, PLLC

(57) ABSTRACT

A system and method for automatically integrating data with guidelines to generate displays containing the guidelines and data. The automated system and method can integrate patient data with treatment guidelines to assist a healthcare provider, such as a physician or the like, in providing treatment to the patient. The system and method employ a data storage component, adapted to store guideline data representing guidelines for assessing a condition of an entity, guidelines for taking action on the entity, or both, and to store feature data representing at least one feature of the entity. The system and method further employ an output device, adapted to output at least one diagram representing the guideline data, with the diagram including at least one component representing a relationship of at least a portion of the feature data to at least a portion of the guideline data.

34 Claims, 66 Drawing Sheets

(51) Int. Cl.
  *G06F 19/00*    (2018.01)
  *G06Q 50/24*    (2012.01)
  *G16H 15/00*    (2018.01)
  *G06F 16/958*   (2019.01)

(52) U.S. Cl.
  CPC ........ *G06F 19/326* (2013.01); *G06F 19/3418* (2013.01); *G06F 19/3481* (2013.01); *G06Q 50/24* (2013.01); *G16H 10/60* (2018.01); *G16H 15/00* (2018.01)

(58) Field of Classification Search
  USPC .......................................... 705/2, 3; 600/300
  See application file for complete search history.

(56)  References Cited

U.S. PATENT DOCUMENTS

| | | |
|---|---|---|
| 5,732,397 A | 3/1998 | DeTore et al. |
| 5,953,704 A | 9/1999 | McIlroy et al. |
| 5,974,124 A | 10/1999 | Schlueter et al. |
| 6,126,596 A | 10/2000 | Freedman |
| 6,230,142 B1 | 5/2001 | Benigno et al. |
| 2001/0050610 A1* | 12/2001 | Gelston ........................ 340/5.53 |
| 2002/0091687 A1* | 7/2002 | Eglington ........................ 707/5 |
| 2003/0178031 A1* | 9/2003 | Du Pen et al. ............... 128/898 |

OTHER PUBLICATIONS

Sonksen et al: "Information technology in diabetes care 'Diabeta': 23 years of development and use of a computer-based record for diabetes care" International Journal of Bio-Medical Computing, Elsevier Science Publishers, Shannon, IE, vol. 42, No. 1, Jul. 1, 1996 (Jul. 1, 1996), pp. 67-77.

Hunt et al.: "Patient-specific evidence-based care recommendations for diabetes mellitus: development and initial clinic experience with a computerized decision support system" International Journal of Medical Informatics, Elsevier Scientific Publishers, Shannon, IR, vol. 51, No. 2-3, Aug. 1998 (Aug. 1998), pp. 127-135.

Montani et al: "Protocol-based reasoning in diabetic patient management" International Journal of Medical Informatics, Elsevier Scientific Publishers, Shannon, IR, vol. 53, No. 1, Jan. 1999, pp. 61-77.

* cited by examiner

SELECT PATIENT

A - C [TOP OF PAGE]
D - F [TOP OF PAGE]

| DEE, SANDRA | | TYPE 2 SCREENING & DIAGNOSIS |

G - I [TOP OF PAGE]
J - L [TOP OF PAGE]
M - O [TOP OF PAGE]
P - R [TOP OF PAGE]
S - U [TOP OF PAGE]

| SWEET, DAVID | | TYPE 2 INSULIN STAGE 2 ADJUST |

V - X [TOP OF PAGE]
Y - Z [TOP OF PAGE]

SAMPLE FOOD PLAN

| MEAL | CHO | MEAT/SUB | ADDED FAT |
|---|---|---|---|
| BREAKFAST | 3-4 | 0-1 | 0-1 |
| SNACK | 1-2 | 0 | 0-1 |
| LUNCH | 3-4 | 2-3 | 1-2 |
| SNACK | 1-2 | 0 | 0-1 |
| DINNER | 3-4 | 2-3 | 1-2 |
| SNACK | 1-2 | 0 | 0-1 |

1 CHO = 1 CHOICE OR 15 gm CARBOHYDRATE: 60-90 CALORIES
1 MEAT/MEAT SUB = 1 OZ (28 gm) SERVING = 7 g PROTEIN; 5 g FAT; 50-100 CALORIES
1 ADDED FAT = 1 SERVING OR 5 g FAT: 45 CALORIES
VEGETABLES = 1-2 SERVINGS/DAY WITH EACH MEAL; NOT COUNTED IN PLAN

FIG. 8D

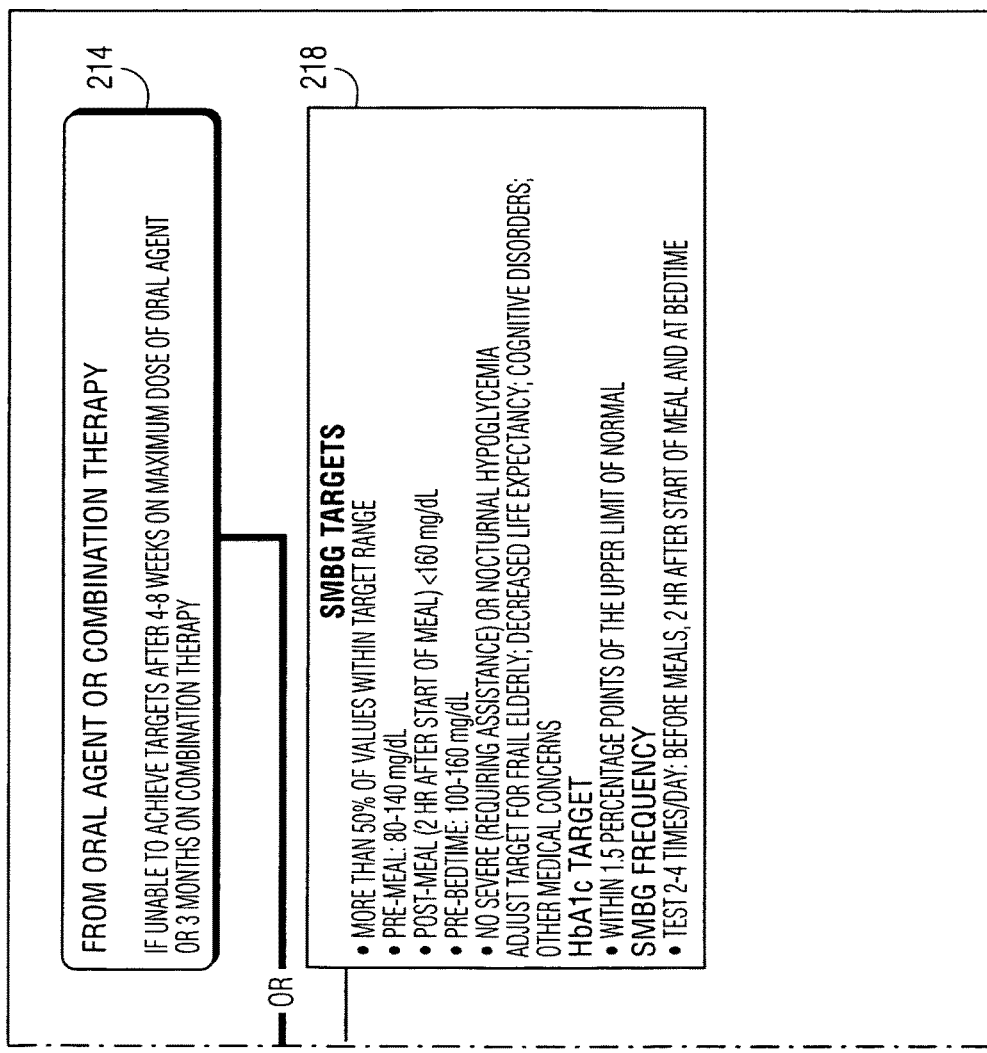

INSULIN STAGE 2 PATTERN ADJUSTMENTS
R/N - 0 - R/N - 0 OR LP/N - 0 - LP/N - 0

CLICK TO PRESCRIBE

| | CURRENT | PROPOSED | | <80 mg/dL | 140-250 mg/dL | >250 mg/dL |
|---|---|---|---|---|---|---|
| PM N | 3 | 3 | AM OR 3 AM | ▶ 0 | ▶ 0 | ▶ 0 |
| AM R OR LP | 4 | 4 | MIDDAY (MID) | ▶ 0 | ▶ 0 | ▶ 0 |
| AM N | 8 | 8 | PM | ▶ 0 | ▶ 0 | ▶ 0 |

| | TOTAL | TOTAL | | <100 mg/dL | 160-250 mg/dL | >250 mg/dL |
|---|---|---|---|---|---|---|
| PM R OR LP | 3 | 3 | BEDTIME (BT) | ▶ 0 | ▶ 0 | ▶ 0 |
| | 18 | 18 | | | | |

| CURRENT U/kg | PROPOSED U/kg |
|---|---|
| 0.3 | 0.3 |

FIG. 11D

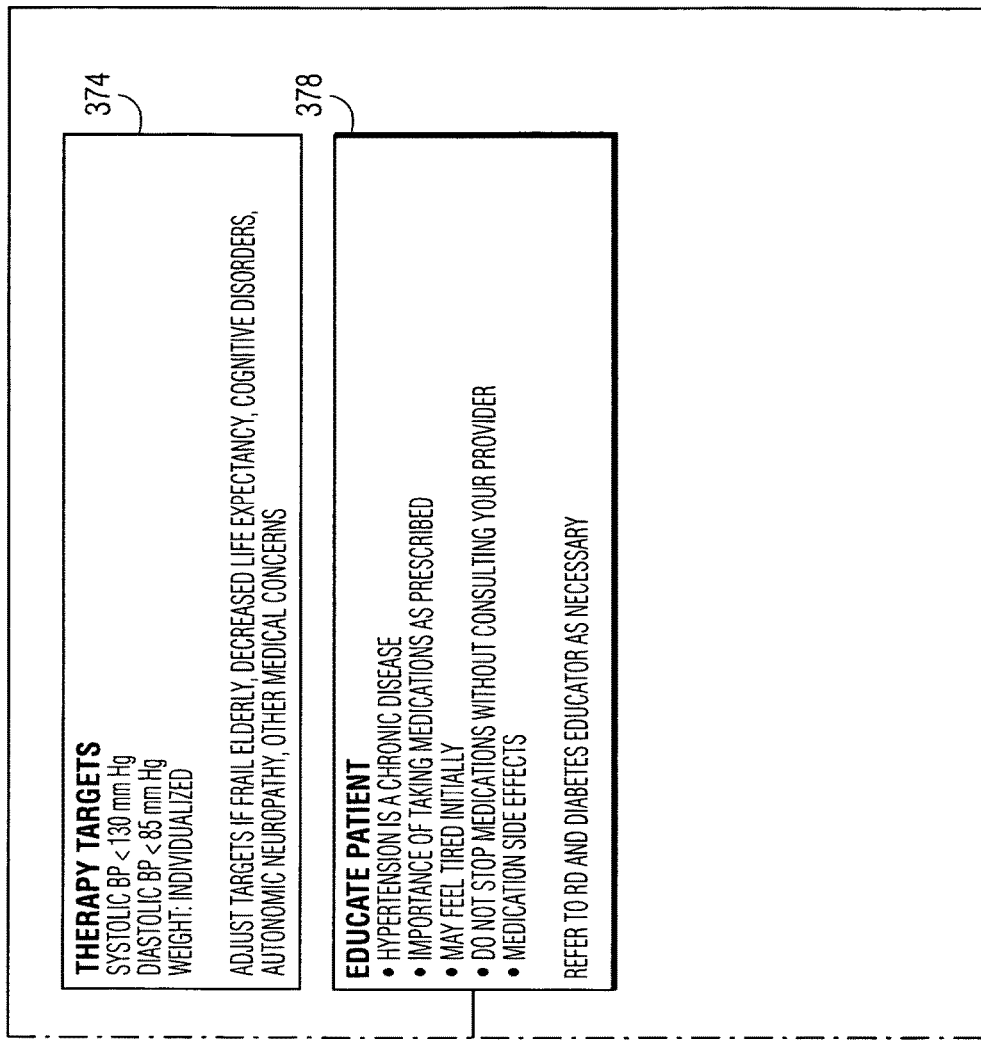

FIG. 22

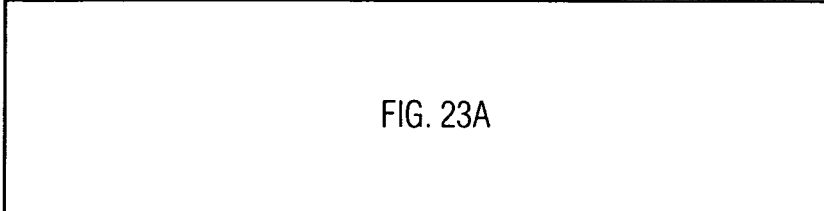
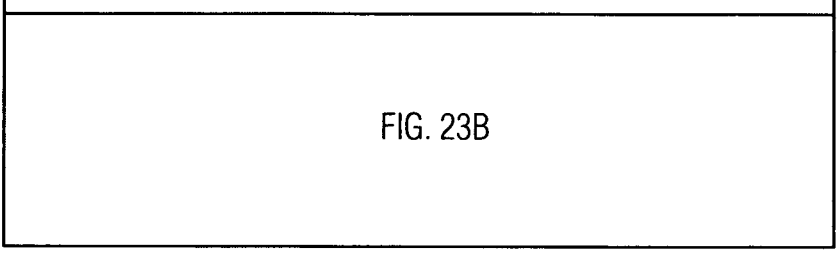
FIG. 23
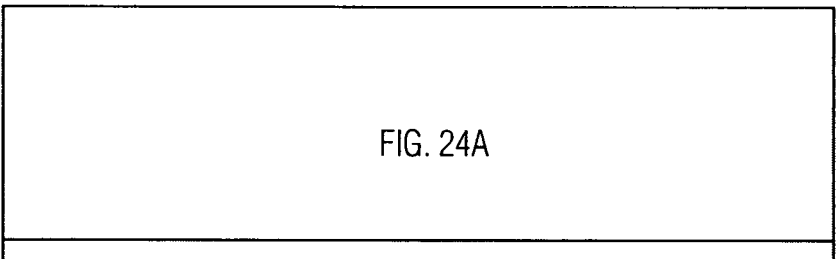
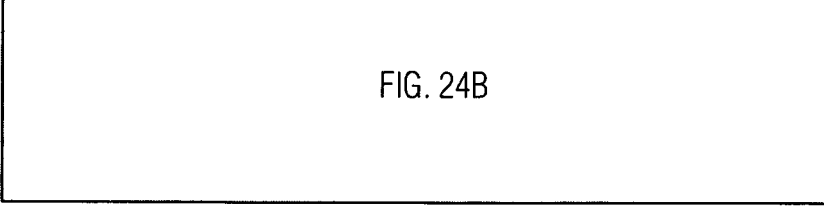
FIG. 24

FIG. 23A

BASIC INTAKE

INTAKE ▼

HEIGHT 5 ▼ FT 2 ▼ IN 157.48 CM
WEIGHT 135 LBS. 61.4 KGS
BMI 24.7

ALLERGIES

PRESENT MEDS:

ANTI-HYPERTENSIVES
- OTHER
- BENAZEPRIL
- CAPTOPRIL
- ENALAPRIL
- FOSINOPRIL
- LISINOPRIL

OTHER ANTI-HYPERTENSIVES

STATINS
- OTHER
- STATIN 1
- S 2
- S 3
- S 4
- S 5

133 →
- GLOBAL PATIENT DATA ☐
- OUTCOMES REPORTING ☐
- DATA ENTRY
- ORDERS & REFERRALS
- PATIENT DOCUMENTATION ☐
- SOAP
- SCREEN & DIAGNOSE ☐
- SELECT THERAPY ☐
- START FOOD PLAN / EXERCISE
- START ORAL AGENT
- START INSULIN
- START/MANAGE PUMP ☐
- ADJUST ORAL AGENT ☐
- ADJUST INSULIN ☐
- COMPLICATIONS
- EDUCATION
- PRINT
- HOME

Select DecisionPaths to Print

| UNDEFINED | |
|---|---|
| GLOBAL PATIENT DATA ☐ | TYPE 2   TYPE 1   GESTATIONAL   DIABETES MANAGEMENT ASSESSMENT   COMPLICATIONS |
| OUTCOMES REPORTING ☐ | |

[PRINT]

TYPE 2 DIABETES [TOP OF PAGE]

| DATA ENTRY | |
|---|---|
| ORDERS & REFERRALS ☐ | PRACTICE GUIDELINES ☐ |
| PATIENT DOCUMENTATION ☐ | SCREENING & DIAGNOSIS ☐   <AGE 18: SCREENING & DIAGNOSIS ☐ |
| SOAP ☐ | |

TYPE 2 DIABETES MASTER DECISION PATH

| SCREEN & DIAGNOSE ☐ | MASTER DECISION PATH ☐   <AGE 18: MASTER DECISION PATH ☐ |
|---|---|
| SELECT THERAPY ☐ | |

TYPE 2 DIABETES FOOD PLAN & EXERCISE

| START FOOD PLAN / EXERCISE ☐ | START ☐   ADJUST ☐ |
|---|---|

TYPE 2 DIABETES ORAL AGENTS

| START ORAL AGENT ☐ | ORAL AGENT SELECTION ☐ | |
|---|---|---|
| START INSULIN ☐ | ACARBOSE START ☐ | ACARBOSE ADJUST ☐ |
| START/MANAGE PUMP ☐ | METFORMIN START ☐ | METFORMIN ADJUST ☐ |
| | SULFONYLUREA START ☐ | SULFONYLUREA ADJUST ☐ |
| | THIAZOLIDINEDIONE START ☐ | THIAZOLIDINEDIONE ADJUST ☐ |

TYPE 2 DIABETES COMBINATION THERAPIES

| ADJUST ORAL AGENT ☐ | COMBINATION THERAPY SELECTION ☐ | |
|---|---|---|
| ADJUST INSULIN ☐ | COMBINATION ORAL AGENT START ☐ | COMBINATION ORAL AGENT ADJUST ☐ |
| COMPLICATIONS ☐ | SULFONYLUREA-INSULIN START ☐ | SULFONYLUREA-INSULIN ADJUST ☐ |
| EDUCATION ☐ | | |

INSULIN THERAPIES
   INSULIN ADJUSTMENT GUIDELINES ☐ ☐
      INSULIN STAGE 2 START ☐ ☐
      INSULIN STAGE 3A START ☐ ☐
      INSULIN STAGE 3A-MID START ☐ ☐
      INSULIN STAGE 4A START ☐ ☐

INSULIN STAGE 2 ADJUST ☐
      INSULIN STAGE 3A ADJUST ☐
      INSULIN STAGE 3A-MID ADJUST ☐
      INSULIN STAGE 4A ADJUST ☐

PRECONCEPTION AND PREGNANCY
   PRECONCEPTION PLANNING ☐     MANAGEMENT DURING PREGNANCY ☐

TYPE 1 DIABETES [TOP OF PAGE]

PRINT
HOME

FIG. 24B

Schedule

| APPT. | NAME | | | LAST VISIT |
|---|---|---|---|---|
| | HbA1c | BP | SMOKER? | LDL |
| 10:00 | WASHINGTON, MARTHA | | | |
| | 6.2 | 140/90 | NONE | 138 |
| 11:00 | PATTON, GEORGE | | | |
| | 7.6 | 130/80 | NO | 182 |
| 12:00 | LEE, ROBERT | | | |
| | 15.8 | 190/110 | NO | 74 |
| 13:00 | BRADLEY, OMAR | | | |
| | 6.1 | 32/38 | NO | 297 |
| 14:00 | BHATWADEKAR, DHURANDHAR | | | |
| | | | UNKNOWN | |
| 15:00 | SEAGULL, JONATHAN | | | |
| | | | NO | |
| 16:00 | RANA, PRATAP | | | |
| | | | NO | |
| 17:00 | RANA, JYOTI | | | |
| | | | UNKNOWN | |
| 18:00 | KILMER, JOYCE | | | |
| | | | NO | |
| 19:00 | MOYNIHAN, PAMELA | | | |
| | | | NO | |

FIG. 25

SYSTEM AND METHOD FOR INTEGRATING DATA WITH GUIDELINES TO GENERATE DISPLAYS CONTAINING THE GUIDELINES AND DATA

This is a continuation application of application Ser. No. 09/985,173, filed Nov. 1, 2001, the entire disclosure of which is hereby incorporated by reference. No new matter is introduced.

BACKGROUND OF THE INVENTION

Field of the Invention

The present invention relates to a system and method for automatically integrating data with guidelines to generate displays containing the guidelines and data. More particularly, the present invention relates to a system and method that employs a database that is capable of receiving data, such patient data, statistical data, and the like, from local or remote locations and integrating the data in a database along with guidelines, such as treatment guidelines used by medical providers, to generate displays containing the guidelines which are enhanced by the integrated data to provide information pertaining to the guidelines and recommendations for following the guidelines.

Description of the Related Art

As the population in the United States continues to increase, especially among the aging, the ability for traditional healthcare providers, such as hospitals and doctors' offices, to effectively provide treatment becomes increasingly challenging. In addition, as the average age of the population continues to increase, the number of people requiring care for long-term illnesses, such heart disease, diabetes and the like also increases.

Accordingly, alternatives to traditional health providers are being developed to accommodate these greater healthcare needs. Also, more effective and efficient systems are being developed to attempt to reduce the number of medical personnel necessary to treat or monitor patients. Specifically, systems are being developed that enable patients to have their conditions monitored at home, such as by themselves or a visiting nurse, and to provide data related to various tests, such blood pressure measurement, temperature, weight, blood glucose level, and the like, to a centralized database. These systems are then capable of organizing the data in an appropriate manner, and providing the data in an appropriate format to a healthcare provider, such a physician, who can review the data and determine whether the plan of care for the patient is sufficient or should be modified.

An example of a healthcare data manipulation and analysis system is described in U.S. Pat. No. 6,230,142 to Benigno, the entire content of which is incorporated herein by reference. According to the Benigno system, a healthcare provider, such as a nurse can obtain patient data during a visit with the patient at, for example, the patient's home. This patient data is entered into a database that compares the data to treatment guidelines for the particular patient's disease, and provides a recommended course of treatment for the patient. Other examples of this type of system are described in U.S. Pat. Nos. 5,953,074 and 5,583,758, both to McGilroy, the entire content of both of these patents being incorporated herein by reference.

Although the patents cited above describe systems which attempt to gather and analyze patient data and provide some recommended plan of treatment, these systems are not configured to outline different options of patient care. These systems also are not effective in illustrating to the care provider a comparison between other variations of care plans that could be followed based on variations in the patient data. Therefore, healthcare providers may find these types of systems insufficient because they provide only a specific result for the patient based on the specific patient test data, and not different options that could be provided to the patient were the test data to be different.

A technique known as Staged Diabetes Management (SDM) exists that uses diagrams or decision paths to illustrate to a healthcare provider different courses of treatment for a diabetes patient. An example of the staged diabetes management technique is described in a book by Roger S. Mazze, Ph.D. et al., *Staged Diabetes Management—A Systematic Approach* (International Diabetes Center, 2000), the entire content of which is incorporated herein by reference. The Staged Diabetes Management technique described in this book is intended to provide a systematic approach to diabetes care that can significantly reduce average glycosylated hemoglobin A1C, reduce overall lower extremity amputation, and reduce adverse fetal and prenatal outcomes associated with Type 1 diabetes and pregnancy. SDM provides a comprehensive program that offers scientifically based guidelines for the prevention, detection and treatment of diabetes and its complications, and has proven to enhance the quality of patient care when compared to standard treatment approaches for diabetes.

Specifically, the SDM technique uses diagrams referred to as decision paths that incorporate research findings in Type 1 diabetes, Type 2 diabetes, and diabetes in pregnancy, and translates them into techniques usable for clinical practice. Over the past decade, the program has been adapted successfully by more than 10,000 practitioners in 200 diabetes treatment centers worldwide.

Although the SDM technique has been very successful, it is somewhat difficult to implement in a practical sense because of the need to manually integrate patient data with the SDM guidelines. That is, when a healthcare provider uses the known SDM technique, the healthcare provider must manually compare the patient data, such as test measurements and the like, with the questions and criteria set forth in the decision paths. Based on this comparison, the healthcare provider manually determines the course of treatment to provide to the patient in view of the guidelines outlined in the decision path. Again, although this technique is successful in achieving the desired results, it may be somewhat difficult for a healthcare provider to use in a practical sense.

Accordingly, a need exists for a system and method capable of integrating patient data with SDM guidelines, to provide an overall improved SDM technique.

SUMMARY OF THE INVENTION

An object of the present invention is to provide a system and method for automatically integrating data with guidelines to generate displays containing the guidelines and data.

Another object of the present invention is to provide an automated system and method for integrating patient data with treatment guidelines to assist the healthcare provider, such as a physician or the like, in providing treatment to the patient.

A further object of the present invention is to provide a system and method that is capable of receiving data, such patient data, statistical data, and the like, from local or remote locations and integrating the data in a database along with guidelines, such as treatment guidelines used by medical providers, to generate displays containing the guidelines which are enhanced by the integrated data to provide information pertaining to the guidelines and recommendations for following the guidelines.

Another object of the present invention is to provide a system and method for automatically incorporating patient data with a staged disease management technique to provide integration between the patient data and the decision pathways for treatment to the healthcare provider.

These and other objects are substantially achieved by providing a system and method for integrating guidelines with data. The system and method each employ a data storage component, which is adapted to store guideline data representing guidelines for assessing a condition of an entity, guidelines for taking action on the entity, or both, and which is further adapted to store feature data representing at least one feature of the entity. The system and method further employ an output device, adapted to output a diagram representing the guideline data. The diagram includes at least one component representing a relationship of at least a portion of the feature data to at least a portion of the guideline data. Specifically, the output device includes a display which adapted to display the diagram, or a printer which is adapted to print the diagram. The entity can be a person, in which event the feature data can represent at least one physical condition of the person, and the guideline data can represent medical information.

BRIEF DESCRIPTION OF THE DRAWINGS

These and other objects, advantages and novel features of the invention will be more readily appreciated from the following detailed description of a preferred embodiment thereof when read in conjunction with the accompanying drawings, in which:

FIG. 5 illustrates an example of a display screen displayed by a workstations used in conjunction with the network shown in FIG. 1 that can be used to generate integrated patent data and guideline displays in accordance with an embodiment of the present invention;

FIG. 22 is an example of a diagnosis display that can be displayed on a display screen of a workstation employed in the network shown in FIG. 1 in accordance with an embodiment of the present invention;

FIG. 24 is an example of a print selection display that can be displayed on a display screen of a workstation employed in the network shown in FIG. 1 in accordance with an embodiment of the present invention;

FIG. 25 is another example of a display screen displayed by a workstations used in conjunction with the network shown in FIG. 1 that can be used to generate integrated patent data and guideline displays in accordance with another embodiment of the present invention.

DETAILED DESCRIPTION OF THE PREFERRED EMBODIMENTS

Figure 1:
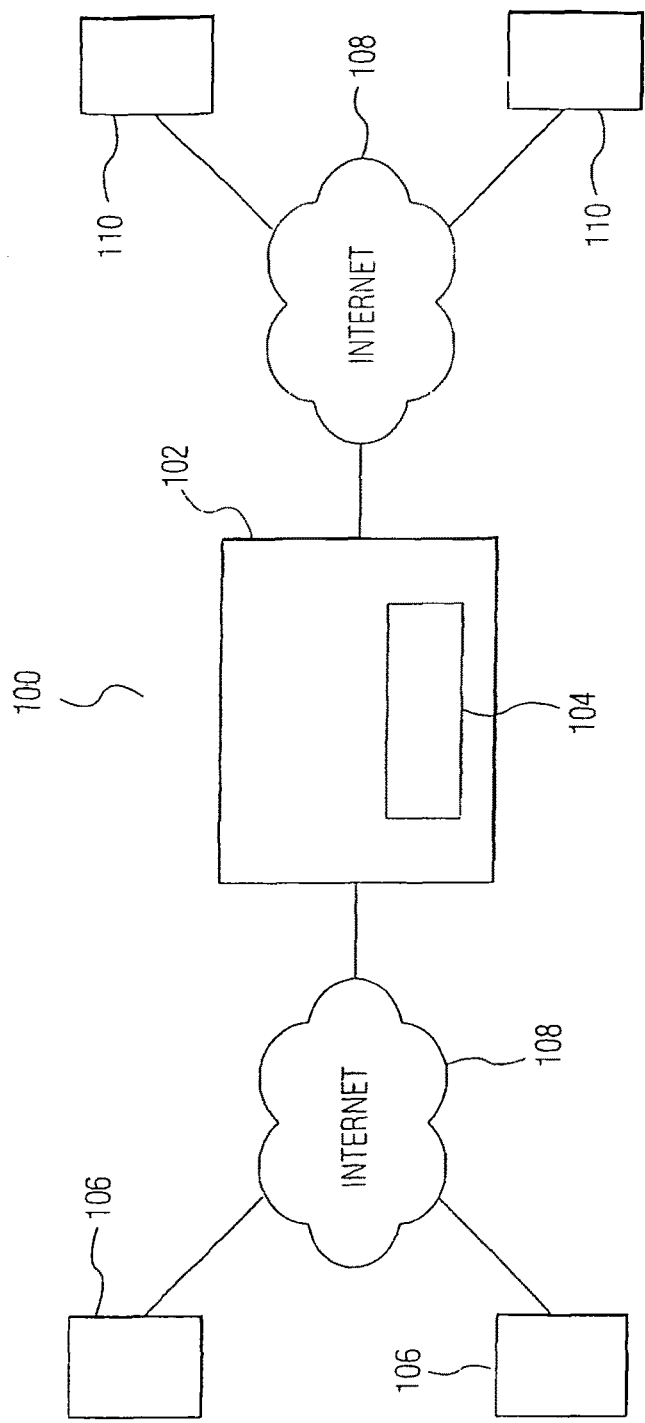
FIG. 1 is a conceptual block diagram illustrating an example of a network adapted for use with a system and method for integrating patient data with healthcare guidelines according an embodiment of the present invention.

FIG. 1 illustrates a network 100 employing a system and method for integrating data, such as patient data, with guidelines, such as healthcare guidelines, according to an embodiment of the present invention. The network 100 employs a centralized computer network 102 including a database 104 for storing information pertaining to patients as well as healthcare guidelines as discussed in more detail below. The network 100 further includes a plurality of workstations 106 which, in this example, are healthcare provider workstations. These workstations 106 can include desktop computer terminals or the like that are capable of accessing the centralized computer network 102 and database 104 via, for example, the Internet 108 or in any other suitable fashion.

The network 100 further includes a plurality of patient terminals 110 that can be used by, for example, the individual patients or a healthcare provider, such a home care nurse, to record and enter patient data, such as vital statistics, test results, and so on, into the centralized database 104. The patient terminals 110 can access the centralized database 104 via, for example the Internet 108 or in any other suitable manner in order to provide the data to the centralized database 104. The centralized database 104 is shown in more detail in FIG. 2.

Specifically, the database 104 is capable of receiving patient specific data entry sets 112 via the patient terminals 110 or by any other suitable method. That is, the patient can take his or her own vital signs and perform other self-administered tests, such as measuring blood glucose level and so on, and enter this information on-line via his or her patient terminal 110. Alternatively, this data can be obtained by a visiting nurse, technician or the like. Also, this data need not be entered via the patient terminal 110, but can be obtained manually and entered into the database 104 via another workstation at, for example, the facility in which the database 104 is present, or in any other suitable manner. Furthermore, instruments such as a sphygmomanometer, blood glucose measuring device, and so on, can be coupled to the patient terminal 110 to automatically input the patient's readings and measurements directly to the patient terminal 110 without the need for manual or electronic entry by the patient, nurse, and so on. The terminal 110 can then be used to provide this data to the database 104 in any of the manners described above.

It should be noted that the database 104 need not be configured as a centralized database to store the data discussed above, such as that pertaining to the guidelines and patient data. For example, the guideline data and patient data can be stored locally in the workstations 106 and patient terminals 110, respectively, and integrated as appropriate as discussed in more detail below. Furthermore, even if the guideline data and patient data are stored in separate databases or data storage locations, those separate databases or data storage locations can be referred to generally as a data storage component.

As further illustrated in FIG. 2 and as discussed in more detail below, the network 102 generates stage disease management pathways 114 that are integrated with the decision data sets 116 and reference content 118, which includes the patient-specific data, to generate clinical decision pathways 120. As also shown in FIG. 2 and discussed in more detail below, the database 104 can be controlled by the computer network 102 to generate educational material 122 and outcome reports 124 that take into account the patient-specific data.

Figure 2:
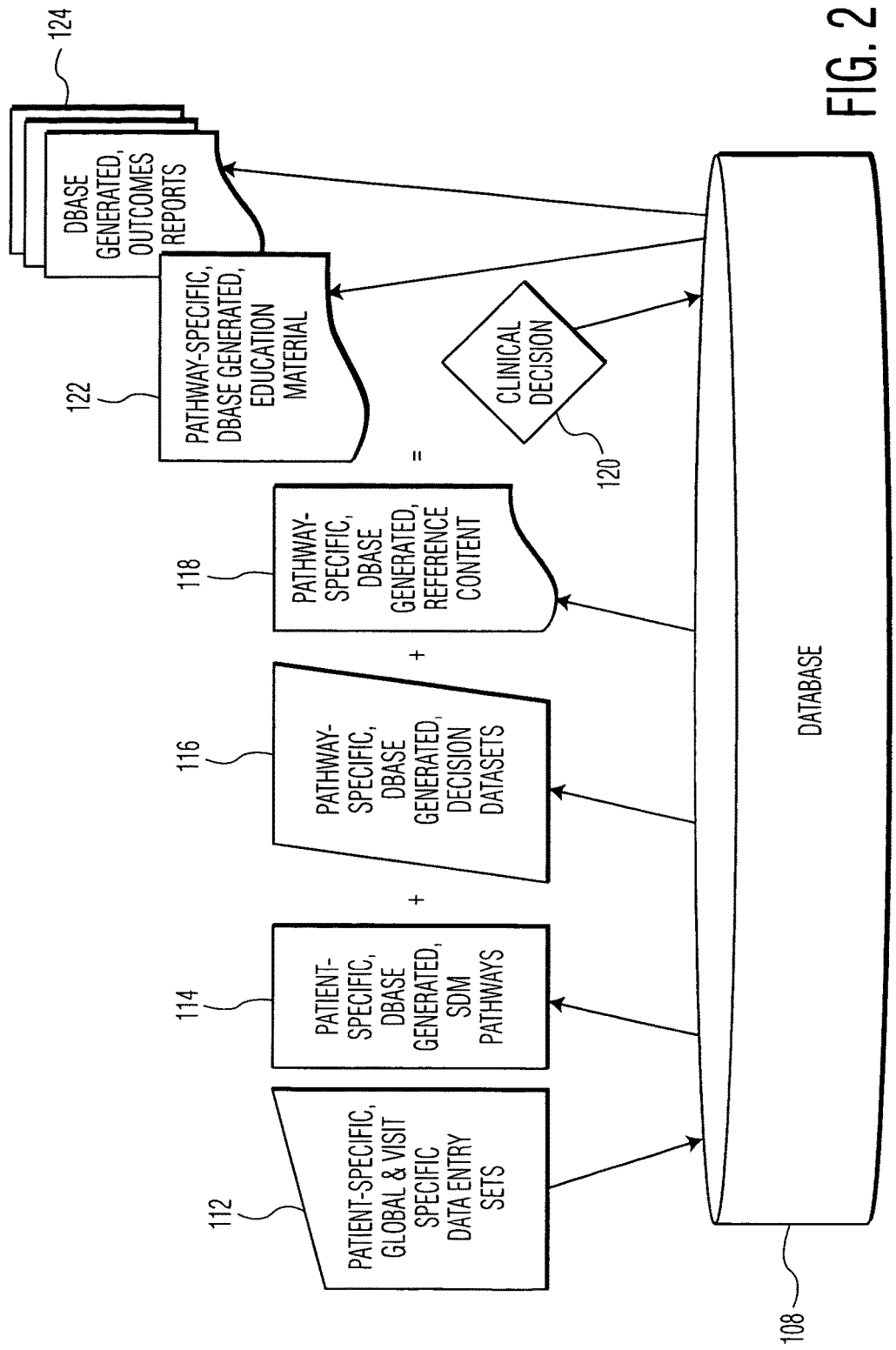
FIG. 2 is a conceptual block diagram illustrating an example of the manner in which data is input and output from a data base in a network shown in FIG. 1.
Figure 3:
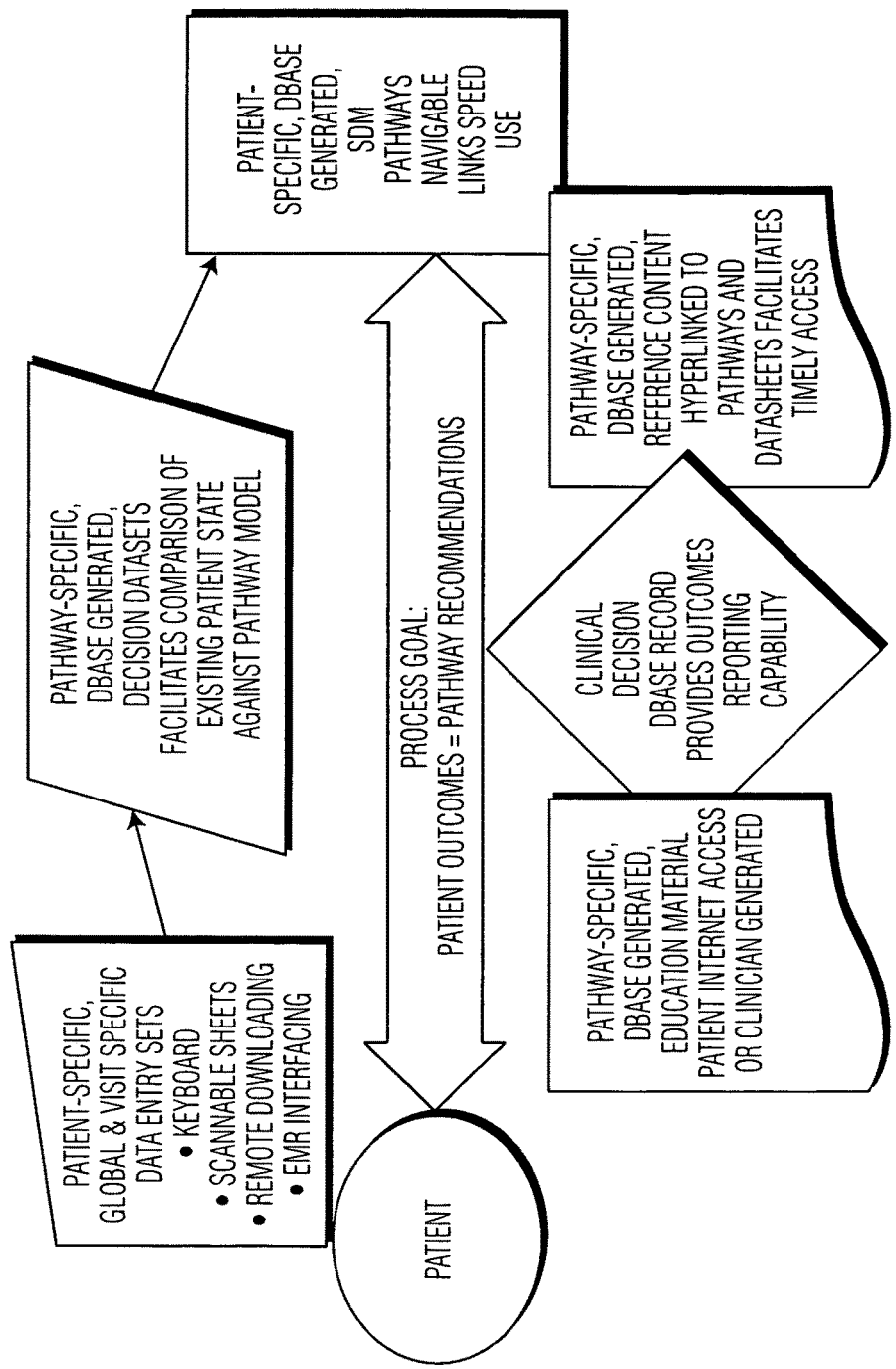
FIG. 3 is a conceptual diagram illustrating an example of the manner in which the network shown in FIG. 1 employing the system and method according to an embodiment of the present invention integrates patient data with treatment guidelines.
Figure 4:
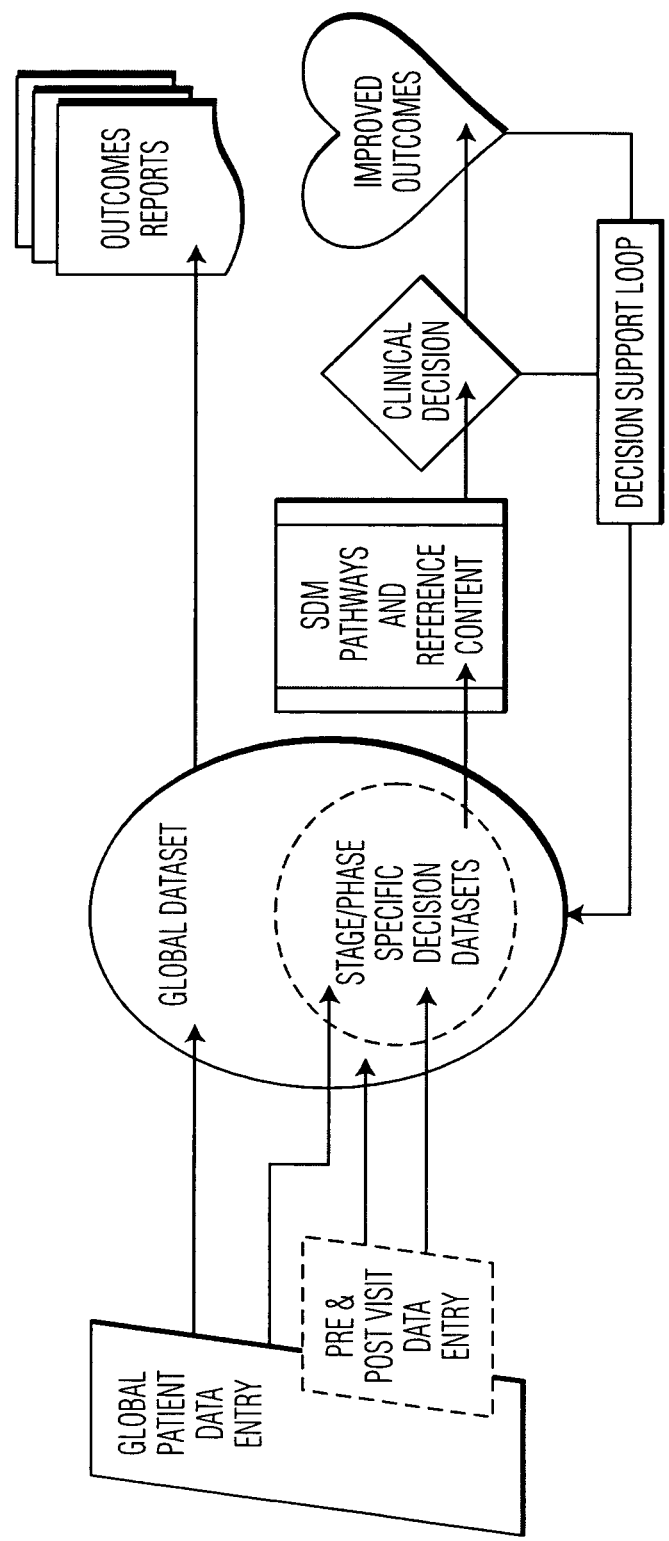
FIG. 4 is another conceptual diagram illustrating an example of the manner in which the network shown in FIG. 1 employing the system and method according to an embodiment of the present invention integrates patient data with treatment guidelines.

FIGS. 3 and 4 illustrate an example of the manner in which the operations involving the database 104, workstations 106 and patient terminals 110 shown in FIGS. 1 and 2 can address and eliminate the problems associated with conventional stage disease management techniques discussed in the Background section above. For example, the data entry sets can be provided by keyboard entry via the patient workstations 110. The data entry sets can also be provided to the database 104 via datasheets that are manually completed and scanned into electronic format, which is then forwarded to the database 104. The data entry sets can also be remotely downloaded to the database 104 in any fashion, and can also involve electronic medical records (EMR) interfacing to input the data to the database 104.

As further illustrated in FIGS. 3 and 4, the decision data sets facilitate comparison of the existing patient state against the pathway model as described in more detail below. The pathways are navigable links and are therefore easy to use by a healthcare provider. The reference content is hyperlinked to the pathways and data sheets to facilitate timely access by the healthcare provider. The clinical decision aspects of the database 104 provide outcomes reporting capability which can be used by healthcare providers, and the educational material aspects provide the patient with Internet access or clinician-generated materials to enable the patient to study information about his or her condition.

The manner in which an example of a system and method according to an embodiment of the present operates will now be described with reference to FIGS. 1, 2, and 5-24. Specifically, after the patient information has been entered into the database 104 in any of the manners described above, the network 102 can be controlled to generate treatment, pathways or guidelines that take into the account this particular patient's data to enable a healthcare provider to diagnose and prescribe treatment of the patient. When the healthcare provider accesses the database 104 via, for example, a healthcare provider workstation 106, the computer 102 can access the database 104 and provide data to the workstation 106 that enables the workstation 106 to generate a display 130 on its display screen as shown in FIG. 5. In this example, the guidelines and pathways generated relate to the diagnosis and treatment of diabetes. However, it can be appreciated that this type of system and method can be employed to provide treatment pathways and guidelines for any type of disease, or can have any other medical or non-medical application.

As shown in FIG. 5, the display 130 includes an alphabetic listing of patient names. In this example, only two names are shown, but the list can have as many names as the database 104 is capable of supporting.

Figure 6:
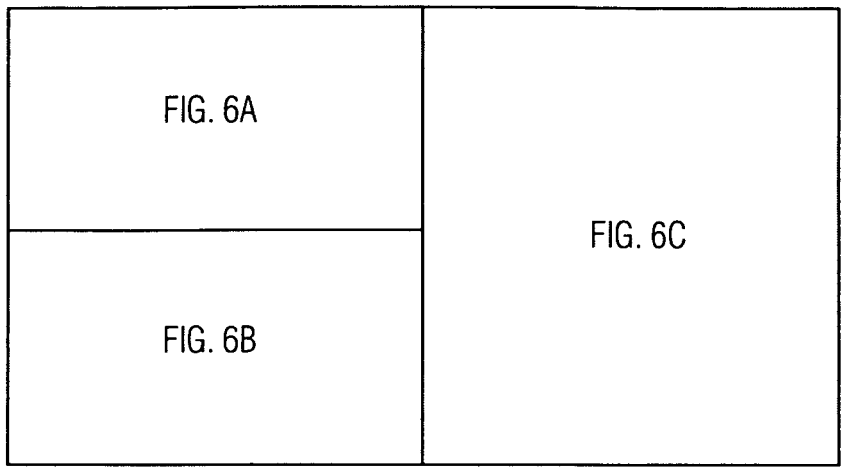
FIG. 6 illustrates an example of a screening and diagnosis display screen that can be generated on a workstation display in a network shown in FIG. 1 in accordance with an embodiment of the present invention.

If the healthcare provider is interested in using the system and method to obtain a diagnosis and treatment for the patient "Sandra Dee", the healthcare provider can use, for example, the mouse at his or her workstation 106 to click on the name "Sandra Dee." This action causes the web browser running on the workstations 106 to provide the necessary data to network 102, which results in the network 102 retrieving the appropriate data from database 104 and providing that data back to the web browser on the workstation 110. As illustrated in FIG. 6, this data causes the workstation 110 to generate a display 132 illustrating a screening and diagnosis pathway for the patient "Sandra Dee." This pathway is referred to as a diagram, which includes the type of pictorial display as illustrated.

In this example, the display 132 includes a button column 133 that enables the healthcare provider to generate various displays as discussed in more detail below. For example, the healthcare provider can click on the button entitled "Screening & Diagnosis Data" to display various boxes or components that show different guidelines that enable a healthcare provider to determine, based on the data entered into database 104 pertaining to "Sandra Dee", whether or not the patient "Sandra Dee" has any form of diabetes. For example, box 134 displays the types of risk factors for diabetes, along with the symptoms being experienced by the patient "Sandra Dee" and the capillary blood glucose (BG) readings that would indicate that the patient is suffering from a form of diabetes. It is noted that in box 134, the risk factors that the patient "Sandra Dee" meets are included. For example, the risk factors pertaining to dyslipidemia, ethnicity and family history are included. Also, symptoms such a blurred vision, UTI, dry/itchy skin, and so on are included. Furthermore, the results of the fasting blood glucose test as being greater than 100 mg/dL is highlighted.

As further illustrated in FIG. 6, box 136 highlights to the healthcare provider that the test performed was a fasting plasma glucose (FPG) reading, as opposed to a casual plasma glucose (CPG) reading. Box 138 highlights to the healthcare provider those diagnostic tests that were performed on the patient to indicate that the patient may have a form of diabetes.

Boxes 140, 142 and 144 similarly illustrate the different pathways that the diagnoses can take depending on the results of the patient's test. For example, box 144 indicates that the FPG of the patient was determined to be 149 on Oct. 10, 2000, and thus, this portion of box 144 is highlighted. Since box 144 is highlighted, the healthcare provider can then follow the path to box 146 to see the readings of the patient pertaining to the urine ketone. It is noted that box 146 indicates that the results of the urine ketone test were negative on Oct. 11, 2000. The healthcare provider is therefore instructed to box 148 to repeat the FPG test in seven days. The healthcare provider is not instructed to proceed to box 150 to provide a diagnosis for Type 1 diabetes.

As further illustrated in FIG. 6, box 151 of the pathway indicates to the healthcare provider that the FPG testing of the patient was 160 mg/dL on Oct. 11, 2000, which is greater than the guideline of 126 mg/dL. The pathway therefore indicates in box 152 that the healthcare provider should diagnose the patient with Type 2 diabetes. It is also noted that because the FPG level was greater than the guideline set forth in box 150, the healthcare provider is not instructed to proceed to box 154 to diagnose the patient with impaired glucose homeostasis. Also, because the patient's FPG level falls within the guidelines set forth in box 144, the pathway instructed the healthcare provider to proceed along the boxes subsequent to box 144. The healthcare provider is not instructed to proceed to box 141 which instructs the healthcare provider to diagnose the patient as having no diabetes.

Figure 7:
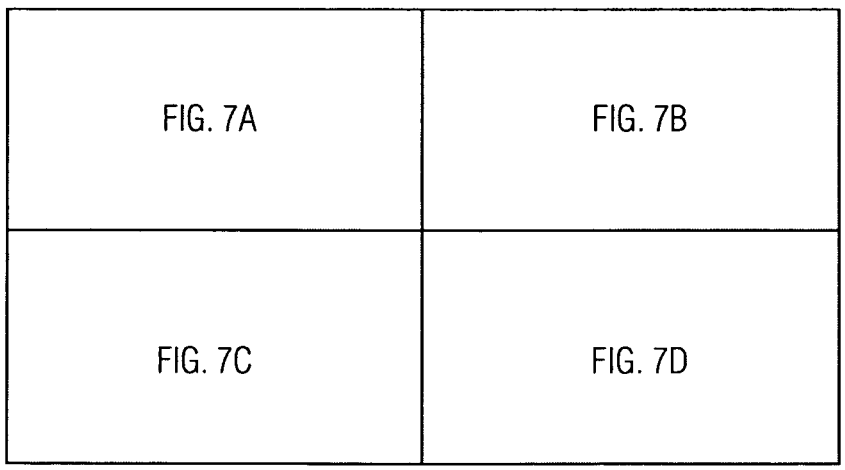
FIG. 7 illustrates a master decision path display screen that can be generated on a workstation display screen employed in the network shown in FIG. 1 in accordance with an embodiment of the present invention.
Figure 6A:
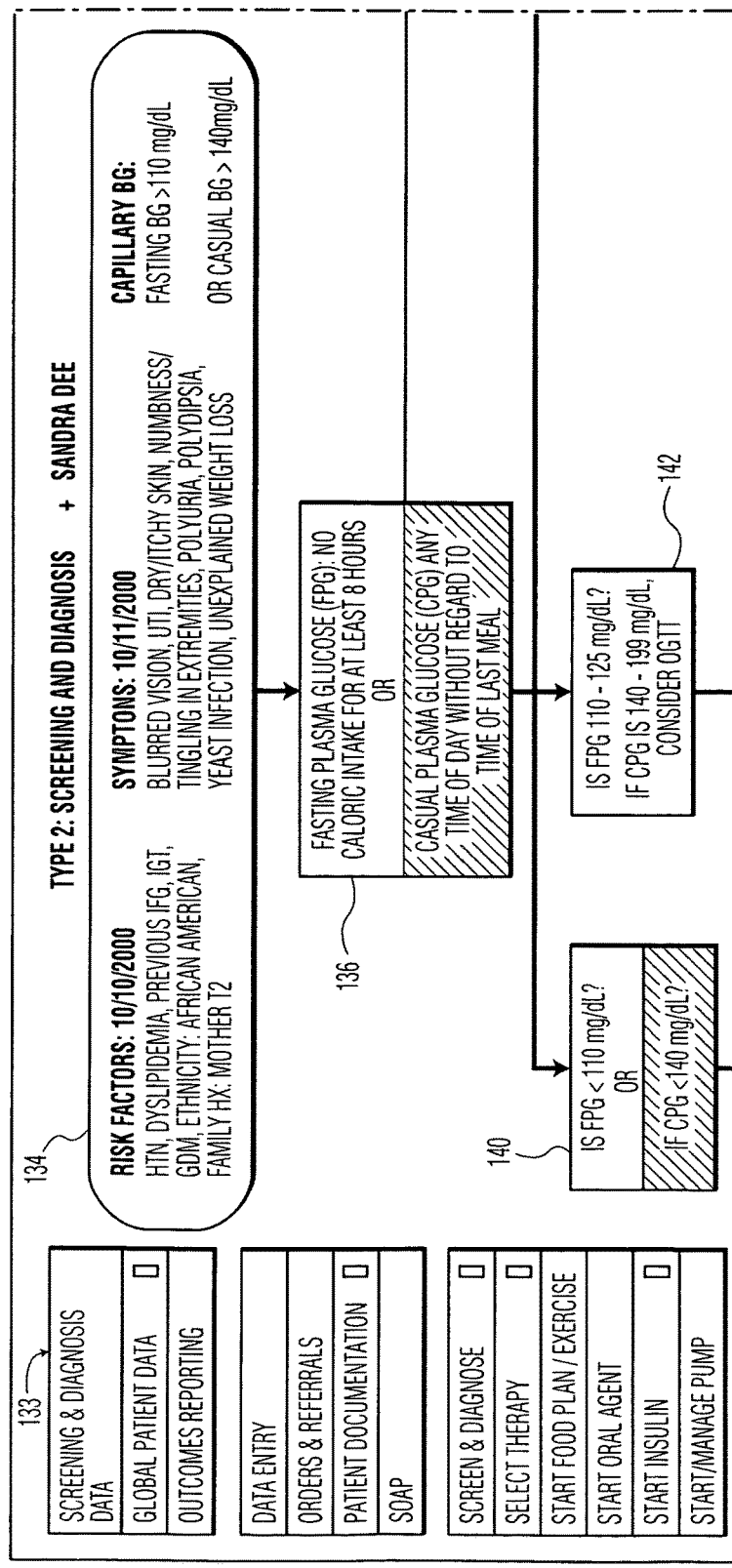
Figure 6B:
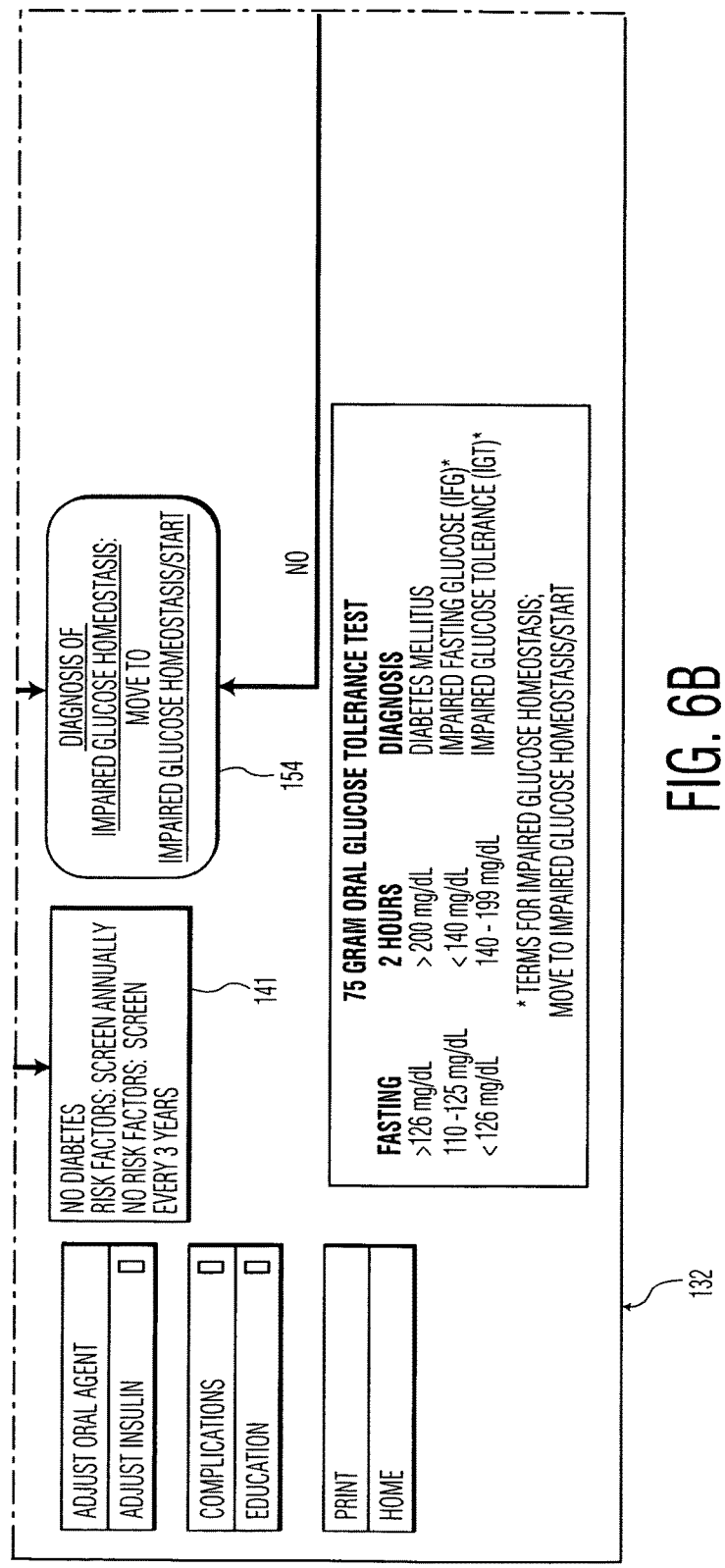
Figure 6C:
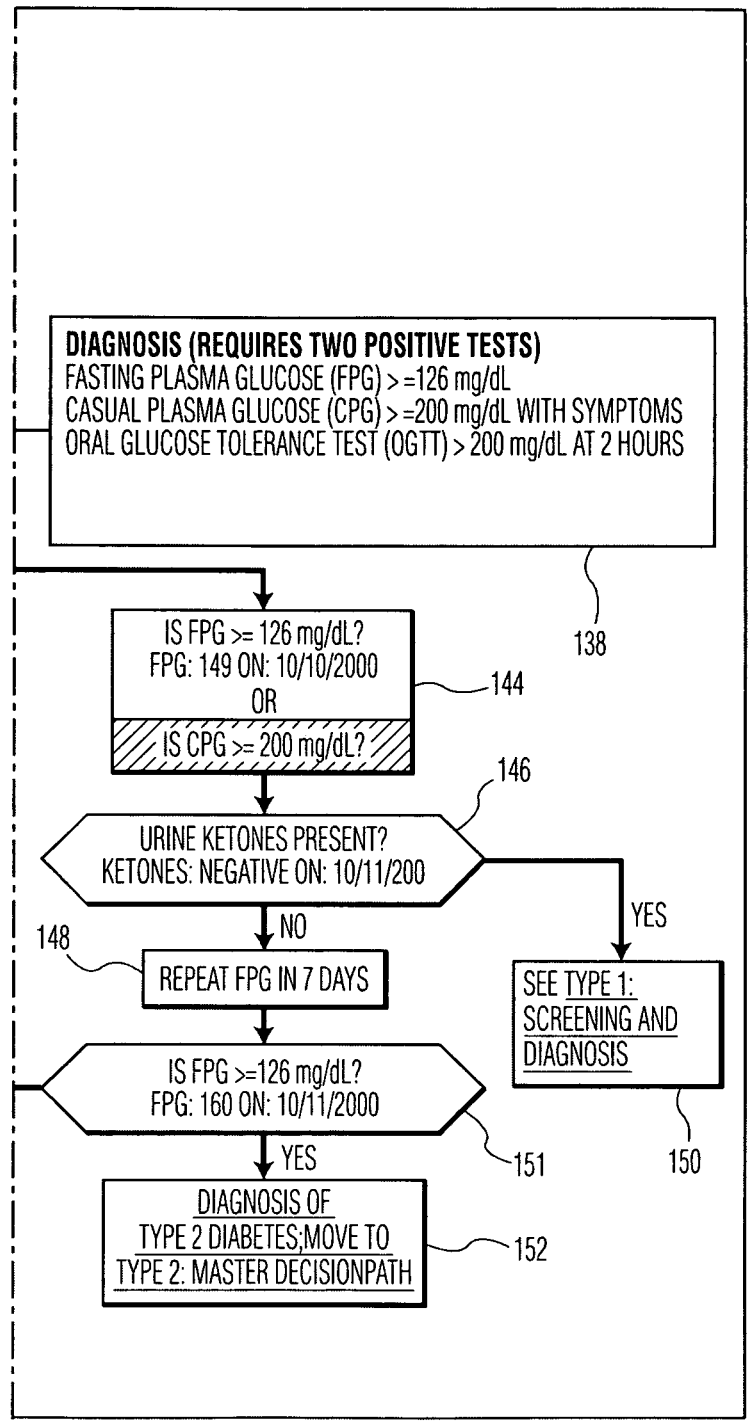
Figure 7A:
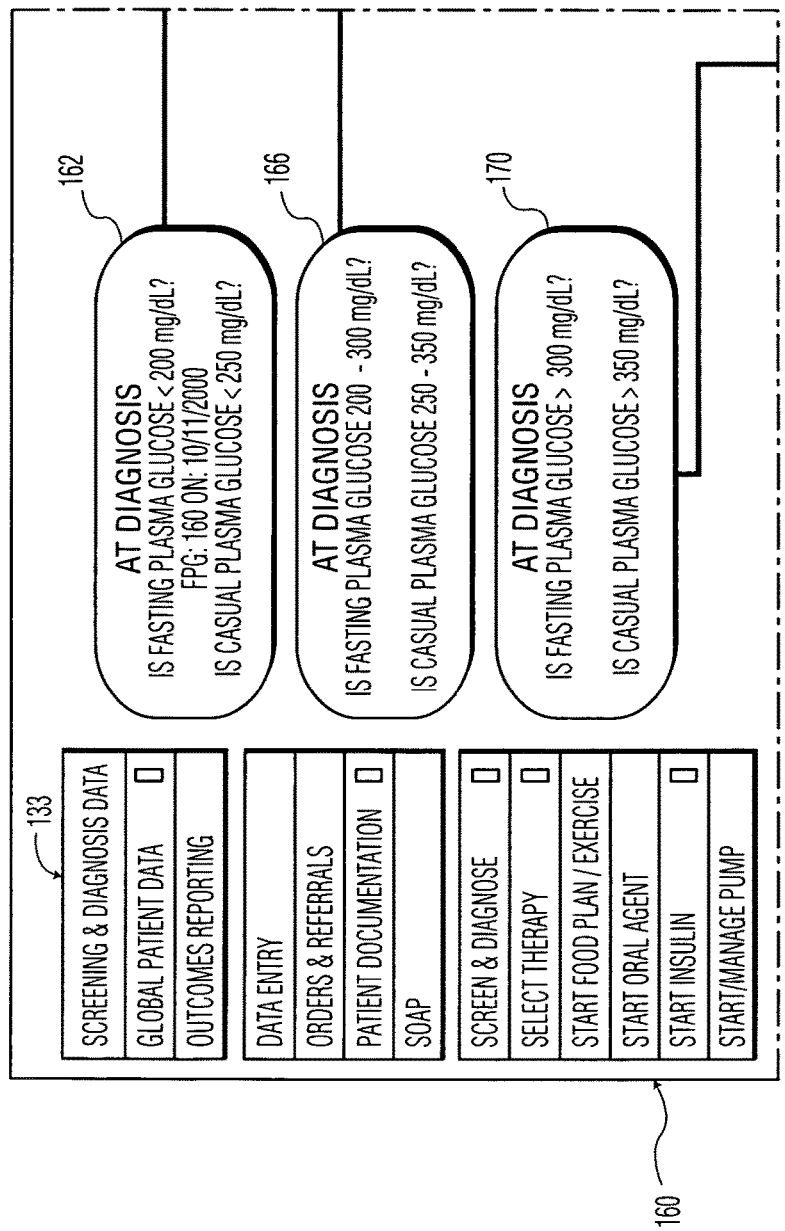
Figure 7B:
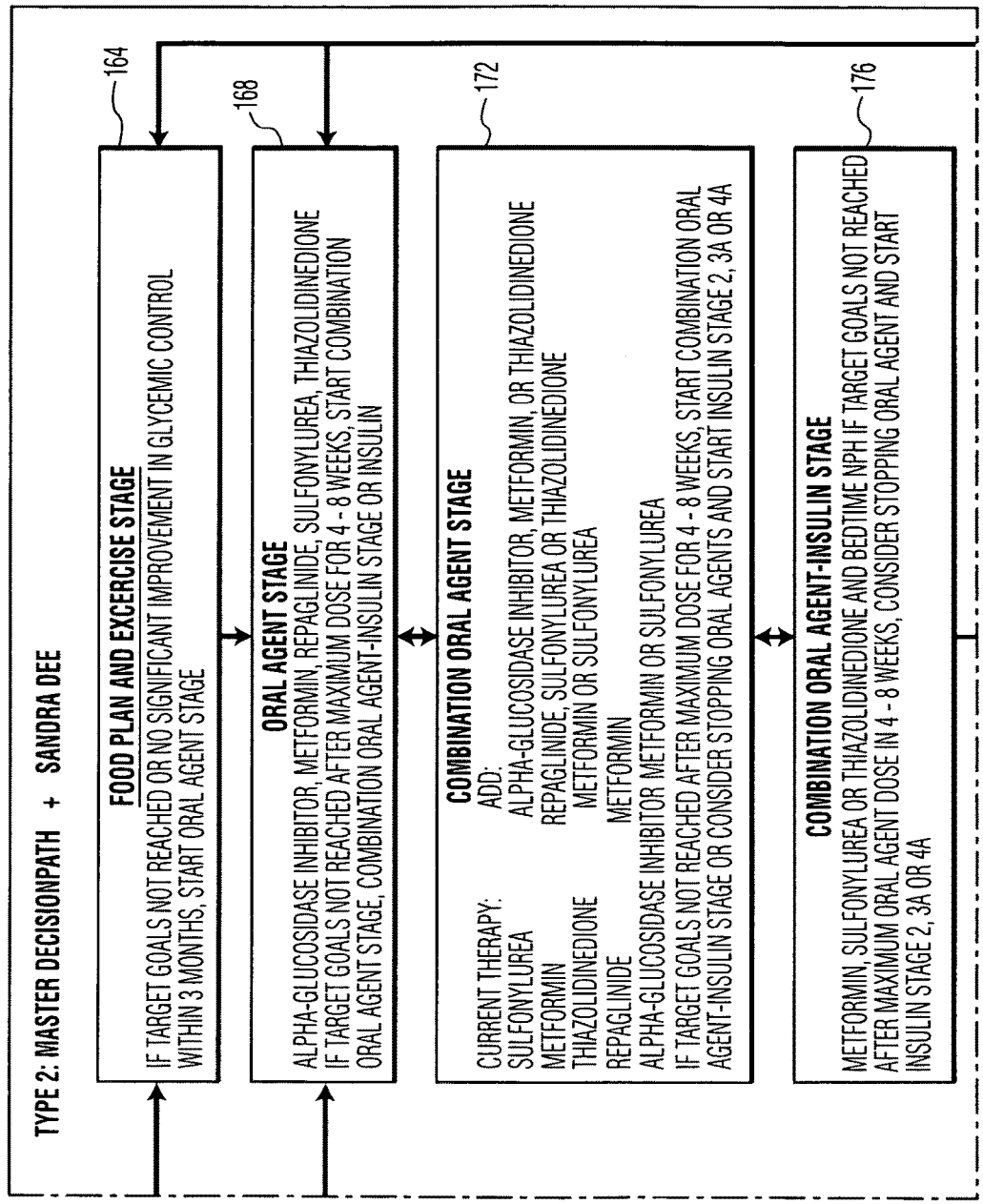
Figure 7C:
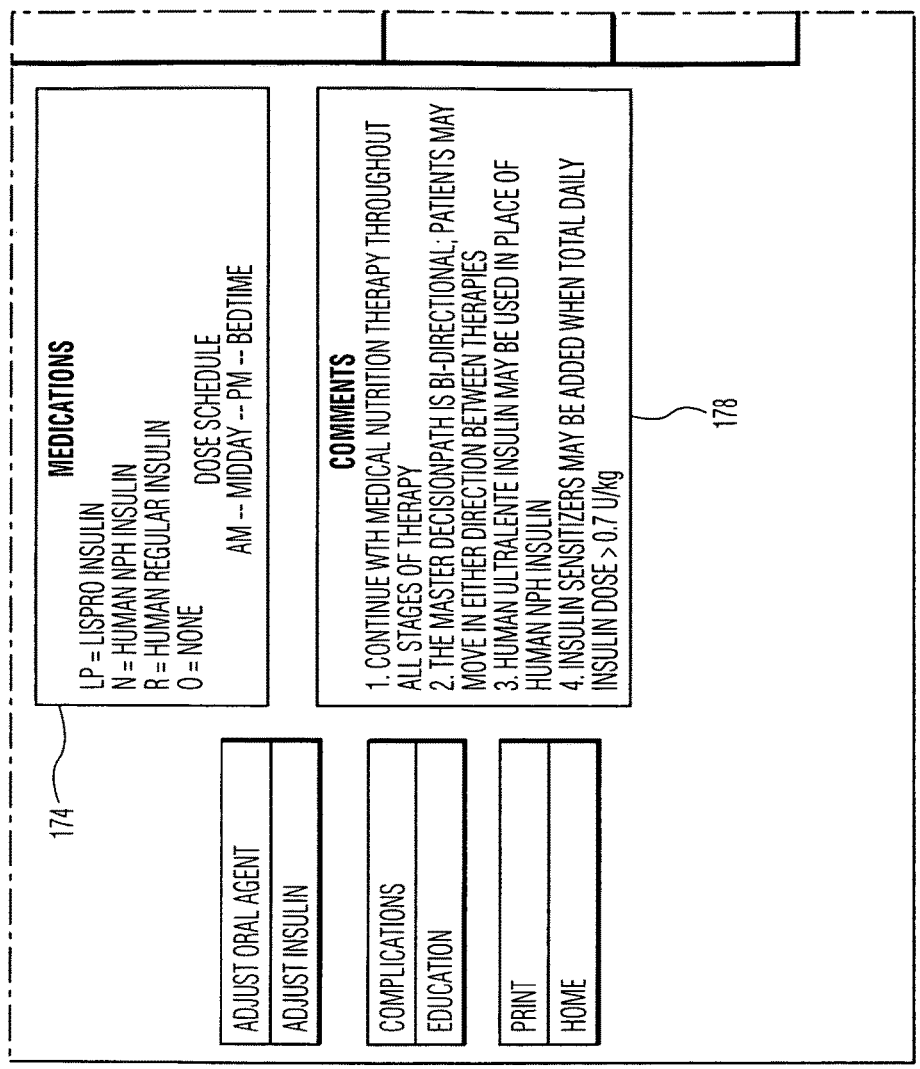
Figure 7D:
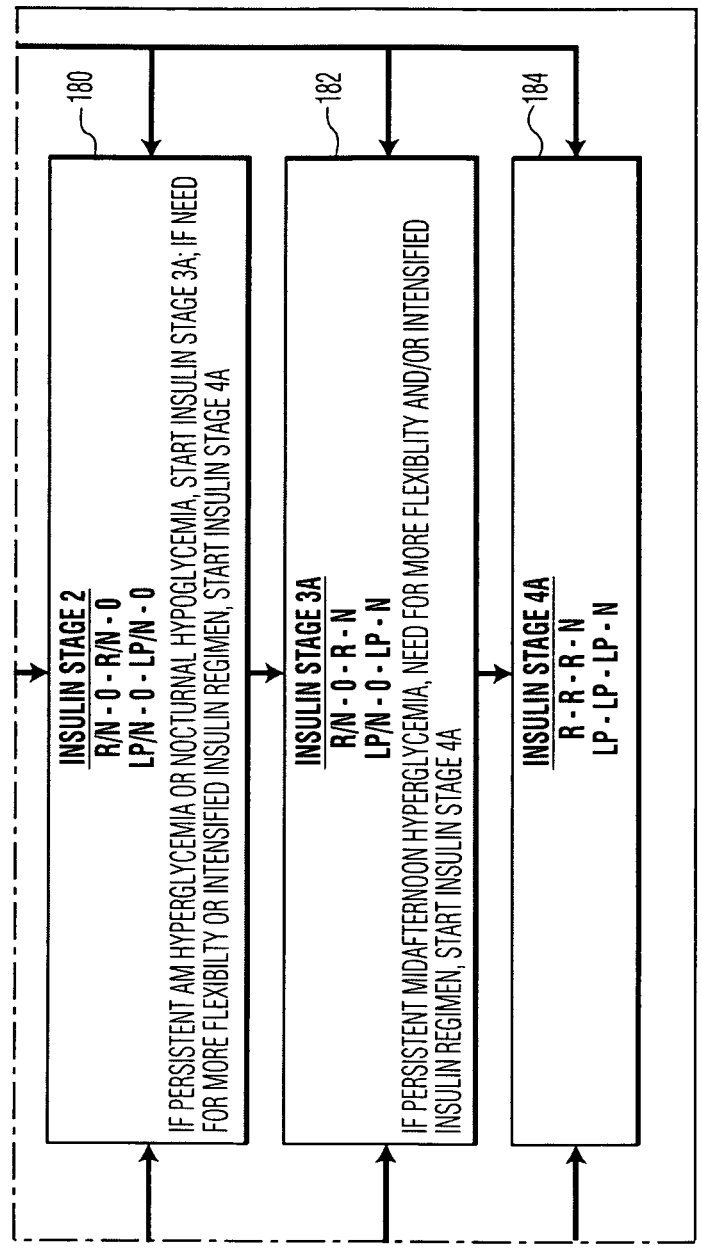

In box 152, the healthcare provider is instructed to generate a master decision path for the patient. By using the mouse on his or her workstation 110 to click on the term "Type 2 master decision path", the web browser sends data to the network 102 which, in response, retrieves the appropriate data from database 104 and provides that data to the web browser at workstation 110. The workstation 110 thus displays a display screen 160 as shown in FIG. 7. The boxes in the display screen 160 provide the healthcare provider with various types of recommendation for diet, exercise, and medication. For example, box 162 outlines a criteria for the FPG being less than 200 mg/dL. Because the FPG of the patient is indicated as being 160 mg/dL on Oct. 11, 2000, box 162 indicates to the healthcare provider to proceed to box 164 where the healthcare provider is instructed to prescribe a food plan and exercise for the patient. By clicking on the term "food plan and exercise stage" in box 164, the healthcare provider can control the web browser to provide an instruction to the network 102 to retrieve the appropriate data from database 104. The network 102 provides this data to workstation 110, which causes the web browser to display a display 186 as shown in FIG. 8.

Figure 8:
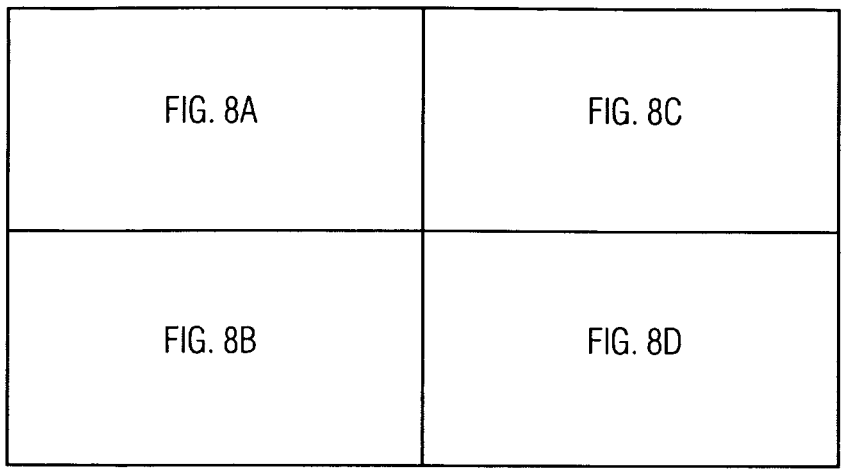
FIG. 8 is an example of a food plan and exercise start display that can be displayed on a display screen of a workstation employed in the network shown in FIG. 1 in accordance with an embodiment of the present invention.
Figure 9:
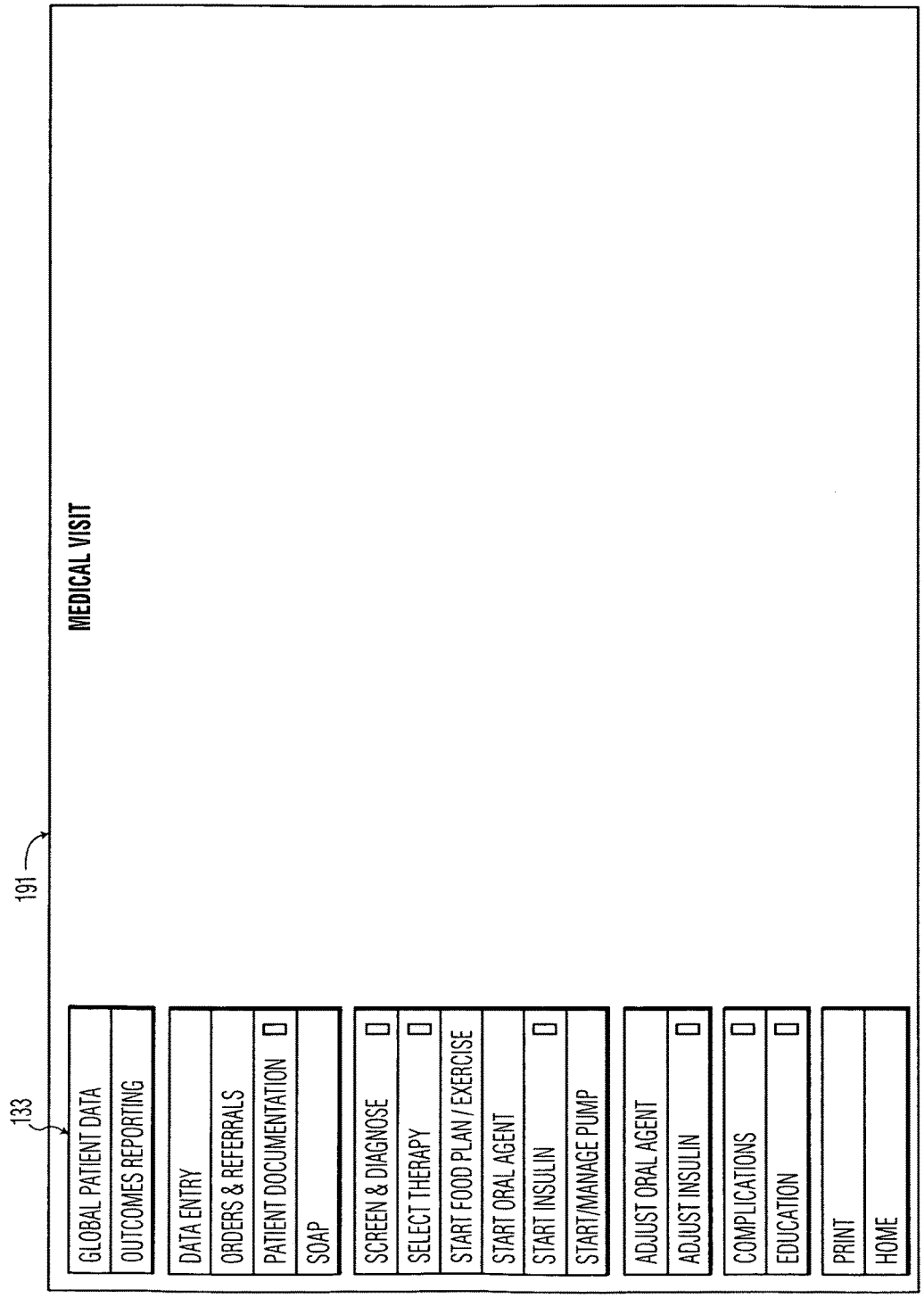
FIG. 9 is an example of a medical visit information display that can be displayed on a display screen of a workstation employed in the network shown in FIG. 1 in accordance with an embodiment of the present invention.
Figure 10A:
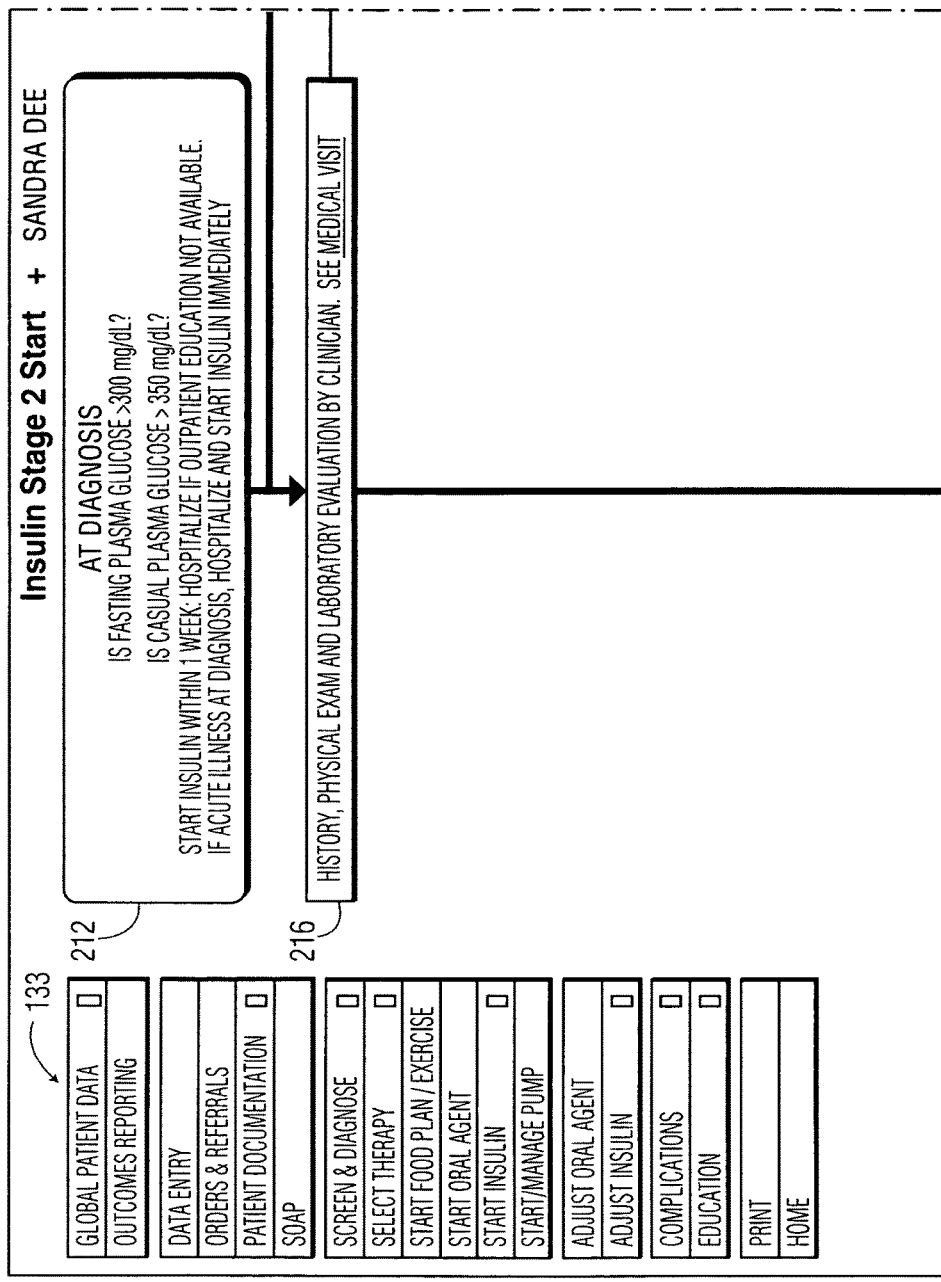
Figure 10B:
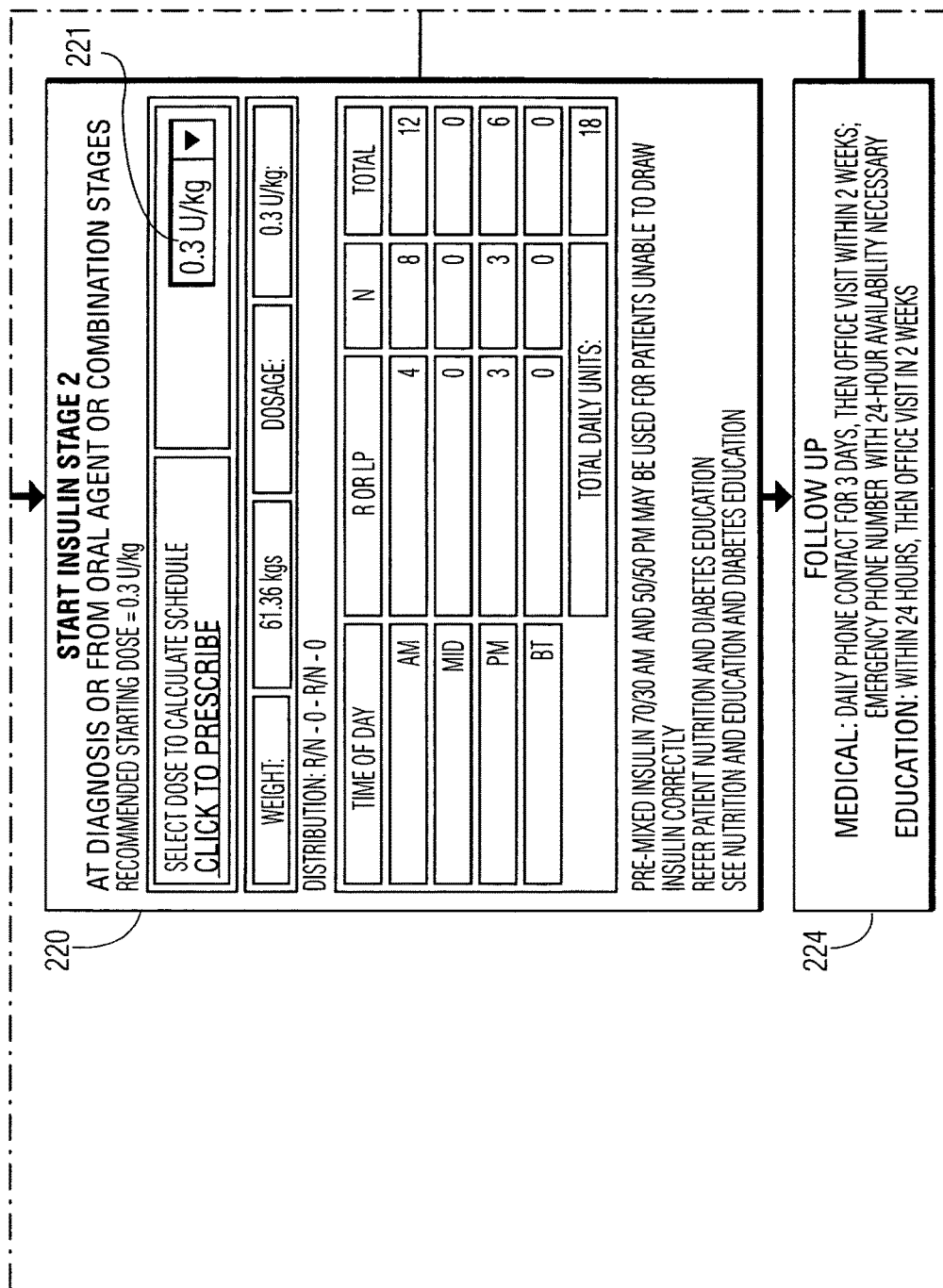
Figure 10D:
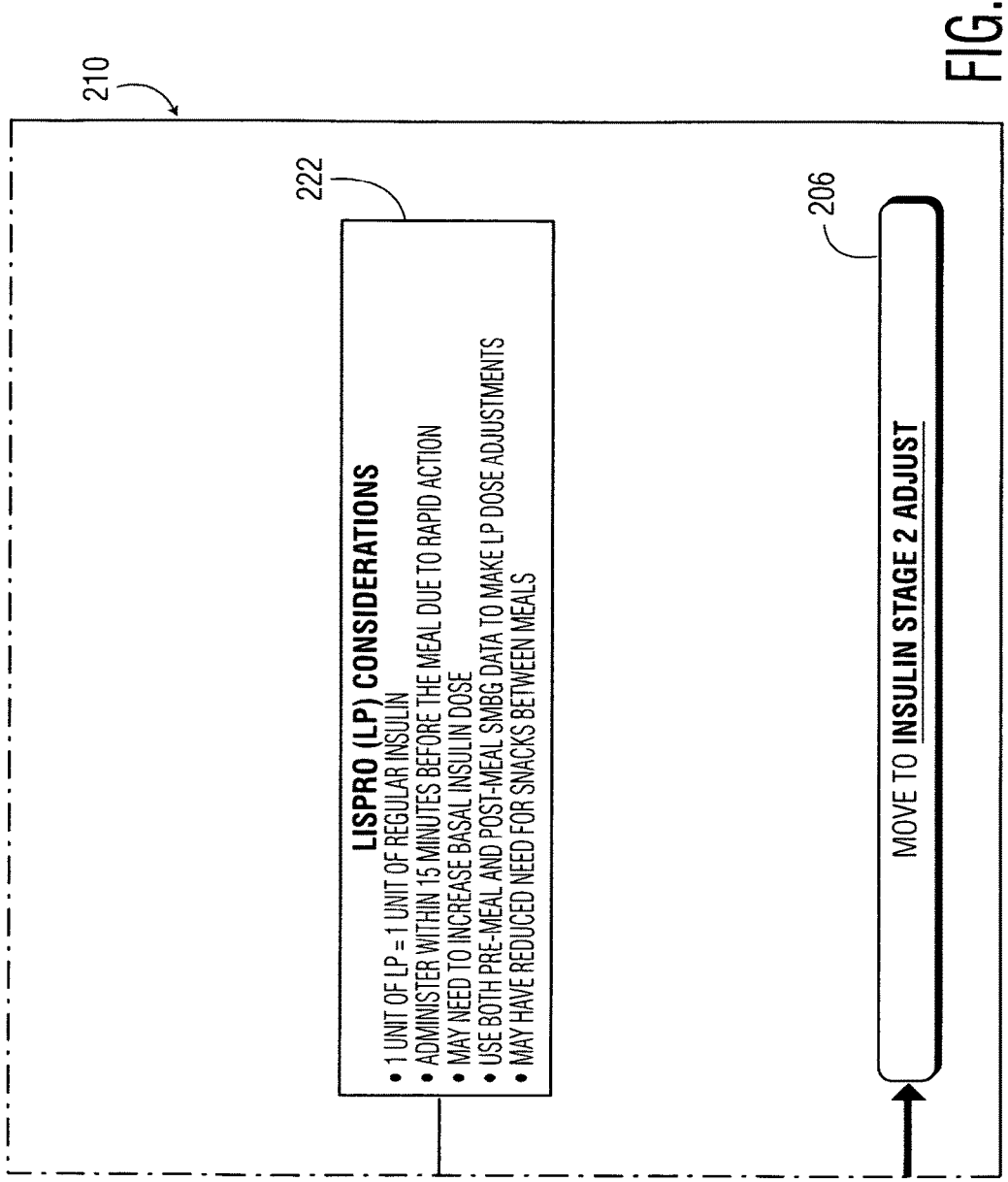

As further shown in FIG. 8, the display 186 includes boxes 188 through 204, which indicate to the healthcare provider recommendations for diet and exercise. For example, the diagnosis box 188 proceeds to box 190 which indicates to the healthcare provider that the records of the patient's medical visit should be reviewed. The healthcare provider can review the medical visit records by clicking on the medical visit term in box 190 to cause the web browser on the workstation 110 to display the medical visit display screen 191 as shown in FIG. 9, into which information pertaining to the patient's medical visit or visits can be entered. As further shown in FIG. 8, box 192 provides information to the healthcare provider for obtaining a registered dietician, while box 194 provides SMBG targets for the patient at different stages throughout the day.

Box 196 which follows box 190 also provides information for diet and exercise for the patient, while box 198 provides medical nutrition therapy guidelines. Box 200 indicates to the healthcare provider the periods of time in which the patient's medical condition should be reviewed and when the patient's recommended diet should also be reviewed. Box 202 provides a sample food plan that can be prescribed to the patient. Box 204, which follows box 200, allows the healthcare provider to adjust the food plan and exercise that was prescribed to the patient if deemed necessary after performing the follow-ups recommended in box 200.

Returning now to FIG. 7, it is noted that diagnosis boxes 166 and 170 are displayed to the healthcare provider at workstation 110 to enable the healthcare provider to determine whether the patient has reached the oral agent stage or the insulin stages. For example, if the patient FPG is within the guidelines as recommended in box 166, then the pathway indicates in box 168 that the healthcare provider should prescribe oral agents to the patient for treatment of his or her diabetes. Box 172 indicates a combination of oral agents that can be prescribed to the patient. In addition, box 170 indicates guidelines for FPG which would lead to the healthcare provider prescribing insulin for treatment of the patient. That is, box 176 indicates the recommendation and guidelines for prescribing a combination of oral agent and insulin to the patient. Boxes 180-184 provide recommendations for different doses of insulin depending on the stage of the patient's diabetes. Boxes 174 and 178 display types of medications that are typically prescribed, and also provide comments to the healthcare provider.

Figure 10:
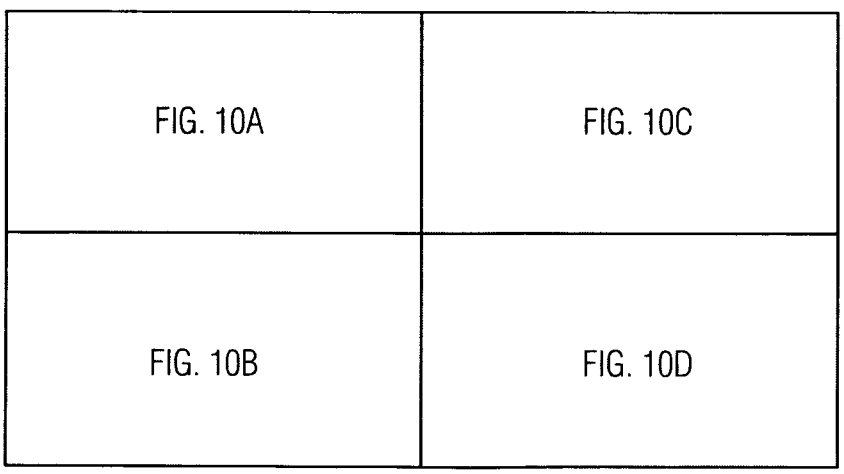
FIG. 10 illustrates an example of an insulin stage 2 start display that can be generated on a workstation display screen employed in the network shown in FIG. 1 in accordance with an embodiment of the present invention.
Figure 8A:
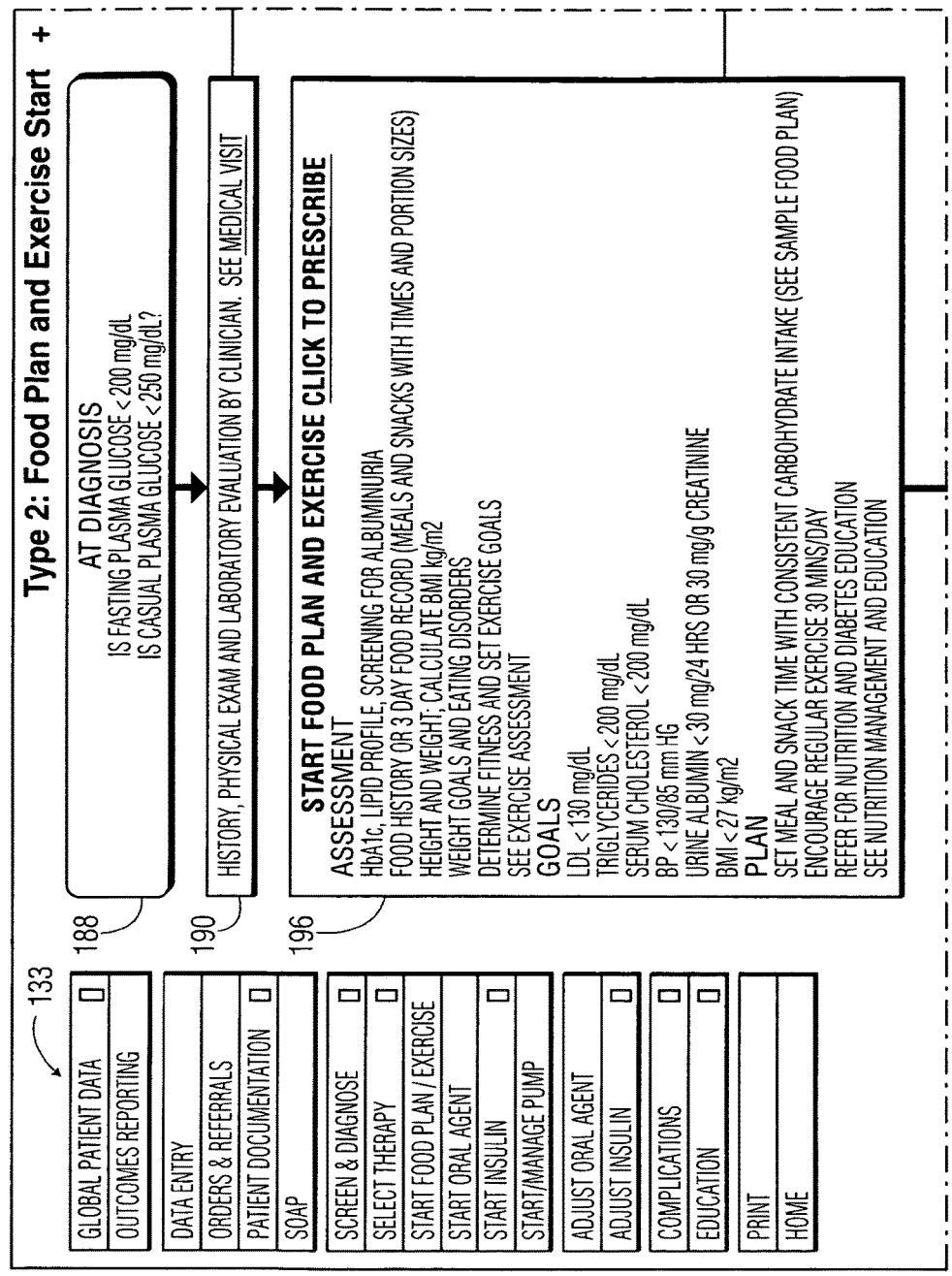
Figure 8B:
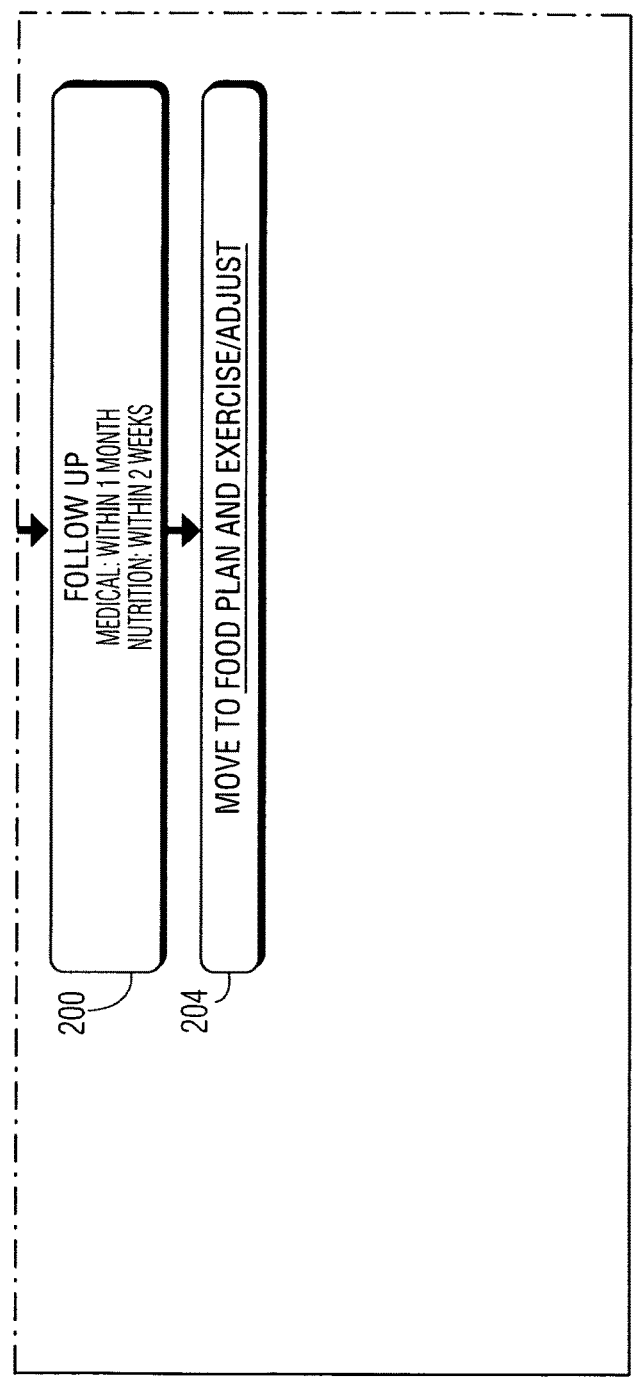
Figure 8C:
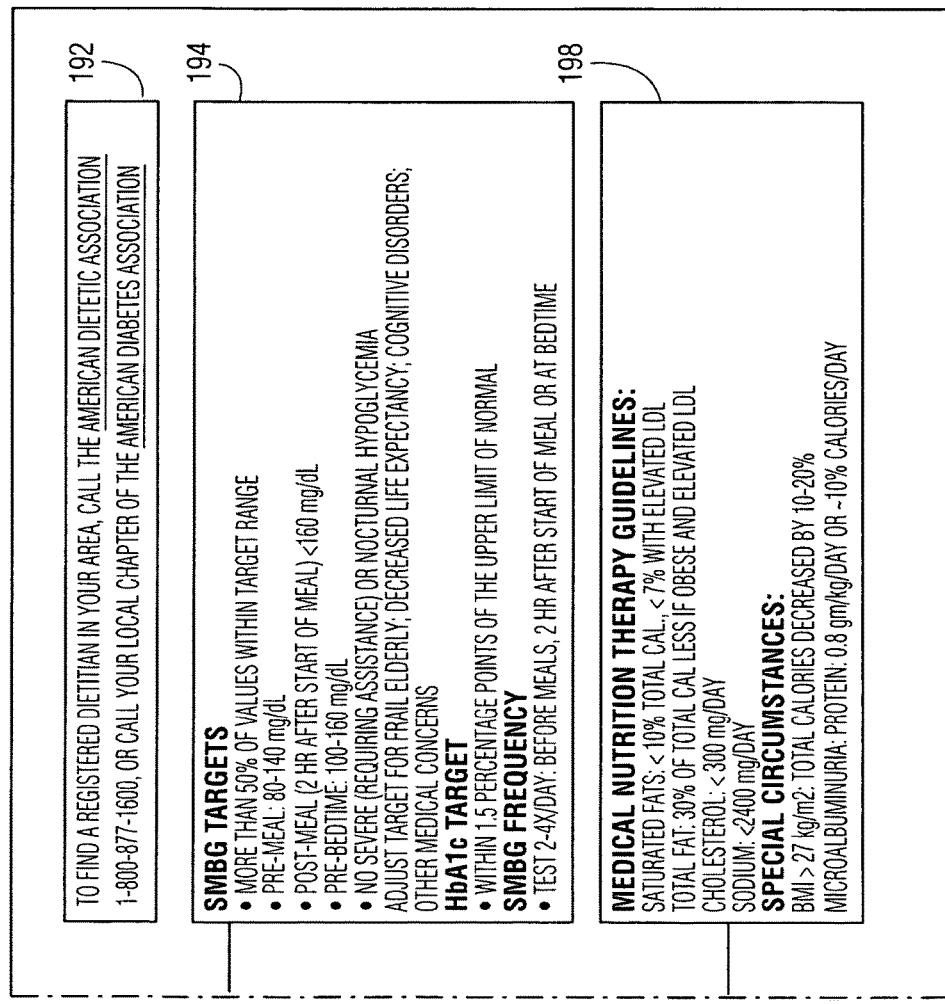

Based on the recommendations box 170, if the healthcare provider determines that the patient has reached insulin stage 2 indicated in box 180, the healthcare provider can click on the term "insulin stage 2" in box 180 to-display insulin stage 2 start screen as shown in FIG. 10. Insulin stage 2 start screen 210 includes boxes 212 through 226 which provides guidelines and recommendations for prescribing insulin to the patient. For example, box 212 sets forth guidelines concerning the patient's FPG at diagnosis, while box 214 sets forth guidelines for a patient who is undergoing oral agent or combination therapy. If these conditions in boxes 212 and 214 are met, the pathway in box 216 recommends to the healthcare provider that the patient's medical history be examined. The healthcare provider can achieve this by clicking on the medical visit term in box 216 to cause the web browser of workstation 110 to display the medical visit display screen as shown in FIG. 9.

The display screen 210 shown in FIG. 10 also gives SMBG targets in box 218 to assist the healthcare in making the diagnosis. Box 220, which follows box 216, provides a dose calculator to enable the healthcare provider to prescribe a recommended amount insulin based the patient's weight. That is, box 220 displays the patient's weight (i.e., 61.36 kgs) and the recommended dosage (i.e., 0.3 U/kg) for that weight. Box 221 also displays the recommended dosage, while the remainder of box 220 breaks down that recommended dosage for morning, midday and evening for the patient, to arrive at the total daily units for the patient. It is noted that if the recommend dosage changes to, for example, 0.4 U/kg, the healthcare provider can use the arrow in box 221 to adjust the dosage, which will change the breakdown of the dosage in the subsequent boxes for time of day and total daily units.

Box 222 in FIG. 10 provides LP considerations that can be reviewed by the healthcare provider. Box 224, which follows box 220, provides recommendations for a follow-up in a patient's medical condition and so on. Box 226, which follows box 224, enables the healthcare provider to adjust the stage to insulin dosage if deemed necessary from the follow-up in box 224.

Figure 11:
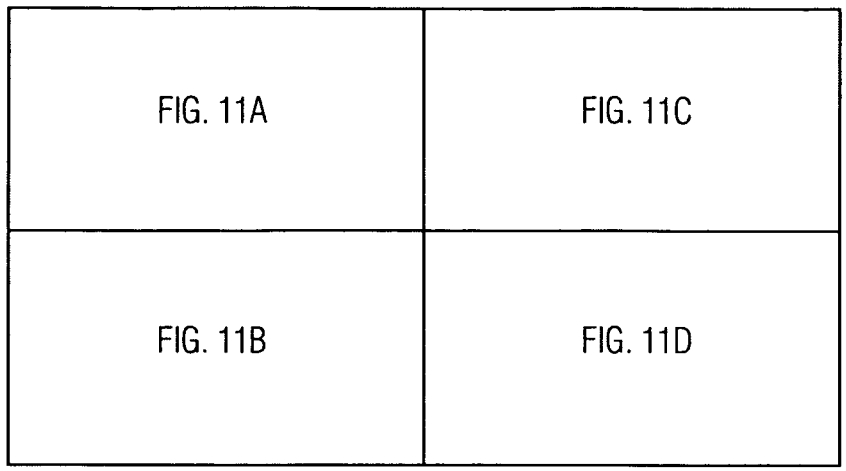
FIG. 11 illustrates an example of a Type 2 diabetes stage 2 adjust display that can be generated on a display screen of a workstation employing the network shown in FIG. 1 in accordance with an embodiment of the present invention.

That is, if the healthcare provider determines that the insulin for stage should be adjusted, the healthcare provider can use the mouse at his or her workstation 110 to click on the "insulin stage 2" adjust term in box 226. By doing so, the web browser of the workstation 110 displays a stage 2 adjust screen 230 as shown in FIG. 11. Stage 2 adjust screen 230 includes boxes 232 through 252 which provide recommendations to the healthcare provider to change the insulin based on certain conditions.

For example, box 234 takes into account the patient's interim history and physical conditions, as well as the laboratory results, while box 236 provides recommendations for considering different insulin stages. Box 238 considers whether the patient's SMBG is within the target range. If so, box 240 provides a recommendation that the patient maintain the stage to insulin dosage. Box 242 considers the patient's monthly assessment which, if improvement is shown, indicates that the recommendations in box 244 should be followed. If improvement is not shown, the guidelines recommended in box 246 that the patient's day-to-day management be assessed, and box 248 provides guidelines to determine whether the patient's dosage is sufficient. Box 250 enables the healthcare provider to provide a recommended adjustment to the patient's insulin dosage. Box 252 provides recommendations for changing the patient's dosage to follow the insulin stage 3 or insulin stage 4 recommendations.

Figure 12:
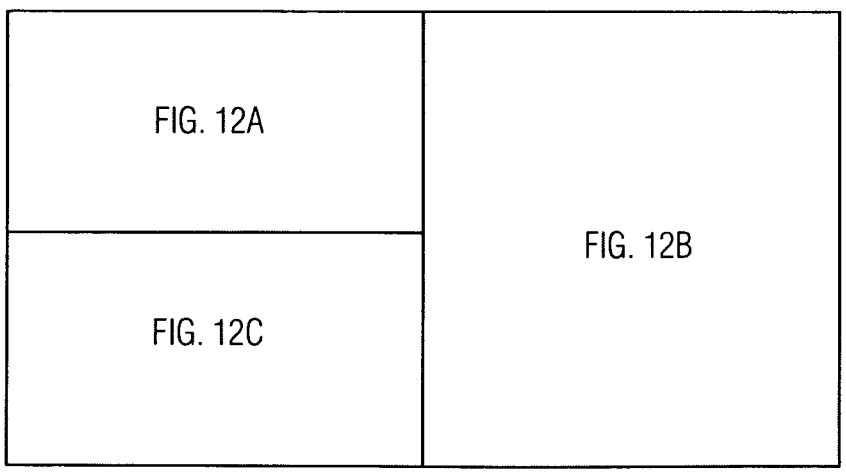
FIG. 12 illustrates an example of an insulin stage 3A start display that can be generated on a display screen of a workstation employed in the network shown in FIG. 1 in accordance with an embodiment of the present invention.
Figure 11A:
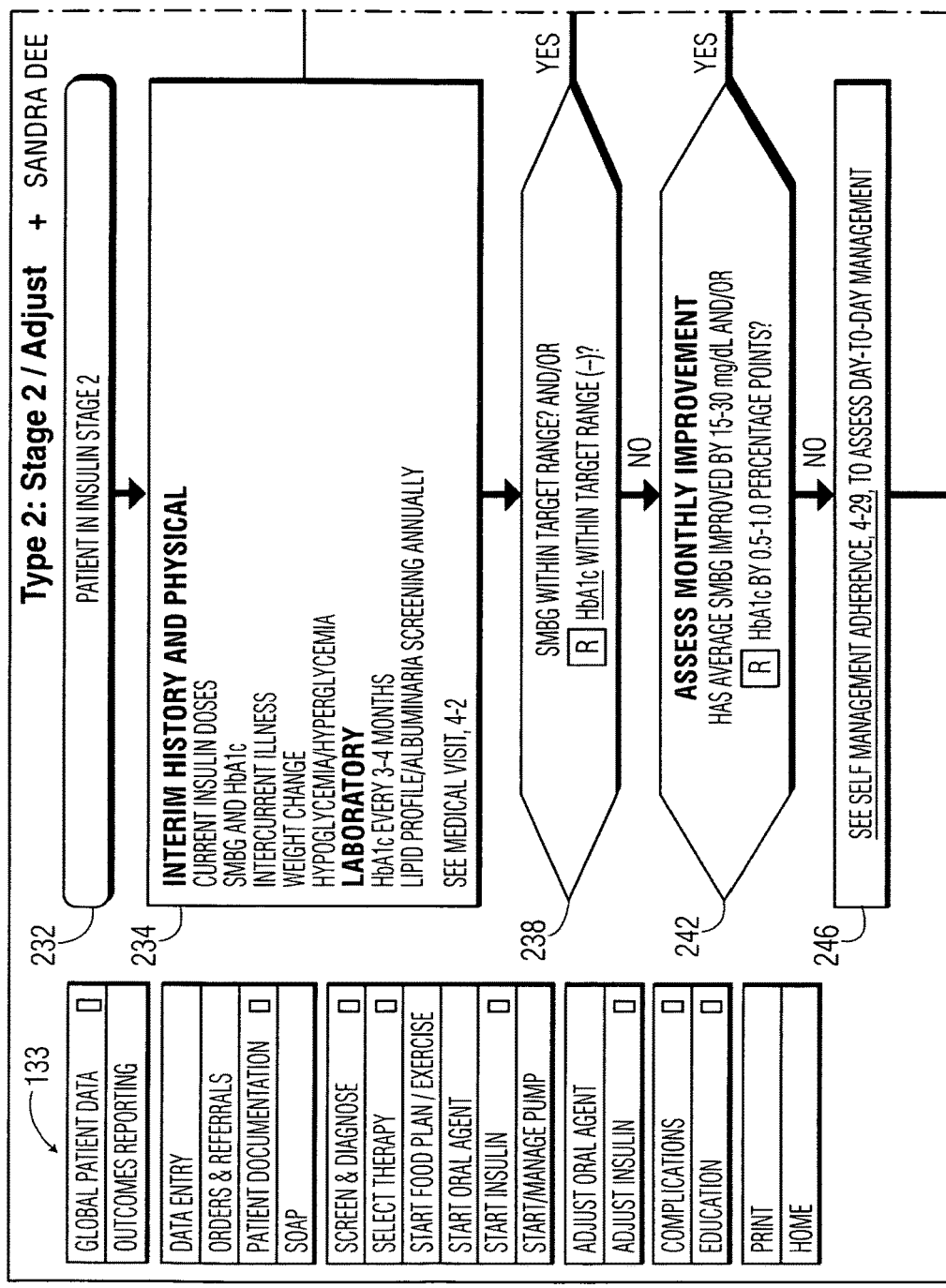
Figure 11B:
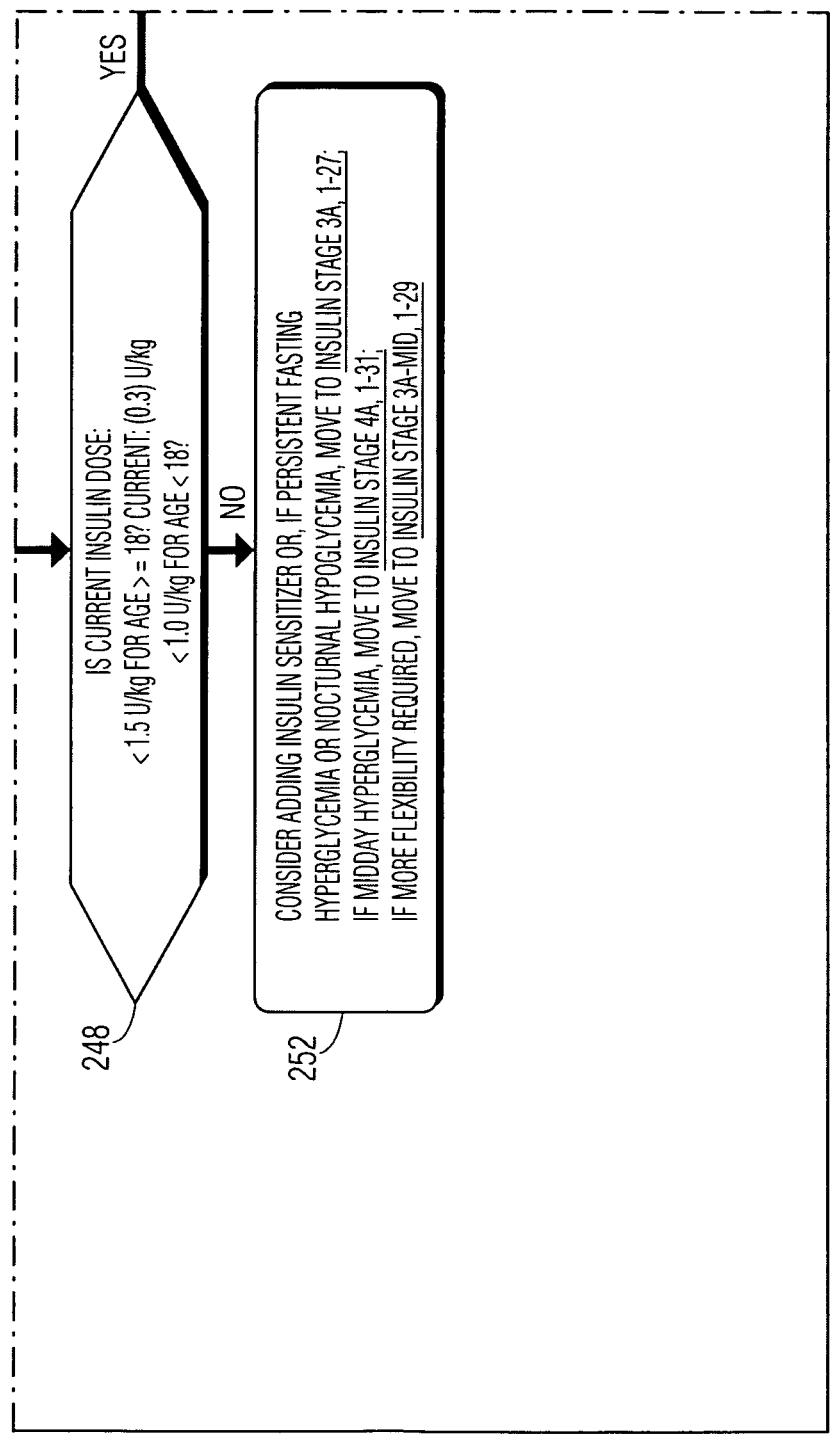
Figure 11C:
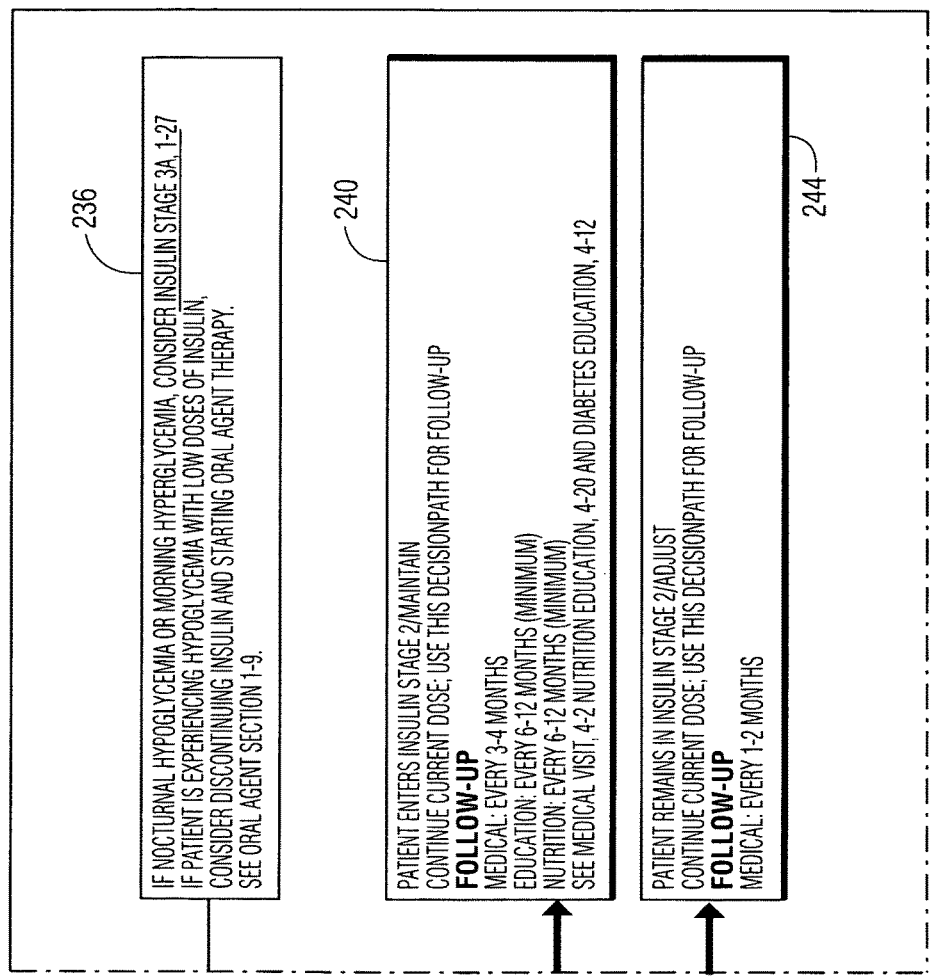
Figure 12A:
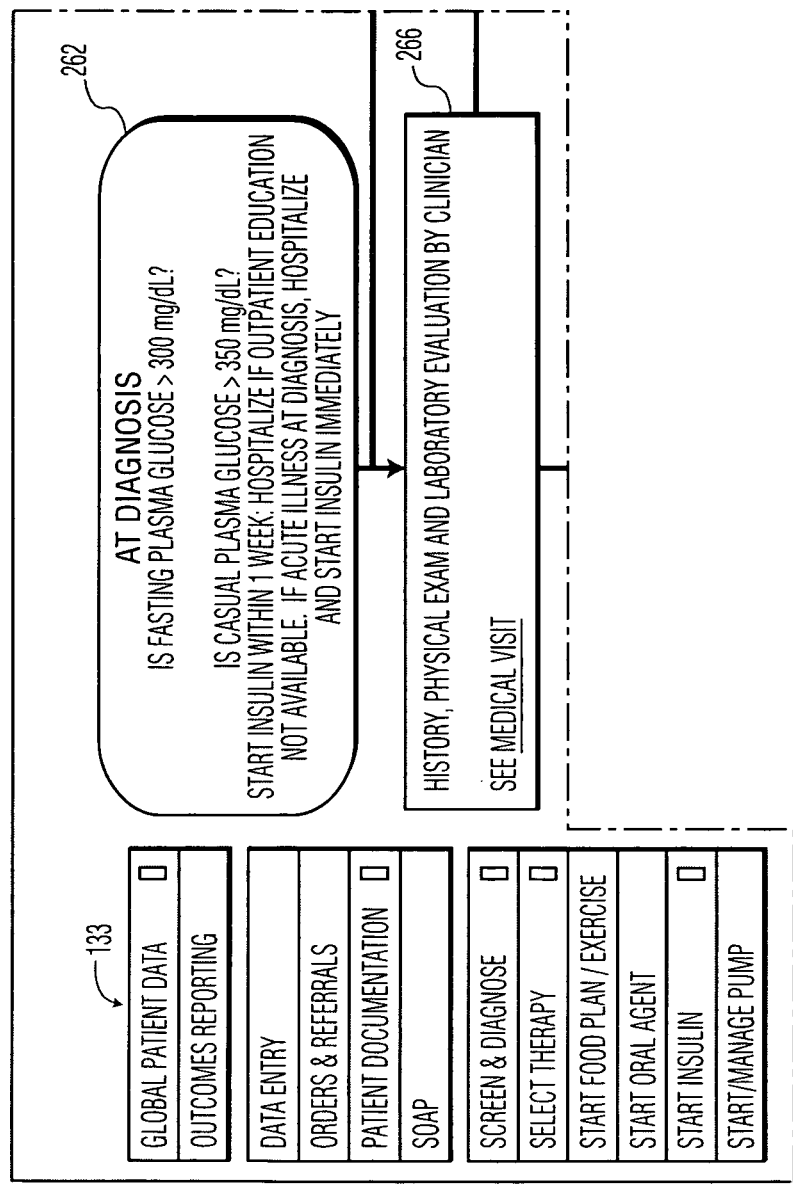
Figure 12B:
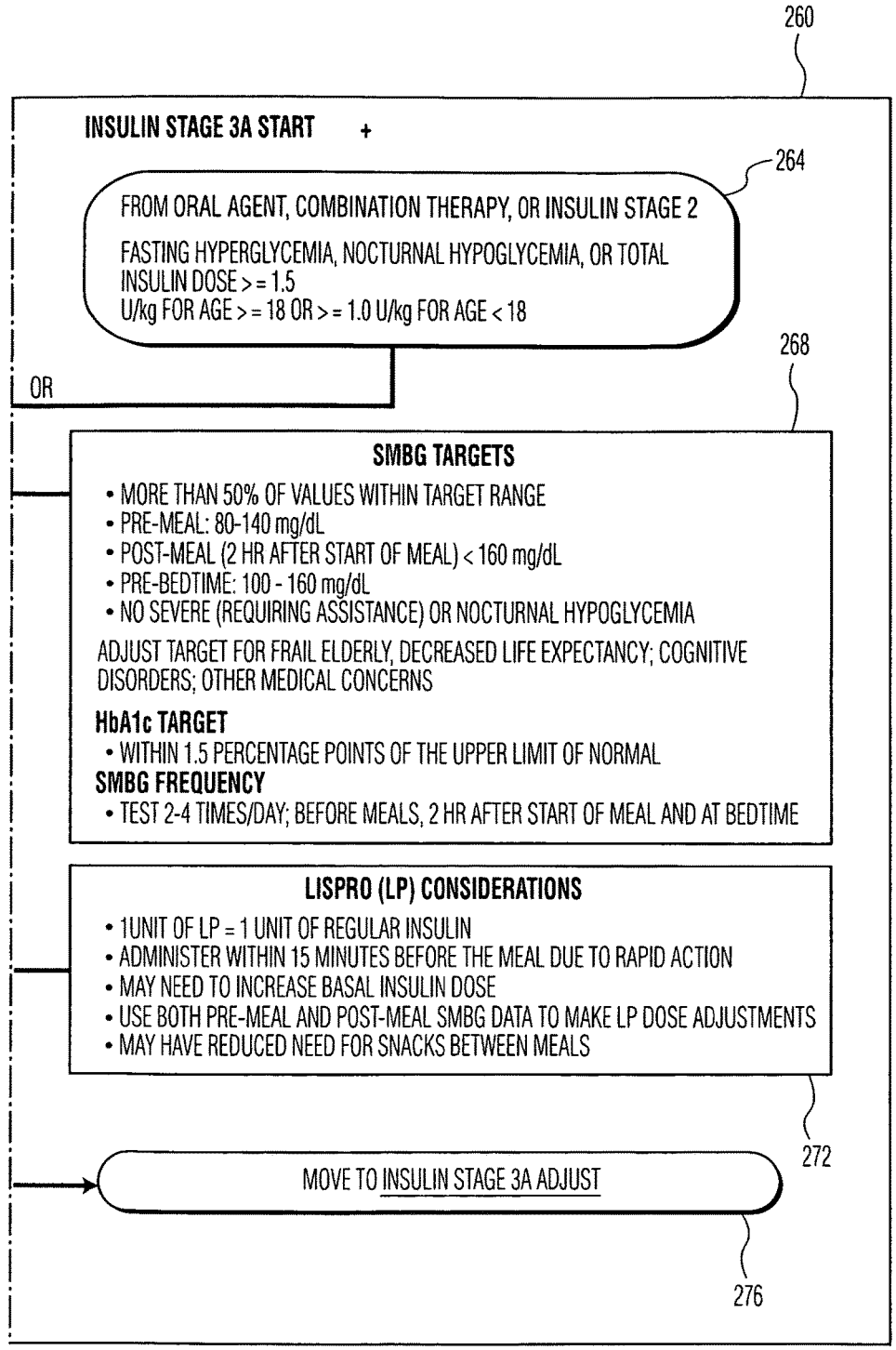
Figure 12C:
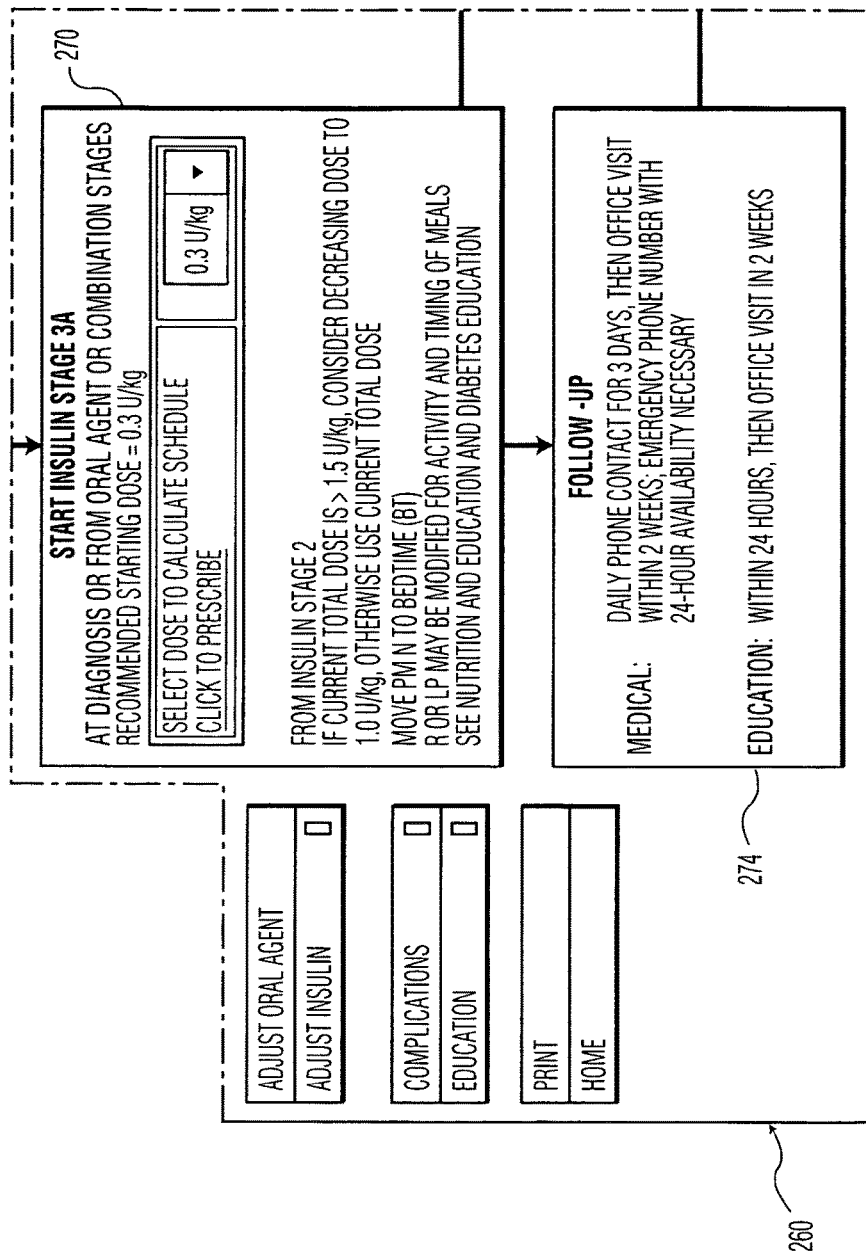
Figure 13:
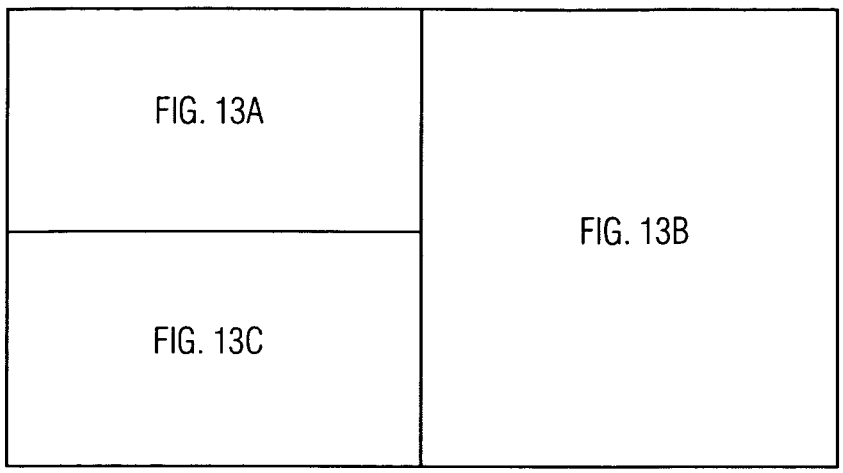
FIG. 13 illustrates an example of an insulin stage 4A start display that can be generated on a display screen of a workstation employed in a network shown in FIG. 1 in accordance with an embodiment of the present invention.

Returning to FIG. 7, if the healthcare provider determines from the diagnosis in box 170 that the patient should be given insulin stage 3A dosage, the healthcare provider can use the mouse at his or her workstation 110 to click on the insulin stage 3A term in box 182. In doing so, the browser on workstation 110 will display the insulin stage 3A start display screen 260 as shown in FIG. 12. The display screen 250 includes boxes 262 through 276 which are similar to boxes 212 through 226 in display screen 210 shown in FIG. 10 and which will not be described in detail here. Returning to FIG. 7, if the healthcare provider determines from the guidelines set forth in box 170 that the patient should enter insulin stage 4A, the healthcare provider can use the mouse at his or her workstation 110 to click on the term insulin stage 4A in box 184 to cause browser to display an insulin stage for a start screen 280 as shown in FIG. 13. Screen 280 includes boxes 282 through 296 which are similar to boxes 262 through 276 shown in FIG. 12 and boxes 212 and 226 shown in FIG. 10, and thus will not be described in detail here. Also, box 276 in FIG. 12 and box 296 in FIG. 13 enable the healthcare provider to provide insulin stage 3A adjustment and insulin stage 4A adjustment, respectively, in a manner similar to the insulin stage 2A adjustment as shown in the display screen 230 set forth in FIG. 11.

Figure 14:
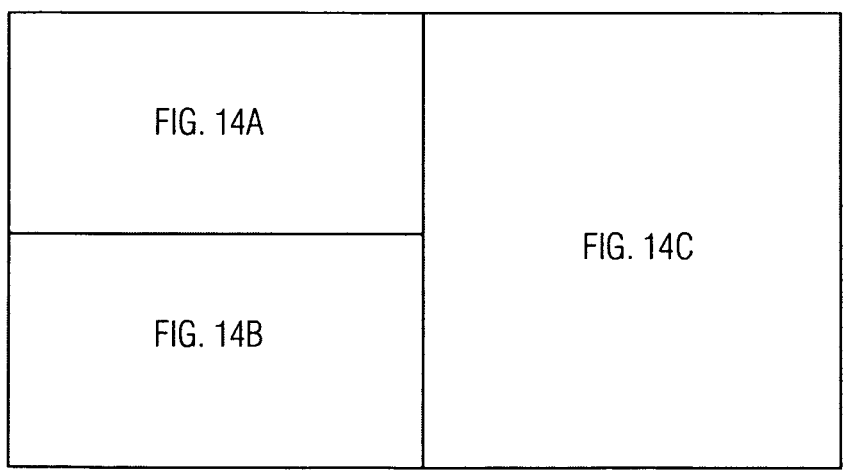
FIG. 14 illustrates an example of a screening and diagnosis display screen as shown in FIG. 6 that further displays a selection box according to an embodiment of the present invention.
Figure 13A:
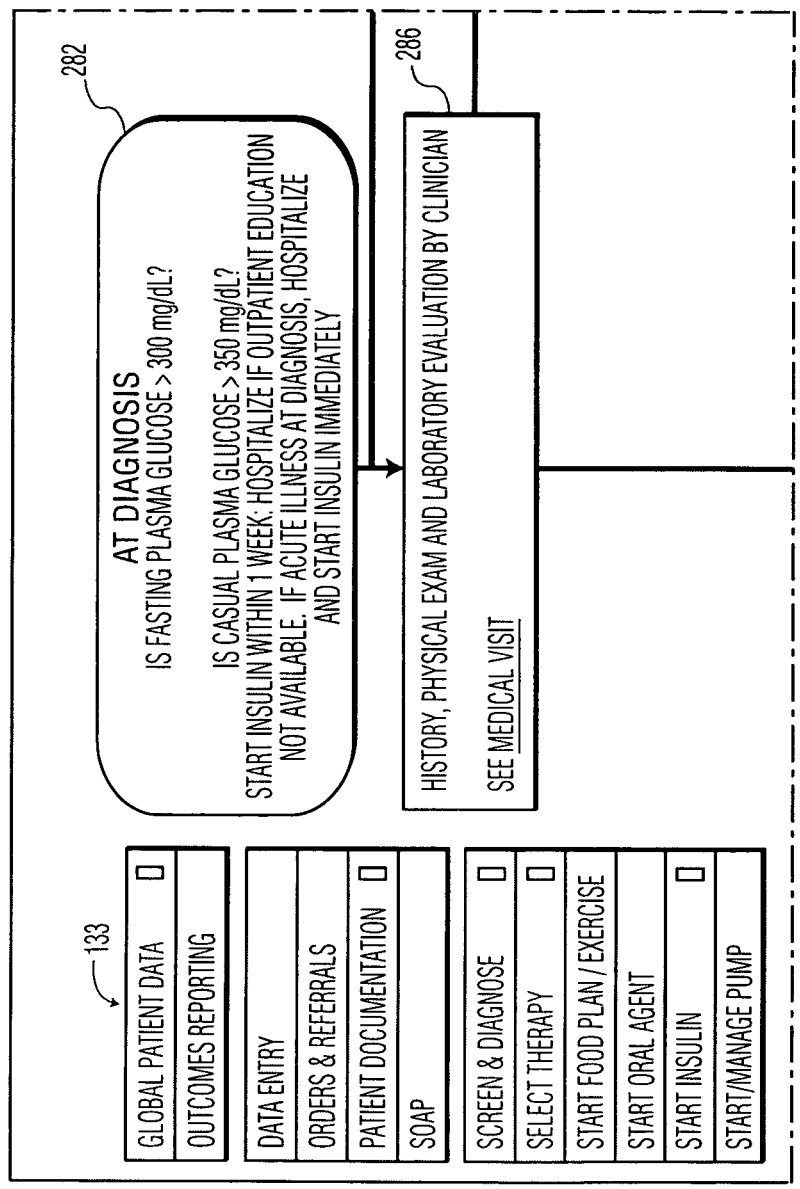
Figure 13B:
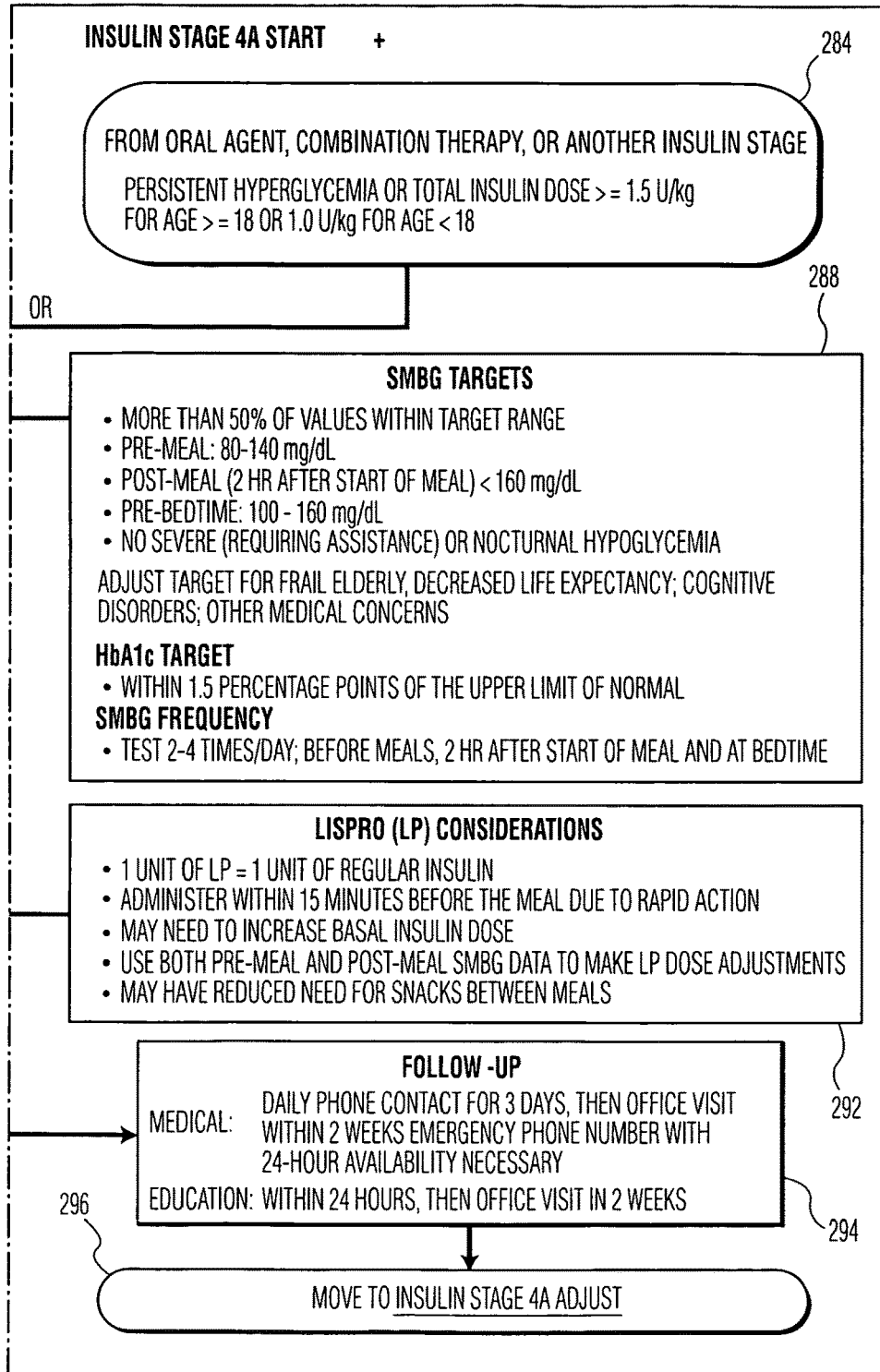
Figure 13C:
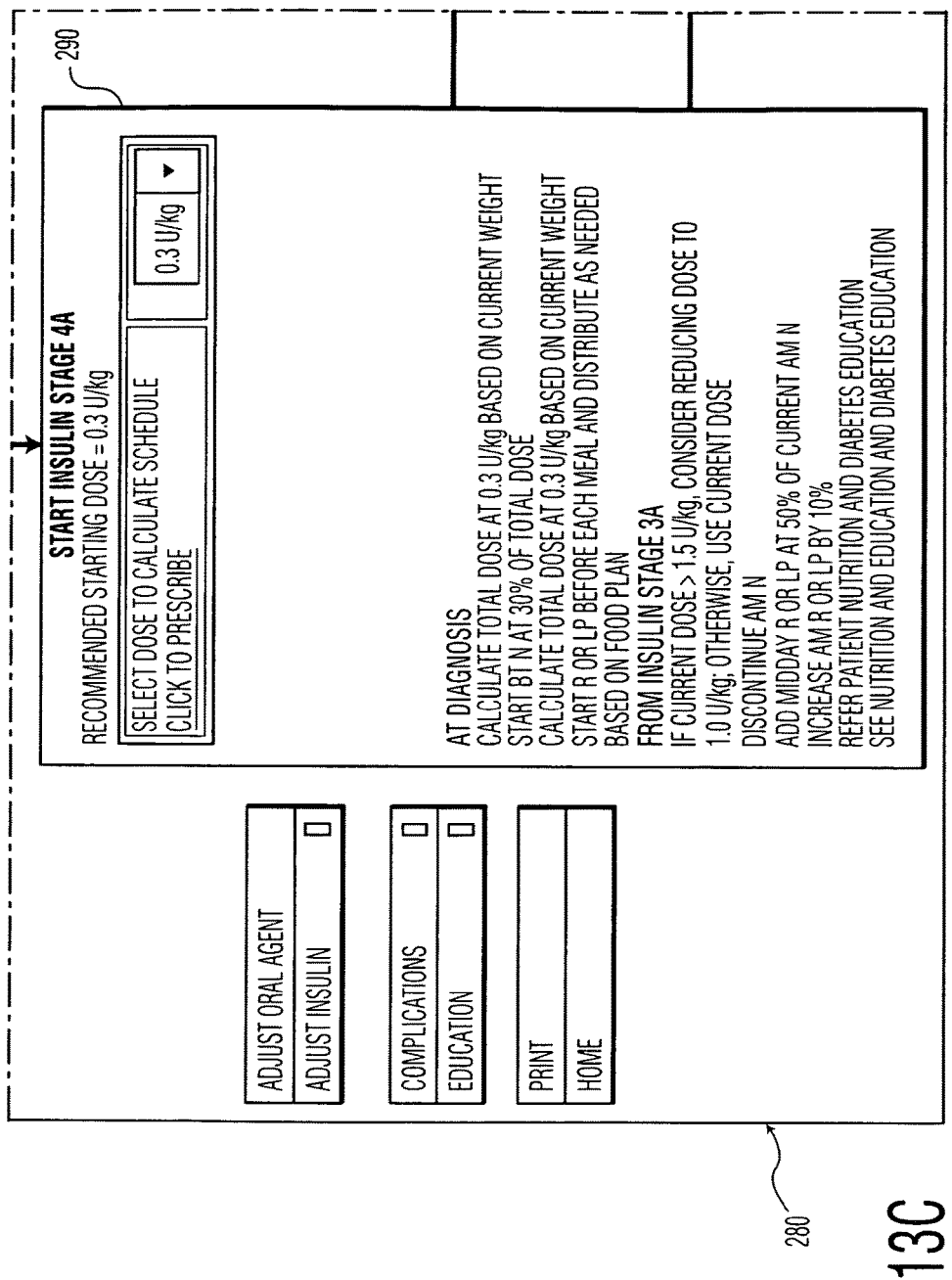
Figure 14A:
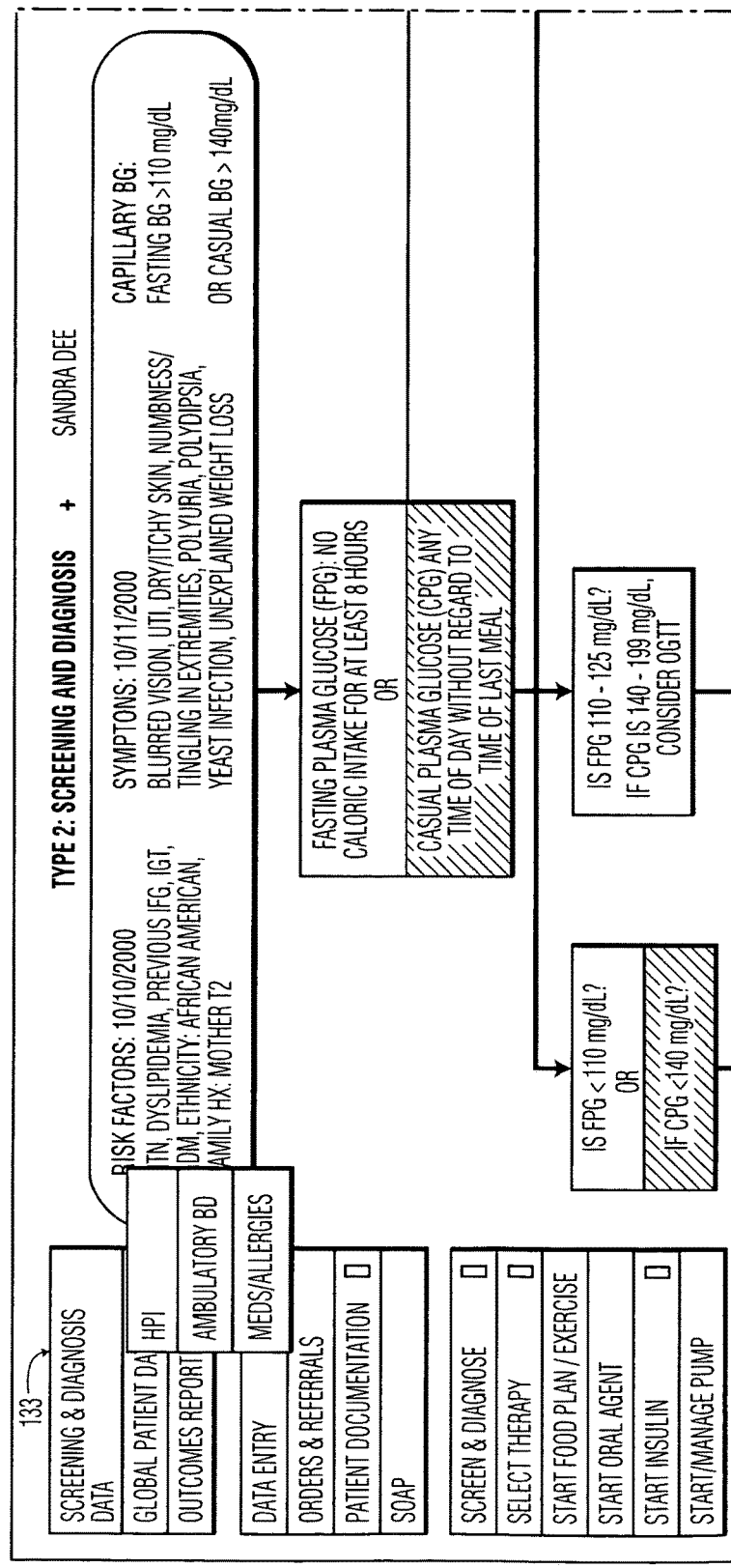
Figure 14B:
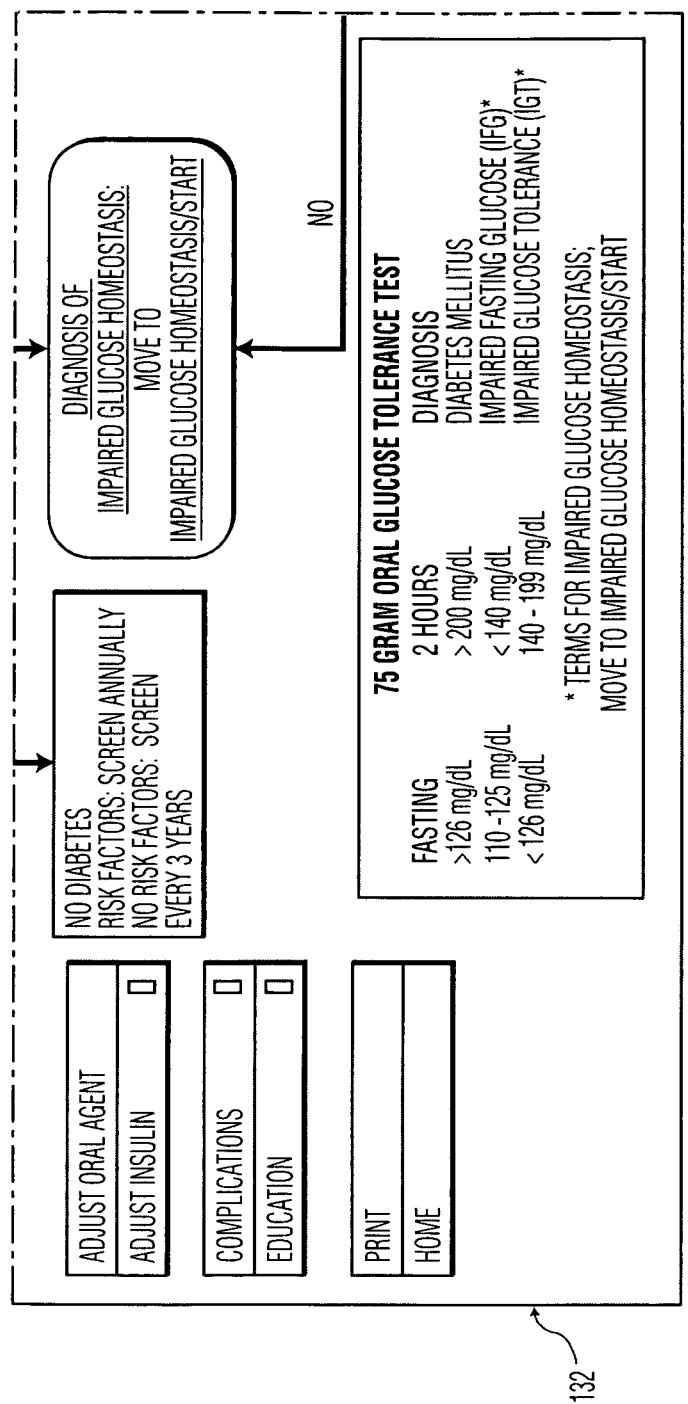
Figure 14C:
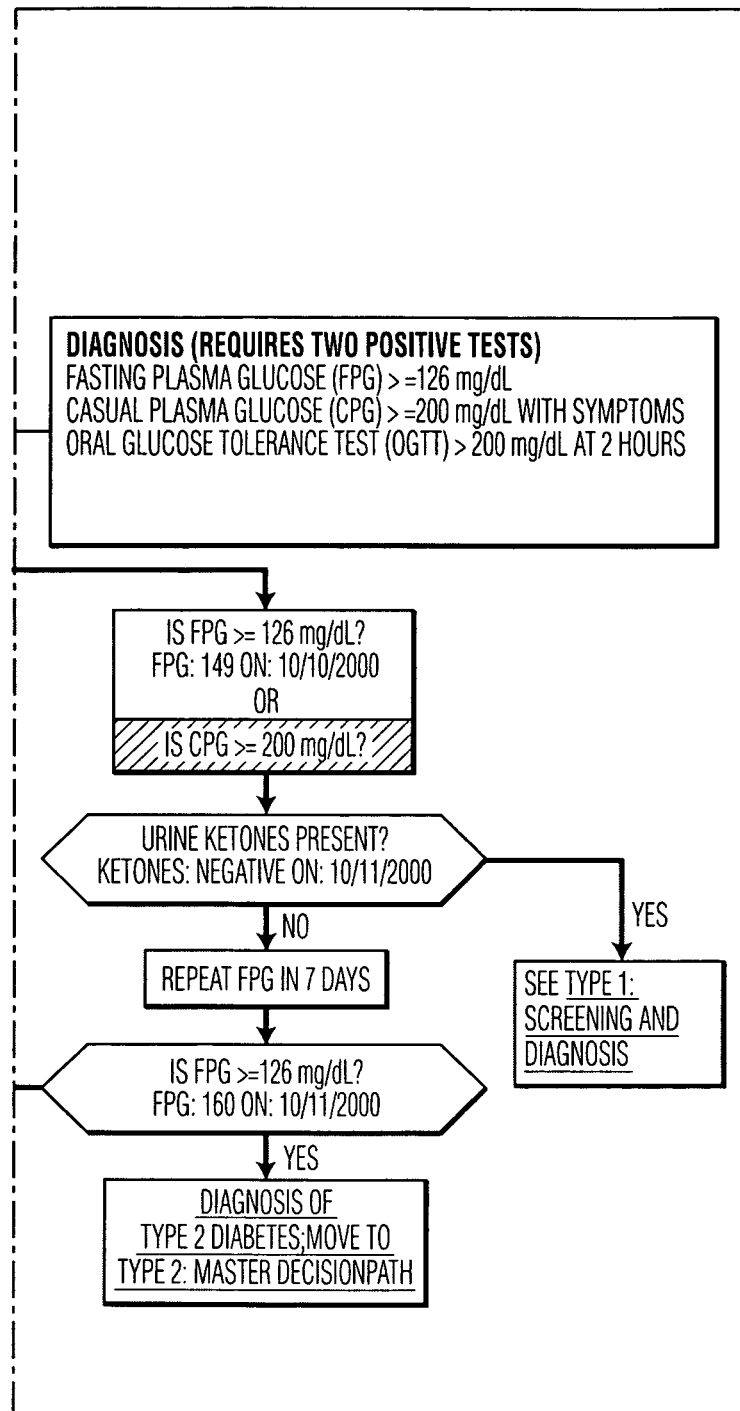
Figure 15:
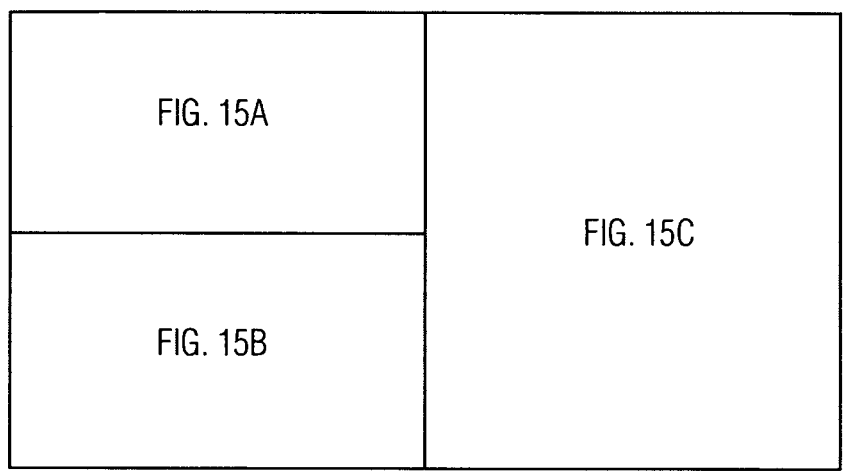
FIG. 15 is an example of a blood pressure display that can be displayed on the display screen of a workstation employed in the network shown in FIG. 1 in accordance with an embodiment of the present invention.
Figure 15A:
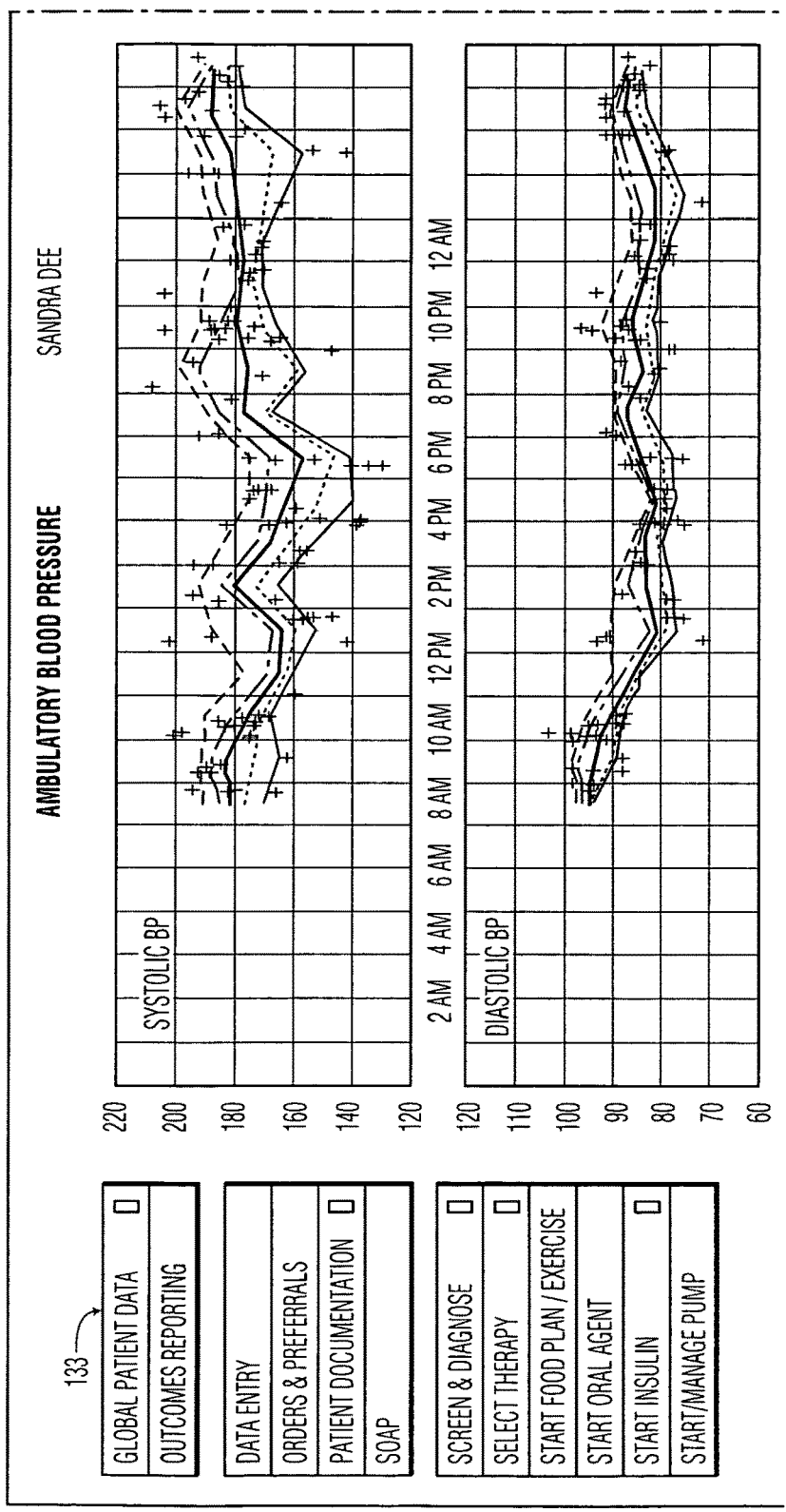
Figure 15B:
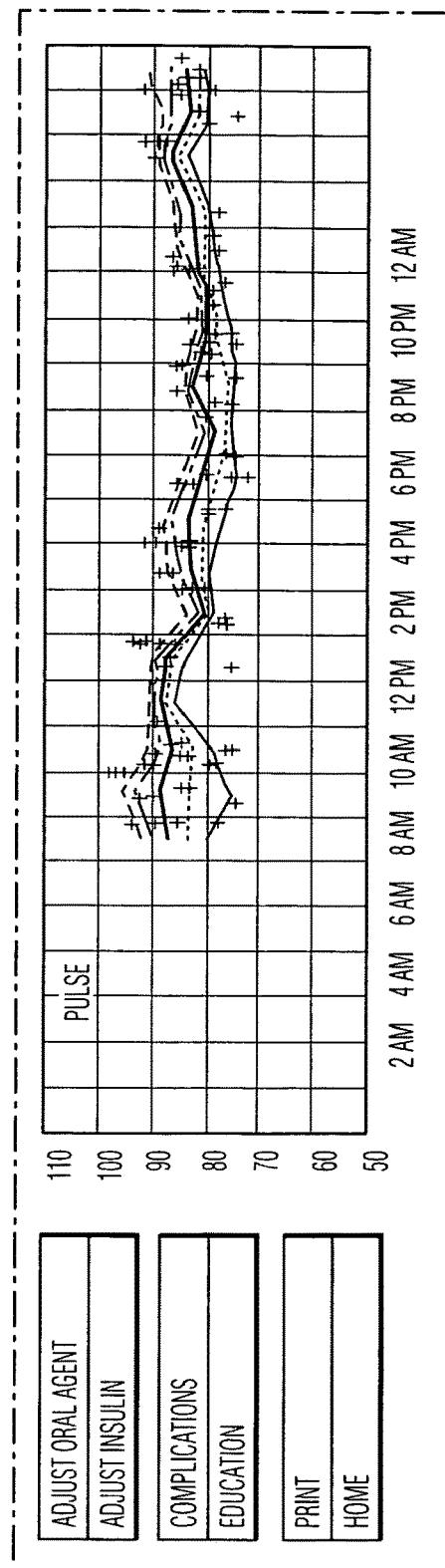
Figure 15C:
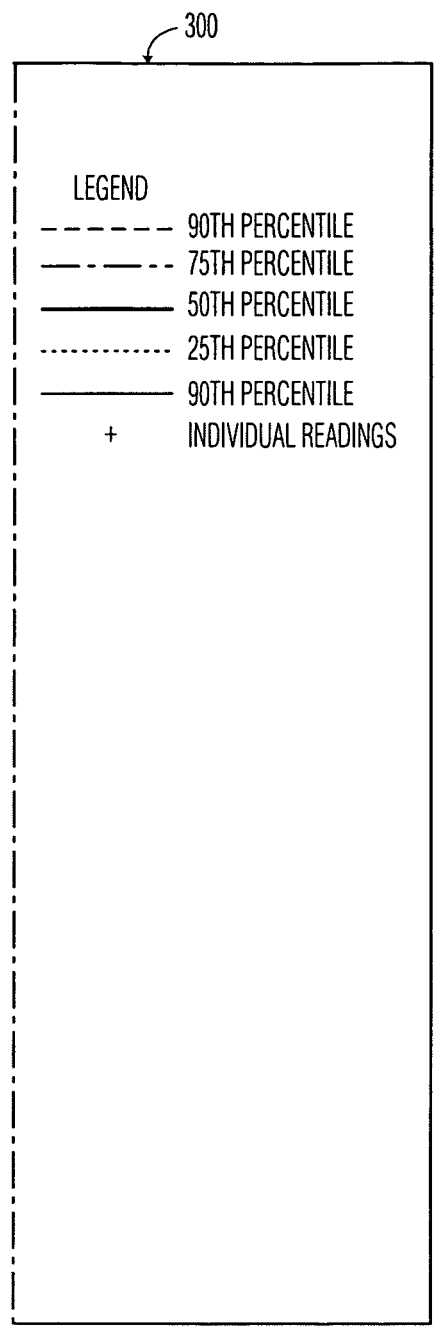
Figure 16:
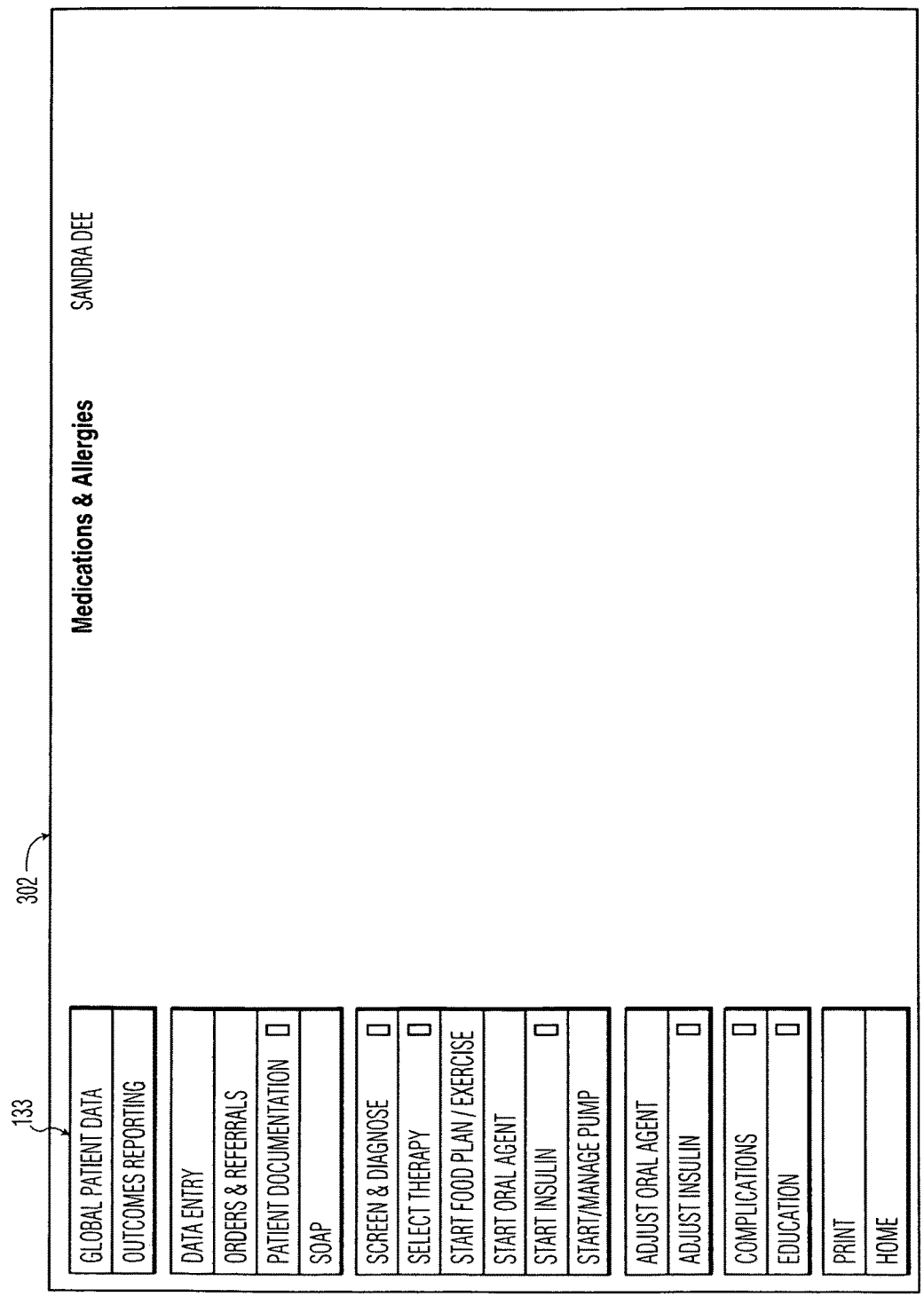
FIG. 16 is an example of a medications and allergies display that can be displayed on the display screen of a workstation employed in the network shown in FIG. 1 in accordance with an embodiment of the present invention.
Figure 17:
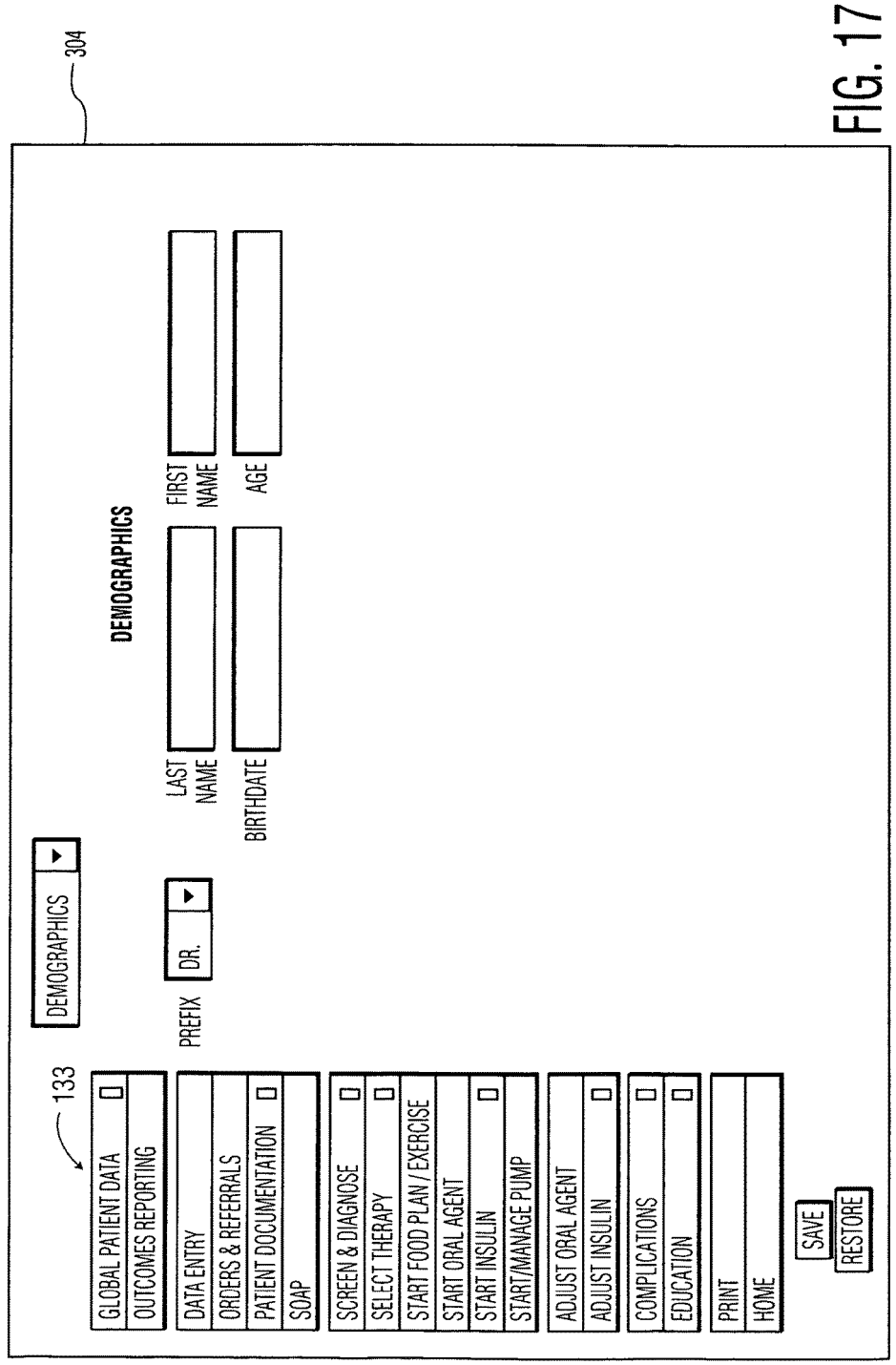
FIG. 17 is an example of a patient update information display that can be displayed on a display screen of the workstation employed in the network shown in FIG. 1 in accordance with an embodiment of the present invention.

It is also noted that the various buttons in the button column 133 on the displays discussed above which are displayed on the display screen of the workstation 110 can be used to generate additional display screens pertaining to the patient. For example, if the healthcare provider clicks on the global patient data button, a group of additional buttons can be displayed as shown in FIG. 14. The healthcare provider can thus click on these additional buttons to cause the workstation 110 to display, for example, a screen showing the patent's history in present illness (HPI), as well as ambulatory blood pressure (BP) as shown in display screen 300 in FIG. 15, and the patient's medicines and allergy information which can be entered in display screen 302 as shown in FIG. 16. The healthcare provider can also click on the data entry button to cause the workstation to display a patient data entry screen 304 as shown in FIG. 17. The healthcare provider can also click on any of the other buttons to display screens for performing additional tasks.

For example, the healthcare provider can click on the outcomes reporting button to display reports on patient progress. More particularly, the outcomes reporting button could be clicked on to display population data reports, such as NCQA, HEDIS or JCAHO reports, which are of critical importance to Health Care Organizations in securing and maintaining various forms of accreditation, and show a compilation of different patient data that can be provided to those organizations. The healthcare provider can click on the orders and referrals button to view medical orders and referrals that have been given to the patient. These orders and referrals can include templates or letters into which the patient data and diagnosis data can be automatically entered by the system, thereby obviating the need for redundant documentation by the clinician. That is, if the referral is a referral letter to a type of specialist, such as a nutritionist, the patient diagnosis (e.g., Type 2 diabetes) and patient data (e.g., SBGL readings) can be automatically inserted into the letter simply by the nature of the actions that the user takes while navigating the pathway screen(s) for the purpose of managing their patient or entity.

The healthcare provider can also click on any of the other buttons in button column 133 to display the desired display screens. For example, clicking on the patient documentation button will display the patient information such as the data that is in a patient's chart. Clicking on the screen and diagnose button will display the screen and diagnose display screen 132 as shown in FIG. 6, and clicking on the start food plan and exercise button will display the food plan and exercise display screen 186 as shown in FIG. 8. Clicking on the start insulin display screen button will enable the healthcare provider to display the selected insulin display screen as shown in FIGS. 10, 12 and 13, and clicking on the adjust insulin display screen will show an insulin adjustment display screen as shown in FIG. 11. Clicking on the start oral or start/manage pump buttons will display appropriate pathways similar to those shown in FIGS. 10, 12 and 13 but which pertain to oral or pump-administered medications. Clicking on the SOAP (subjective objective assessment and plan) button will display a display screen into which the healthcare provider can enter additional SOAP notes, beyond those automatically generated by the system in conjunction with the user's use of the system, as can be appreciated by one skilled in the art. Clicking on the select therapy button displays the master pathway as shown in FIG. 7. Clicking on the print button will enable the healthcare provider to print the displayed screen, and clicking on the home button returns the display to that shown in FIG. 5.

Figure 18:
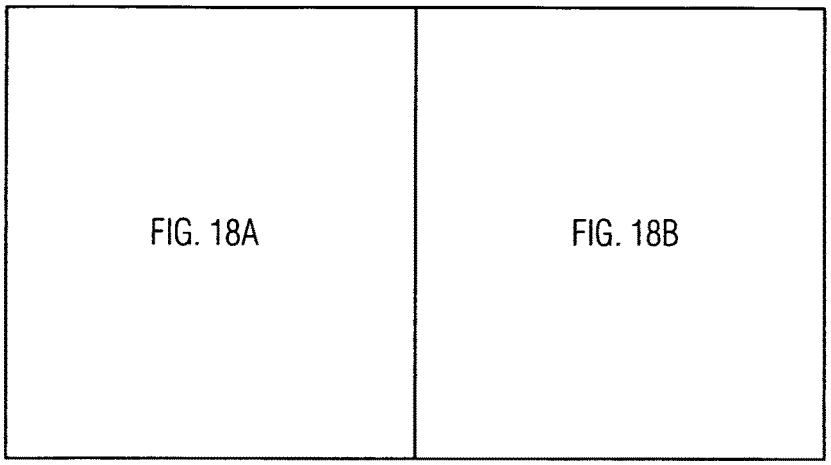
FIG. 18 is a self management adherence assessment display that can be generated on display screen of a workstation employed in the network shown in FIG. 1 in accordance with an embodiment of the present invention.
Figure 19:
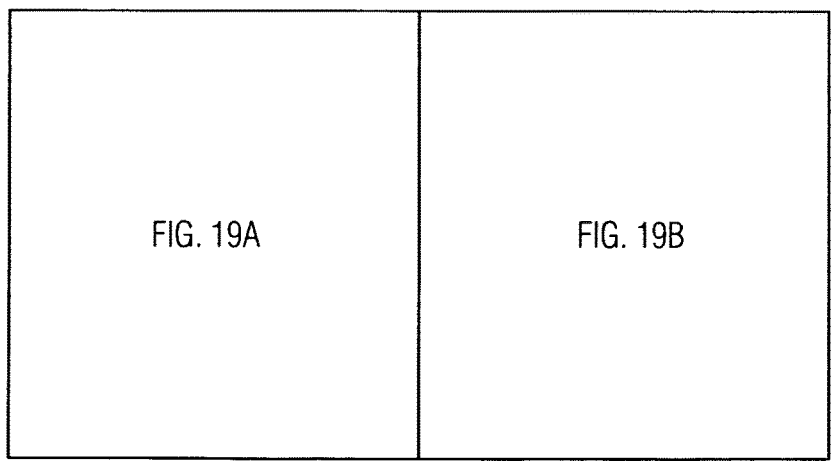
FIG. 19 is an example of a hypertension diagnosis display that can be displayed on a display screen of a workstation employed in the network shown in FIG. 1 in accordance with an embodiment of the present invention.
Figure 18A:
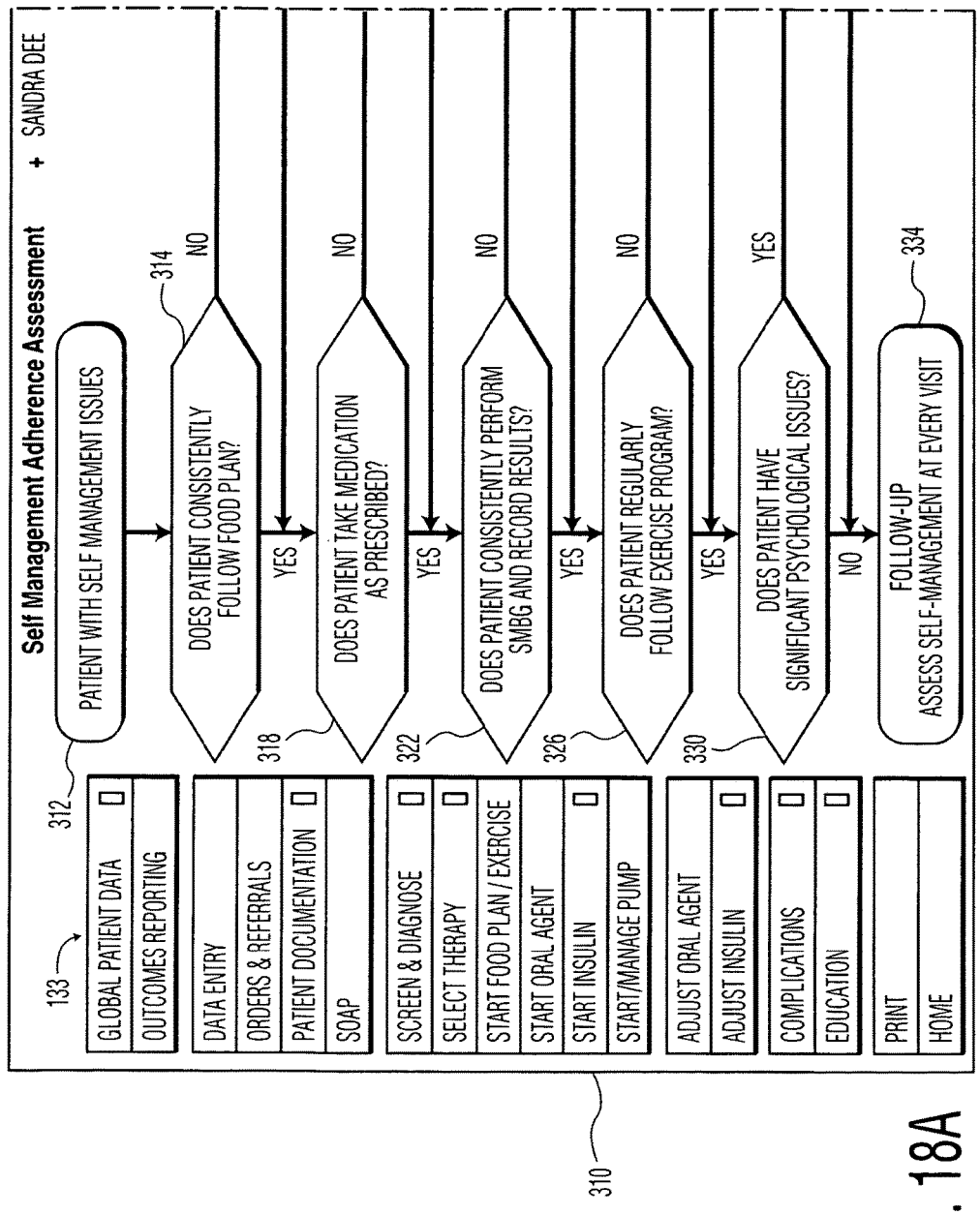
Figure 18B:
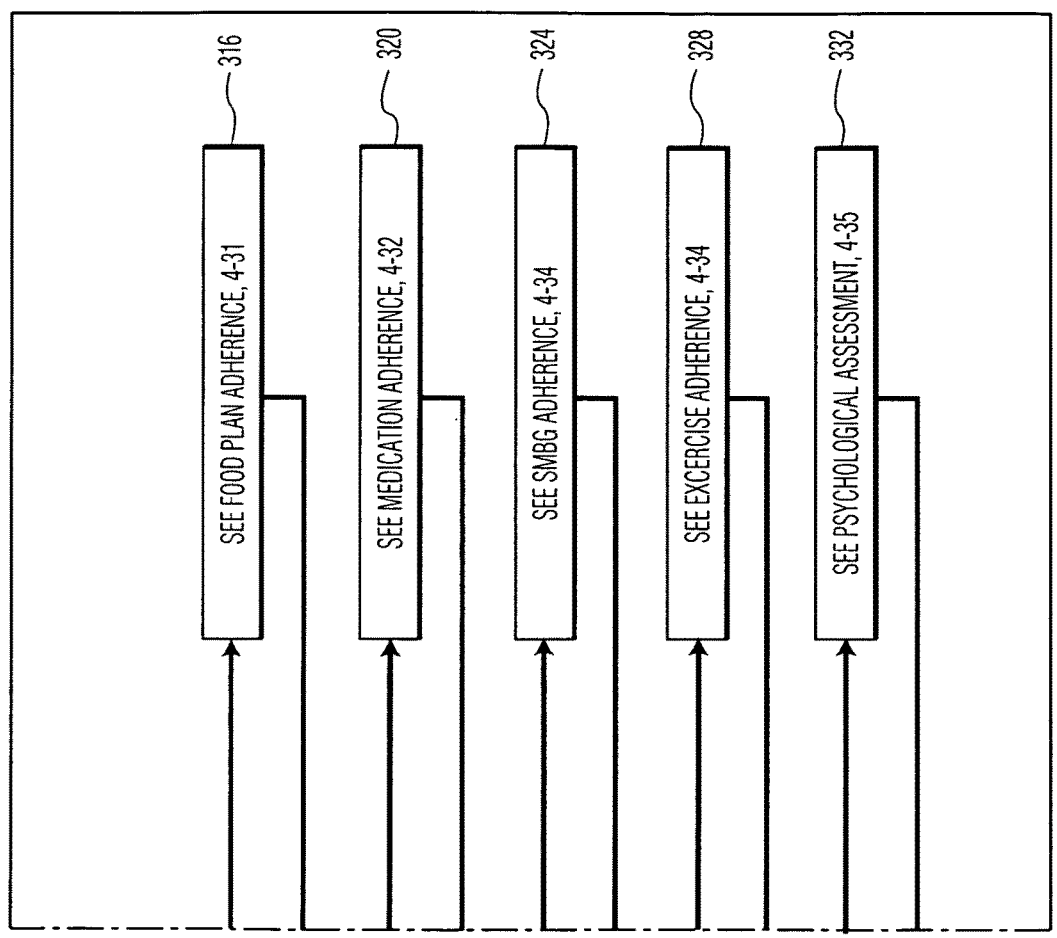
Figure 19A:
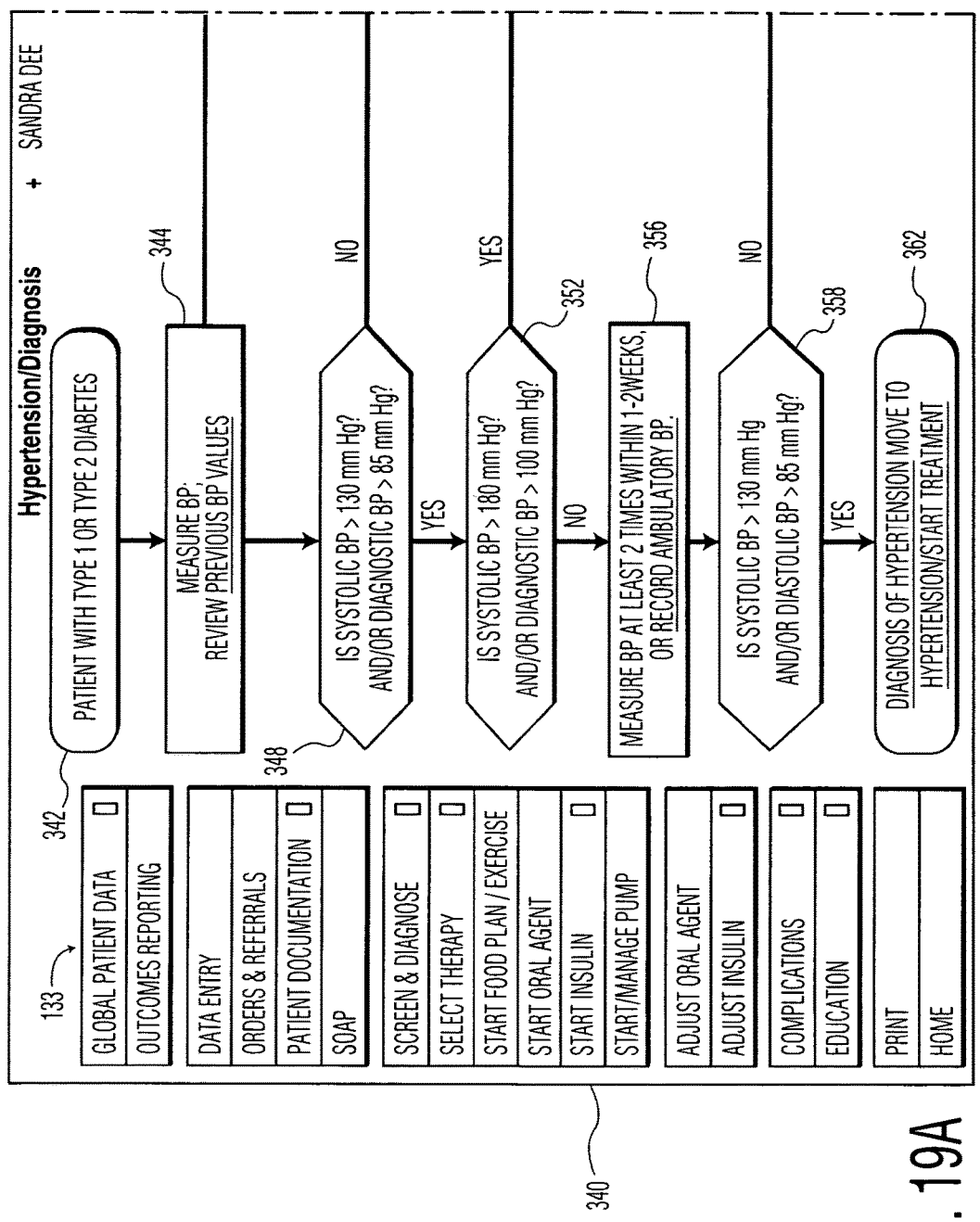
Figure 19B:
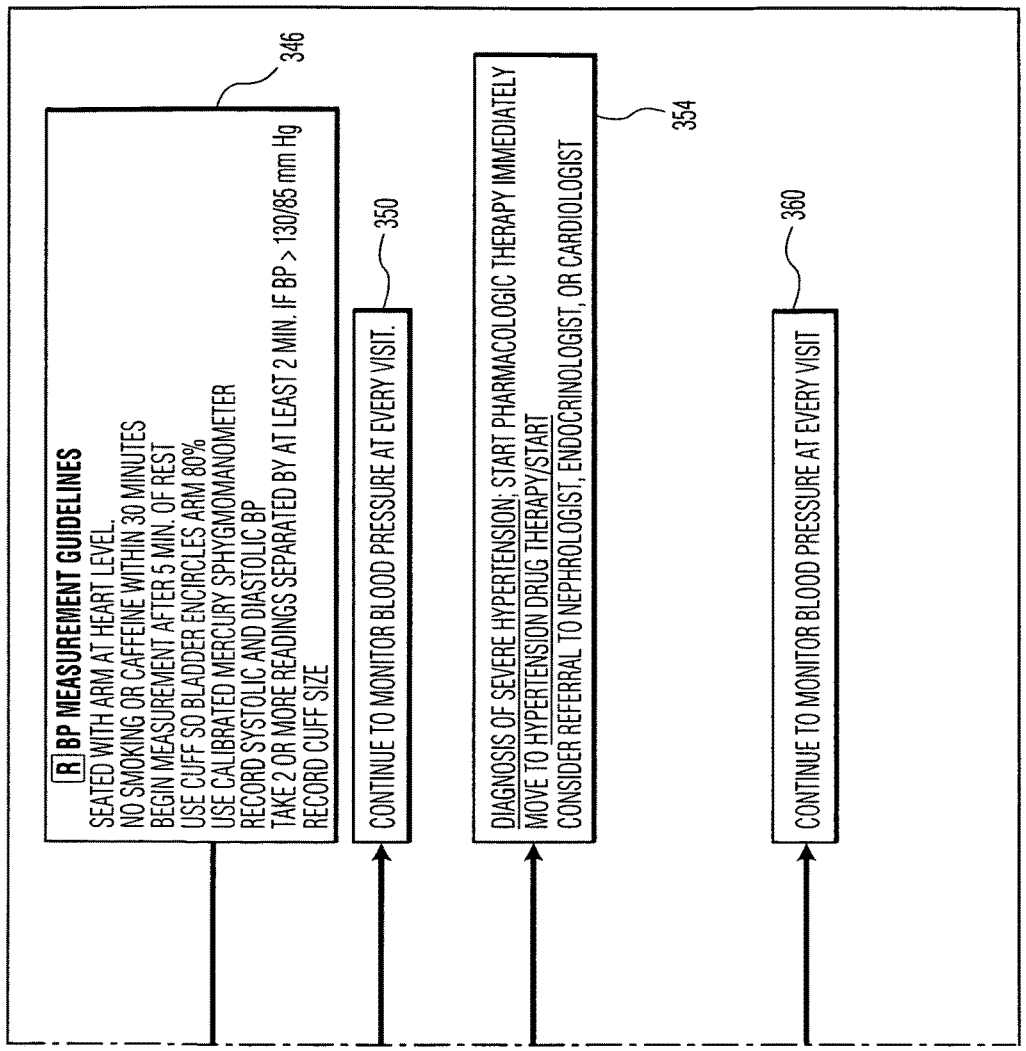
Figure 20:
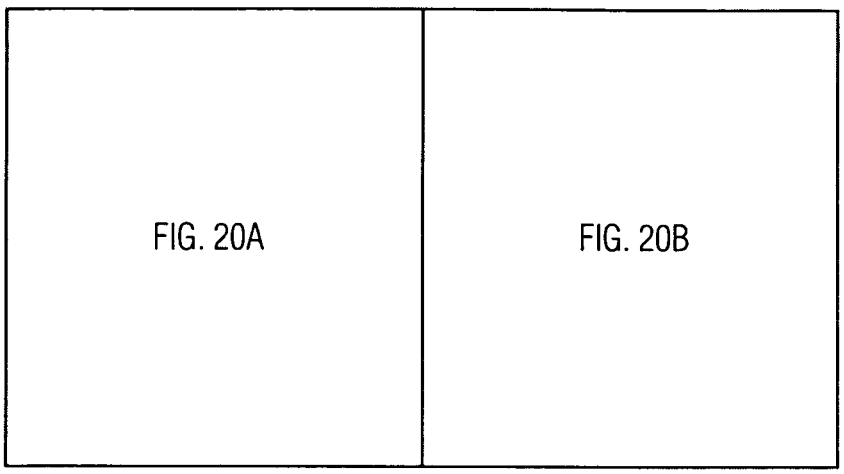
FIG. 20 is an example of a hypertension diagnosis display as shown in FIG. 19 that further displays a box containing desired blood pressure readings according to an embodiment of the present invention.

In addition, an appropriate button, such as the education button, can be clicked on to display self-management and adherence assessment display screen 310 as shown in FIG. 18 that includes boxes 312 through 334 which provide questions for the patient to answer and recommendations for the patient and will process those questions. Furthermore, the healthcare provider can click on the complications buttons to be able to diagnose whether or not the patent is developing any complications and then treatment pathways can provide guidance on their treatment For example, by clicking on the complication button, the workstation 110 can display a hypertension and diagnosis display screen 340 as shown in FIG. 19. The hypertension diagnosis display screen 340 includes boxes 342 through 362 which assist a healthcare provider in determining whether or not the patient is developing hypertension. For example, box 342 indicates that the patient with Type 1 or Type 2 diabetes can be suffering from hypertension, and subsequent box 344 instructs the healthcare provider to measure blood pressure and review previous blood pressure values. Box 346 provides blood pressure measurement guidelines. In addition, if the healthcare provider clicks on the box "R" in box 346, the workstation will display a dropdown box showing normal blood pressure range and diabetes blood pressure ranges as shown in FIG. 20.

Figure 21:
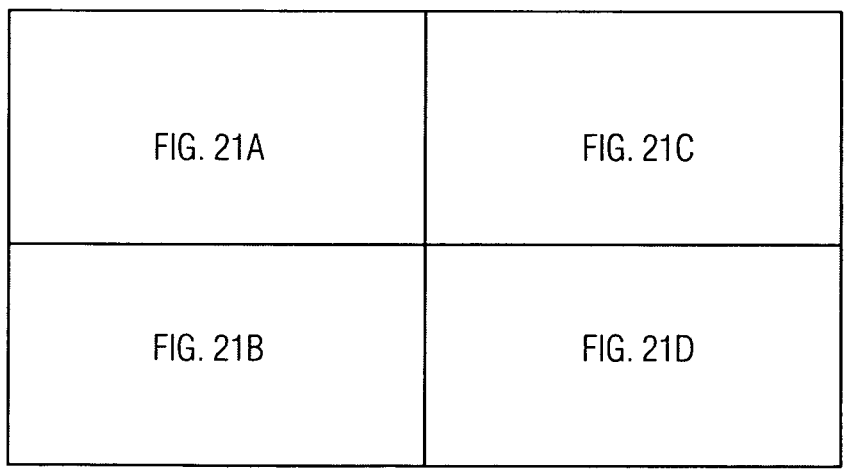
FIG. 21 is an example of a hypertension drug therapy start display that can be displayed on a display screen of a workstation employed in the network shown in FIG. 1 in accordance with an embodiment of the present invention.
Figure 20A:
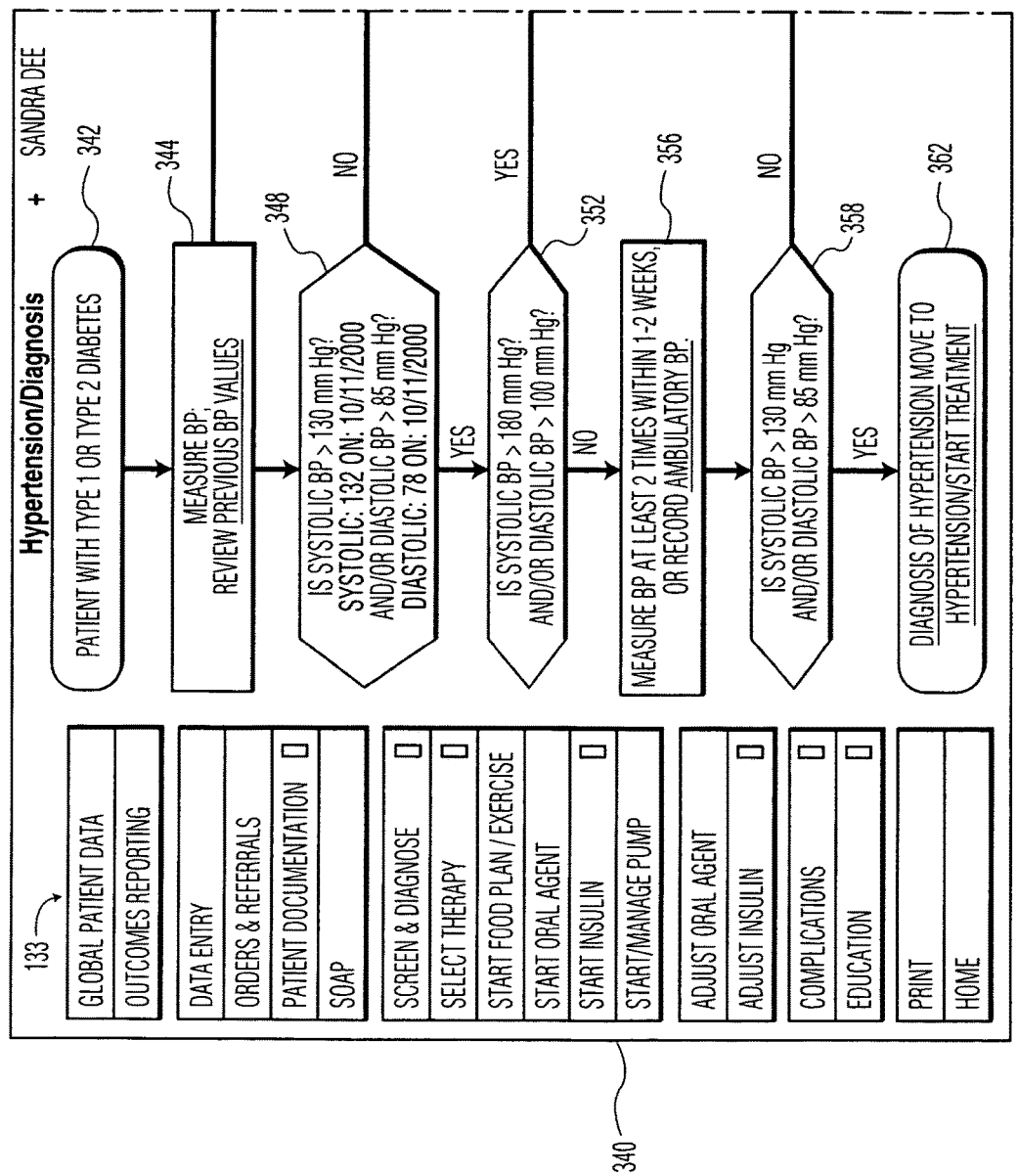
Figure 20B:
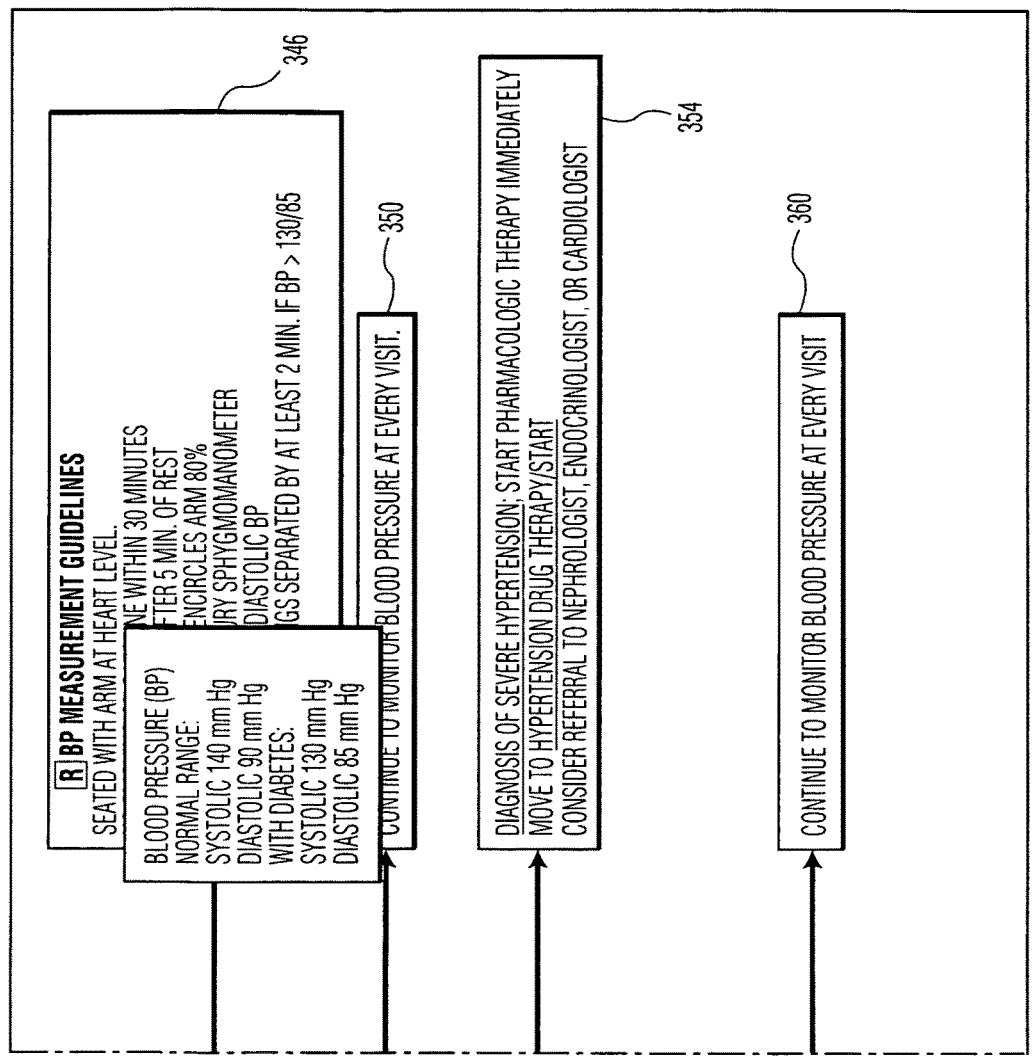
Figure 21A:
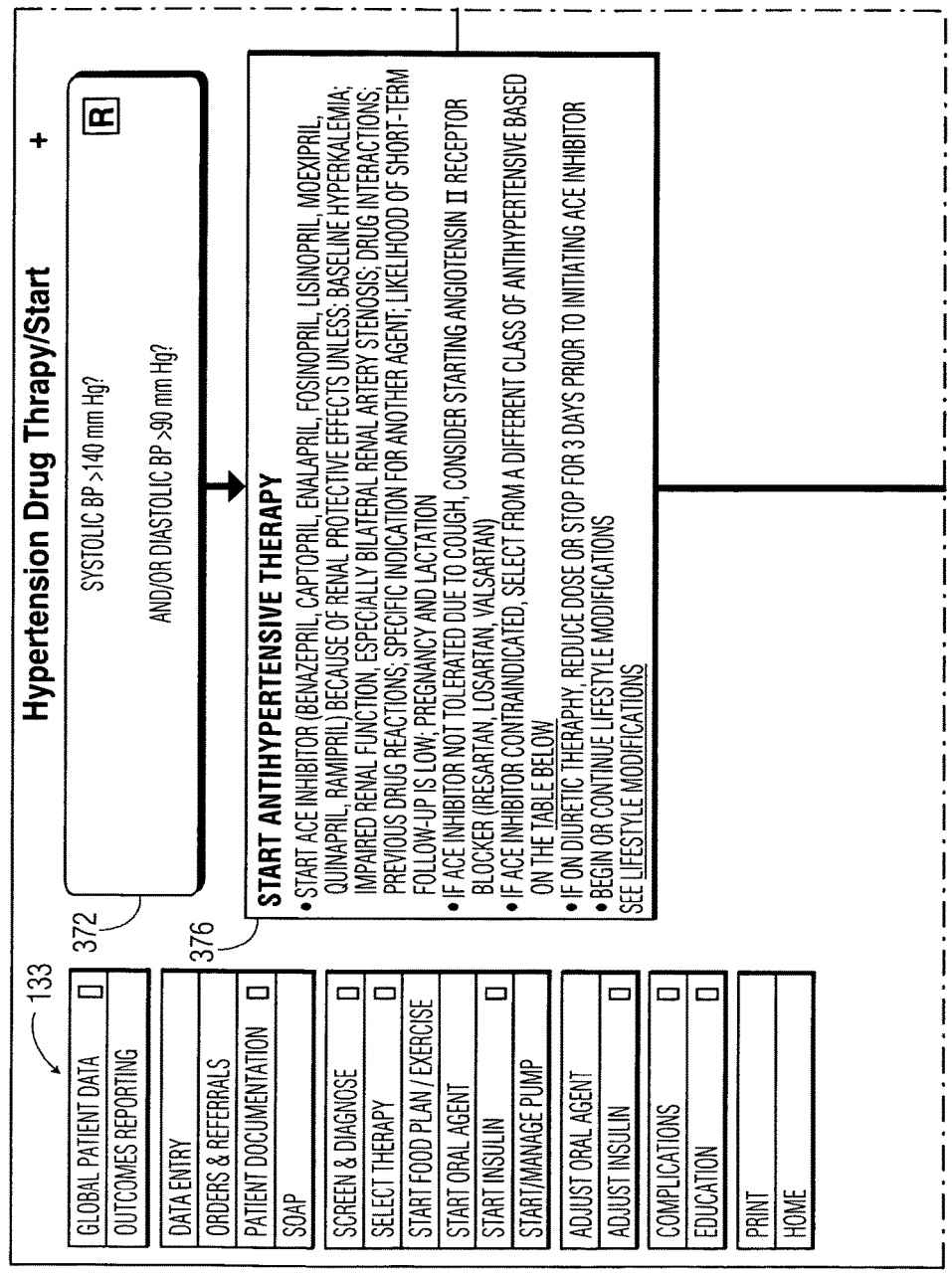
Figure 21B:
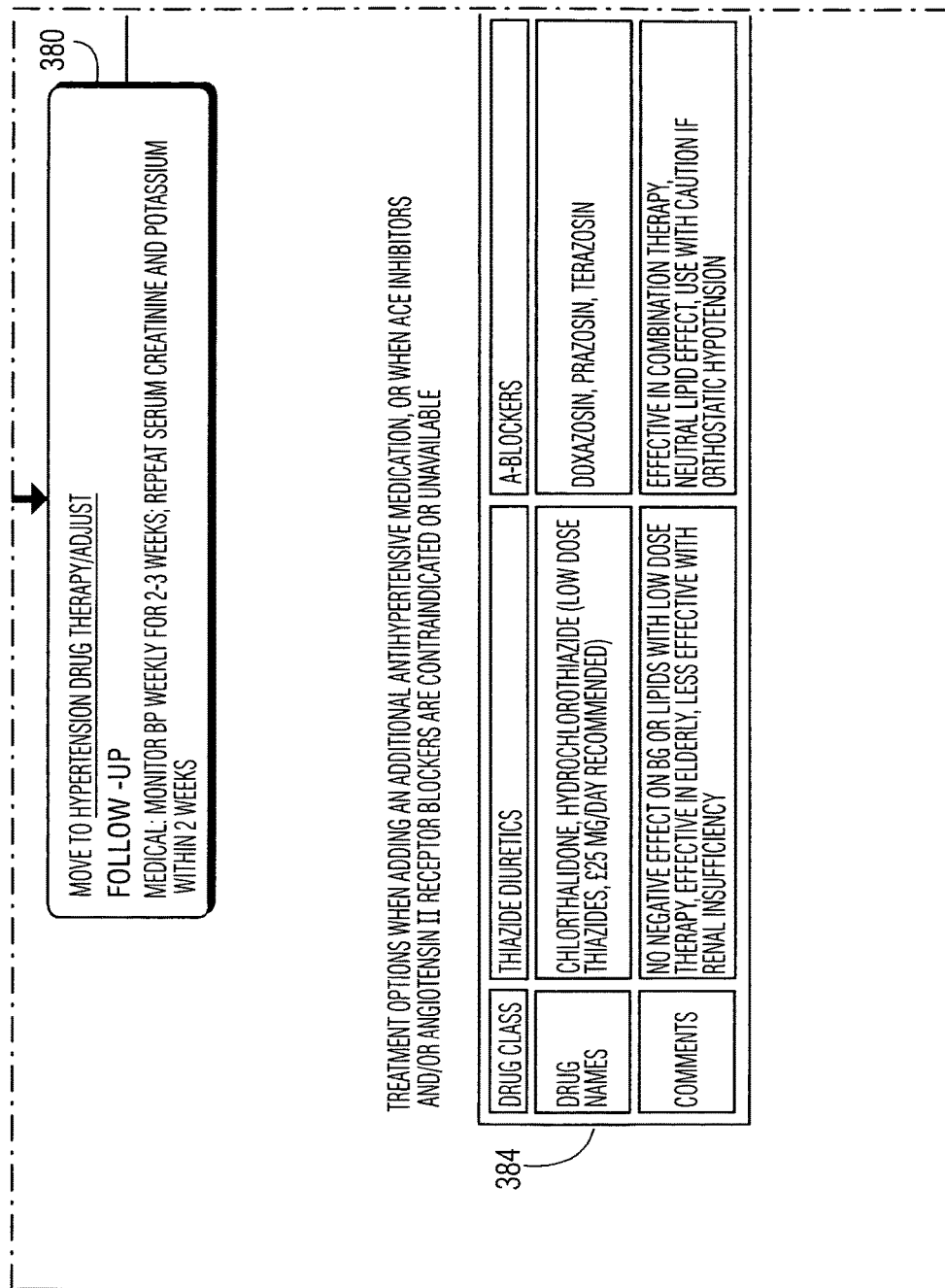
Figure 21D:
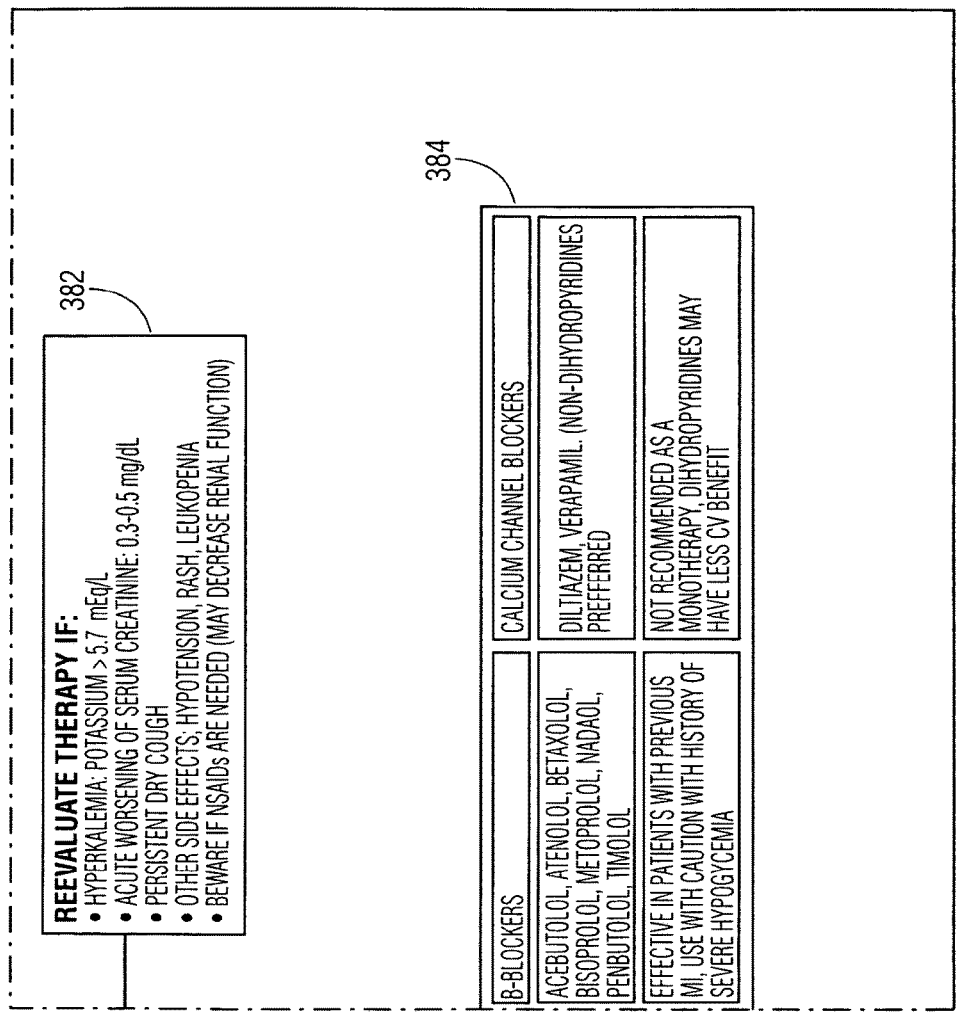

The additional boxes in display screen 340 similarly ask the healthcare provider questions to assist the healthcare provider with the diagnosis. If the healthcare provider reaches box 362, a recommendation is give to diagnose the patient with hypertension. The healthcare provider can then click on the hyper tension-start treatment term in box 362 to display a hypertension drug therapy start display screen 370 as shown in FIG. 21. The hypertension drug therapy start display screen 370 includes boxes 372 through 384 which provide recommendation for hypertension therapy treatment to the healthcare provider. The healthcare provider can also click on a hypertension drug therapy adjust term in box 380 to cause the workstation 110 to display a hypertension drug therapy adjustment screen (not shown) to adjust the hypertension therapy drugs and treatment.

Figure 22:
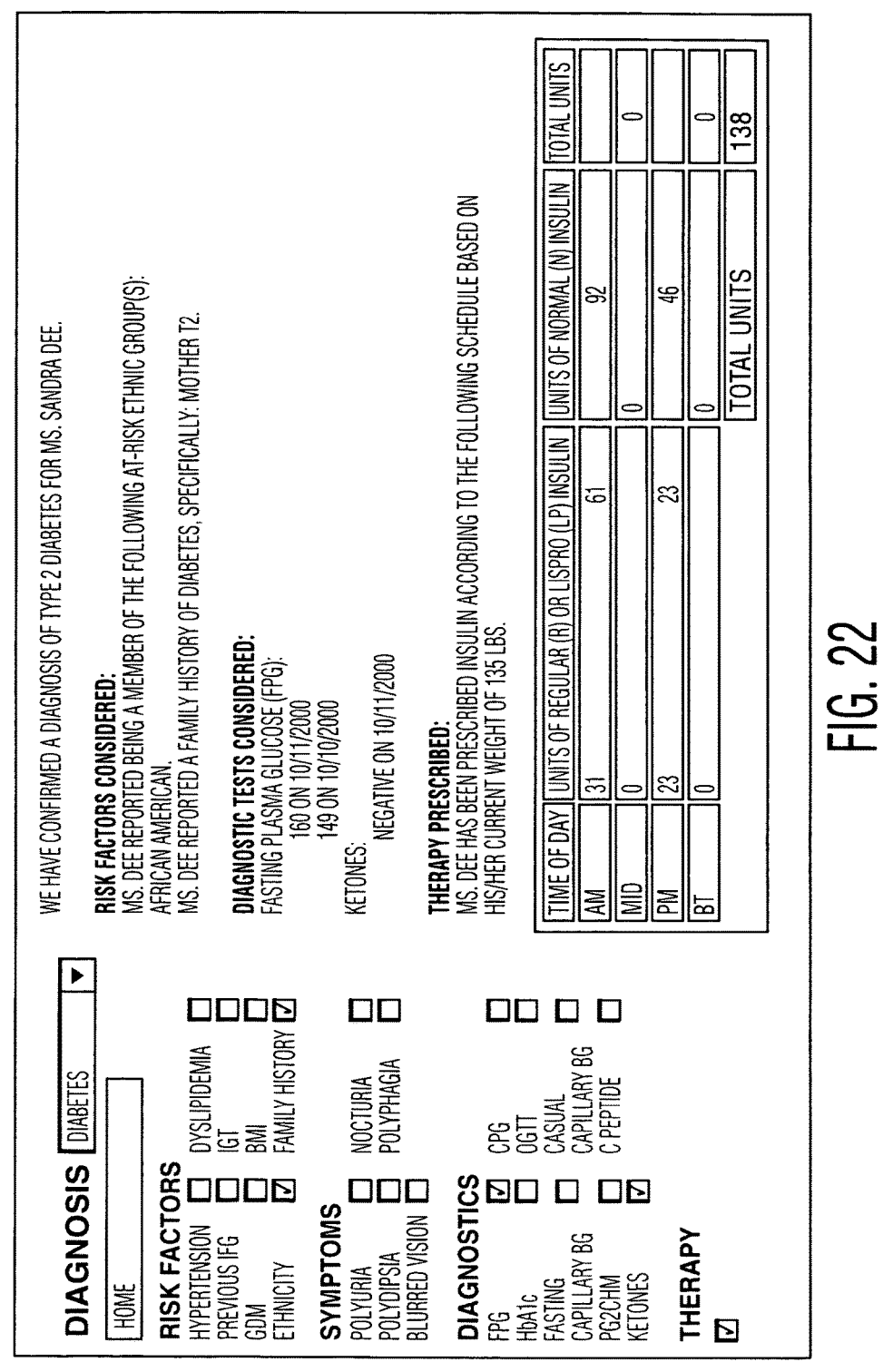
Figure 23B:
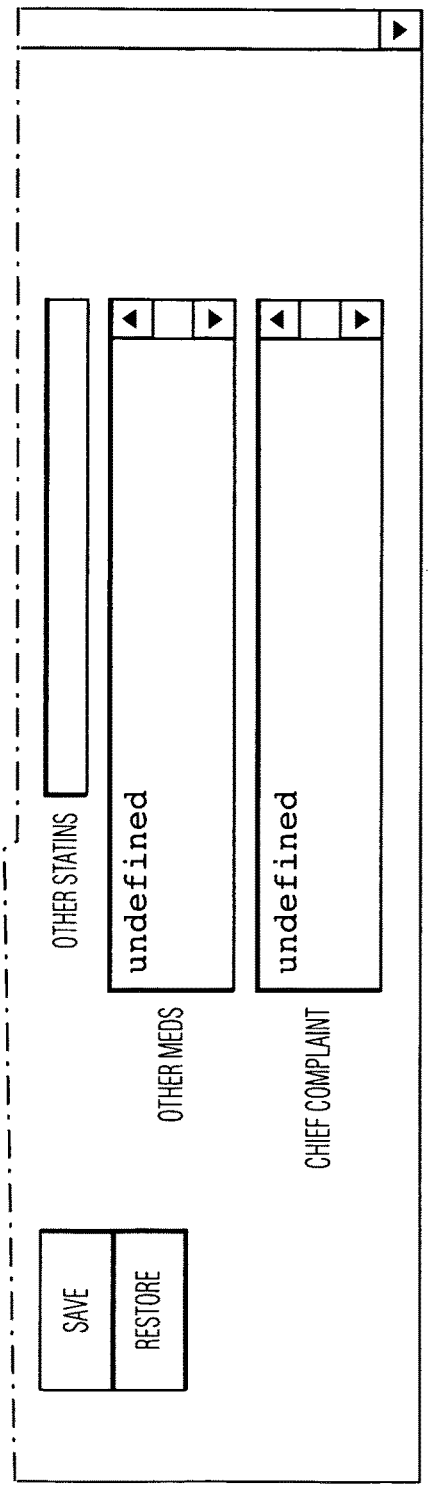
FIG. 23 is an example of a patient intake display that can be displayed on a display screen of a workstation employed in the network shown in FIG. 1 in accordance with an embodiment of the present invention.

Returning to FIG. 6, the button column 133 also enables the healthcare provider to display a diagnosis screen as shown in FIG. 22, a patient basic intake screen is drawn in FIG. 23, and a print screen as shown in FIG. 24.

Figure 26:
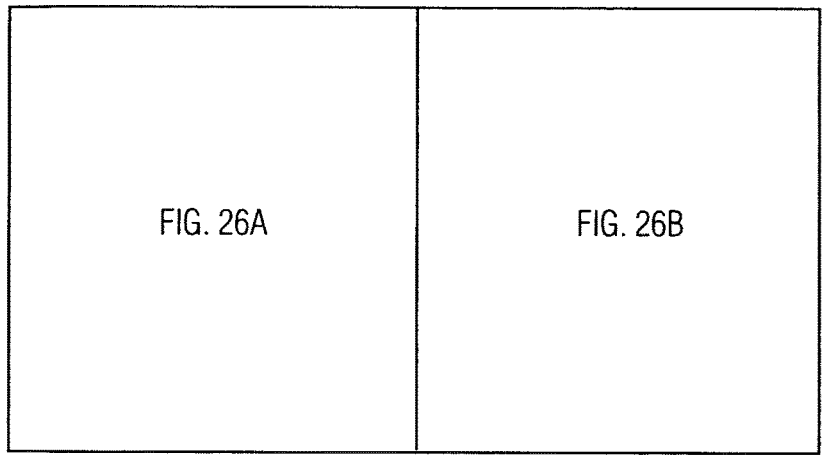
FIG. 26 is another example of a display containing a Type 2 diabetes stage 2 adjust pathway that can be generated on a display screen of a workstation employing the network shown in FIG. 1 in accordance with another embodiment of the present invention.
Figure 26A:
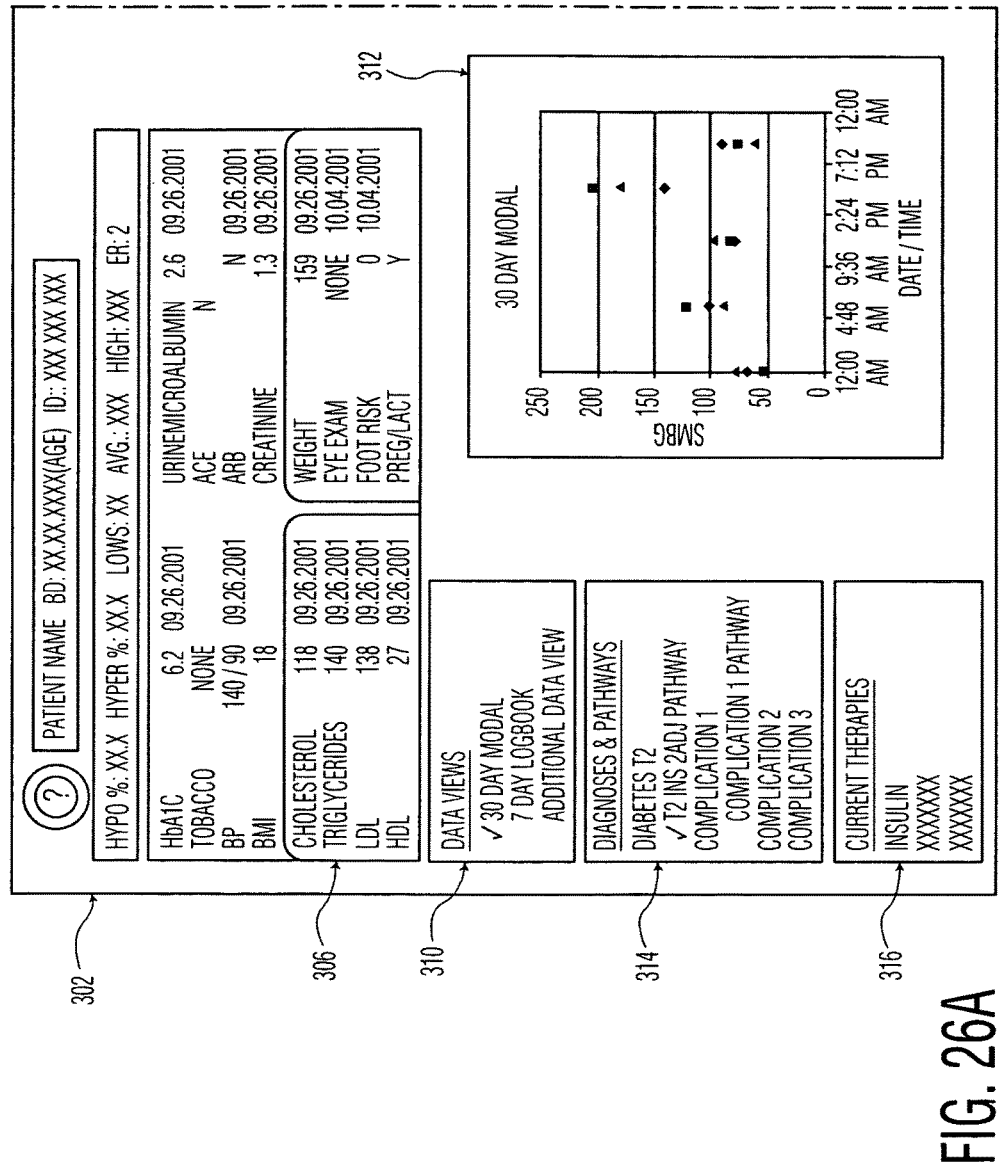
Figure 26B:
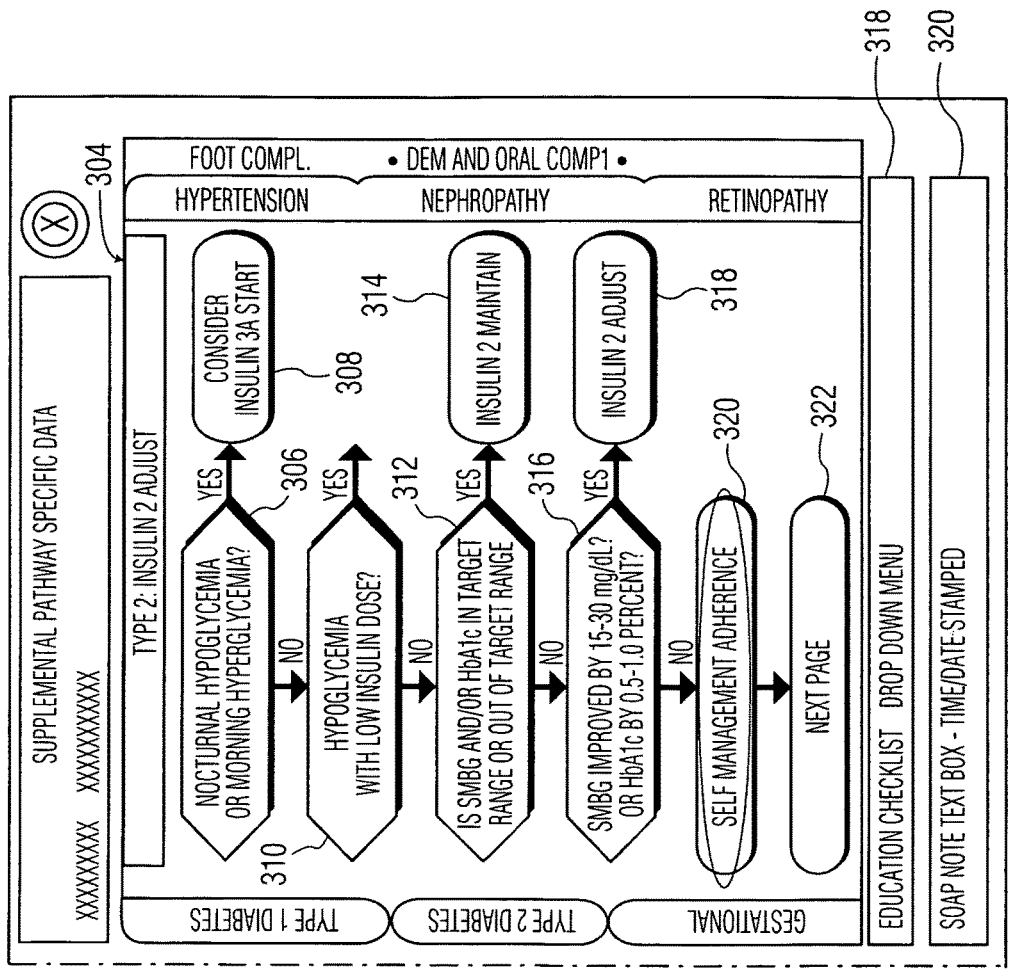

FIGS. 25 and 26 illustrate variations in the manner in which the system and method according to another embodiment of the present invention can control the workstation 110 to display display screens having different arrangements of the information and pathways discussed above. For example, when the healthcare provider accesses the database 104 via, for example, a healthcare provider workstation 106, the computer 102 can access the database 104 and provide a data to the workstation 106 that enables the workstation 106 to generate a display 400 on its display screen as shown in FIG. 25.

Similar to the display 130 shown in FIG. 5, the display 400 includes a listing of patient names. However, unlike display 130, display 400 lists the names chronologically by order of appointment time. In addition, display provides certain patient information associated with the patient's name. For example, the patient's HbA1c, blood pressure and LDL readings are displayed) if known), along with an indication as to whether the patient is a smoker. The display 400 can be configured to include any other patient-related information as deemed appropriate.

As with screen 130, if the healthcare provider is interested in using the system and method to obtain a diagnosis and treatment for a particular patient, the healthcare provider can use, for example, the mouse at his or her workstation 106 to click on the name of interest. This action causes the web browser to generate a display 402 illustrating a screening and diagnosis pathway for the patient, as shown in FIG. 26. In this example, display 402 shows a "Type 2 Insulin Adjust" pathway for illustrative purposes. However, it should be understood that the system and method can be configured so that the web browser initially displays, for example, a screening and diagnosis display screen, or any other suitable type of display and pathway.

As indicated, display 402 includes a pathway section 404 which, like the other pathways described above, includes a pathway comprising a plurality of boxes 406 through 422 setting forth guidelines that assist a health care provider is treating the patient. Also, like the other pathways described above, pathway section 404 highlights the patient's conditions based on the patient data. In other words, pathway section 404 also integrates the patient data with the guidelines. For example, because the patient has nocturnal hypoglycemia, the term "nocturnal hypoglycemia" is conscripted by a highlighted rectangle in box 406 as a consequence of the SMBG data presented on the left side of the screen. Likewise, because the patient's SMBG and/or HbA1c is within the target range, the term "in target range" is conscripted by a highlighted rectangle in box 412. The health care provider can therefore use this information in the guidelines in conjunction with the actual values, to determine a course of treatment for the patient in a manner similar to that discussed above.

In addition, display 402 includes a patient data section 408 that displays patient data such as the patient's HbA1c reading, blood pressure (BP) reading, and so on. Display 402 also includes a data views section 410 that provides an indication of the type of data view that is currently being displayed in the data view section 412. In this example, the data view being displayed is a 30 day Modal of SMBG, as indicted. The healthcare provider can click on one of the other options, such as the "7 day logbook", in the data views section 410 to display the 7 day logbook relating to the patient in the data view section 412. The Diagnosis & Pathways section 414 indicates the type of pathway that is being displayed in the pathway section 404. In this case, the Type 2 Insulin Adjust pathway is being displayed, as indicated. The healthcare provider can select a different pathway for display, such as the "Complication 1" pathway, and so on, by clicking on the appropriate term in the Diagnosis & Pathways section 414. The Current Therapies section 416 indicates the type of therapy (e.g., insulin) that the patient is undergoing.

As further shown in FIG. 26, the display 402 includes buttons including the terms "Type 1 Diabetes", "Gestational", and so on, which extend vertically on opposite sides of the pathway section 404. As with the buttons in button column 133 as discussed above, the healthcare provider can click on any of these buttons to display a pathway pertaining to the term indicated on the button being selected. For example, if the healthcare provider clicks on the "Type 1 Diabetes" button, the display 402 will display a pathway showing guidelines for treating Type 1 diabetes. In this event, the terms displayed in the Diagnosis & Pathways section 414 will also change to reflect the pathway being displayed in the pathway section 404. Additionally, the data variables being presented on the left screen half may also change to those relevant specifically to the new flow chart Pathway being accessed.

As further indicated in FIG. 26, display 402 includes an Education Checklist section 418 that can include a list of education that any patient should have for any pathway. For example, for the Type 2 Insulin Adjust pathway being displayed in pathway section 404, the healthcare provider can click on the Education Checklist section 418 to display a dropdown menu indicating recommended patient education, such as self-monitoring education, for that particular pathway. The display 402 also includes a subjective-objective assessment and plan (SOAP) section in which can be displayed notes that are entered by the healthcare provider, along with patient data, and so on.

As stated above the above system and method deem not be limited to the treatment of diabetes, but rather can be applied to any medical treatment as can be appreciated by one skilled in the art.

Although only a few exemplary embodiments of this invention have been described in detail above, those skilled in the art will readily appreciate that many modifications are possible in the exemplary embodiments of that material and departing from the novel teachings and advantages of this invention. Accordingly, all such modifications are intended to be included within the scope of this invention as defined in the following claims.

What is claimed is:

1. A method for integrating guidelines with data in a medical condition management system, comprising:
   storing general guideline data in a database representing at least one of guidelines for assessing a condition of a patient and guidelines for taking action on said patient;
   obtaining patient specific data with a medical instrument configured to measure any one of blood pressure, pulse rate, cholesterol level, and HbA1c level;
   automatically inputting said patient specific data from said medical instrument into a patient terminal;
   storing patient specific data received from the patient terminal in said database representing at least one physical aspect of said patient measured by said medical instrument;
   outputting at least one branching graphical pathway diagram on a display of said medical condition management system representing said guideline data, said branching graphical pathway diagram comprising a plurality of diagnosis boxes comprising data elements corresponding to data ranges, the diagnosis boxes connected by decision pathways corresponding to the data ranges, one such data range being highlighted to reflect measured patient data being within the data range,
   automatically determining at least one decision for at least one decision pathway based on the stored patient specific data, and
   automatically enhancing the diagnosis boxes of said branching graphical pathway diagram on said display to represent said general guideline data enhanced with said patient specific data integrated into the determined decision pathway to represent a relationship of at least a portion of said patient specific data to at least a portion of said general guideline data.

2. A method as claimed in claim 1, wherein:
   said outputting includes displaying said graphical pathway diagram on said display.

3. A method as claimed in claim 1, wherein:
   said patient data represents at least one physical condition of said patient, and said guideline data represents medical information.

4. A method as claimed in claim 3, wherein:
   said physical condition includes a form of diabetes, and said medical information pertains to diabetes.

5. A method as claimed in claim 1, further comprising:
   generating an output which is separate from said graphical pathway diagram and includes information determined from said relationship of at least a portion of said patient data to at least a portion of said guideline data.

6. A method as claimed in claim 5, wherein:
   said output includes one of a display and a printable document.

7. A method as claimed in claim 1, wherein:
   said outputting includes selectably generating a plurality of said graphical pathway diagrams, each of which representing different said guideline data.

8. A method as claimed in claim 1, wherein:
   said outputting includes highlighting at least a portion of said graphical pathway diagram based on said patient data.

9. A method as claimed in claim 1, wherein: said graphical pathway diagram includes at least one component which causes an output device to output information pertaining to said at least one component of said graphical pathway diagram.

10. A method as claimed in claim 1, further comprising:
    inputting one of said guideline data and said patient data for storage by said storing.

11. A system for integrating guidelines with data, comprising:
    a medical instrument configured to obtain patient specific data from a patient, the data comprising any one of blood pressure, pulse rate, cholesterol level, and HbA1c level, and to transmit the patient specific data to a patient terminal;
    a database configured to store general guideline data representing at least one of guidelines for assessing a condition of a patient and guidelines for taking action on said patient, and to store patient specific data received automatically from the patient terminal representing at least one physical aspect of said patient measured by said medical instrument; and
    an output display configured to automatically output at least one branching graphical pathway diagram representing said guideline data, said branching graphical pathway diagram comprising a plurality of diagnosis boxes comprising data elements corresponding to data ranges, the diagnosis boxes connected by decision pathways corresponding to the data ranges, one such data range being highlighted to reflect measured patient data being within the data range, the diagnosis boxes of said branching graphical pathway diagram representing said general guideline data enhanced with said patient specific data integrated into the decision pathway to represent at least one decision for at least one decision pathway based on the stored patient specific data as it relates to at least a portion of said general guideline data.

12. A system as claimed in claim 11, wherein: said output display includes a display, configured to display said graphical pathway diagram.

13. A system as claimed in claim 11, wherein:
said patient data represents at least one physical condition of said patient, and said guideline data represents medical information.

14. A system as claimed in claim 13, wherein:
said physical condition includes a form of diabetes, and said medical information pertains to diabetes.

15. A system as claimed in claim 11, wherein: said output display is further configured to generate an output which is separate from said graphical pathway diagram and includes information determined from said relationship of at least a portion of said patient data to at least a portion of said guideline data.

16. A system as claimed in claim 15, wherein:
said output includes one of a display and a printable document.

17. A system as claimed in claim 11, wherein: said output display is further configured to selectably generate a plurality of said graphical pathway diagrams, each of which representing different said guideline data.

18. A system as claimed in claim 11, wherein: said output display is further configured to highlight at least a portion of said graphical pathway diagram based on said patient data.

19. A system as claimed in claim 11, wherein: said graphical pathway diagram includes at least one component which causes said output display to output information pertaining to said at least one component of said graphical pathway diagram.

20. A system as claimed in claim 11, further comprising:
at least one database input, adapted to input one of said guideline data and said patient data into said database.

21. A non-transitory computer-readable medium storing instructions that when executed by a computer, cause the computer to perform operations comprising:
store general guideline data representing at least one of guidelines for assessing a condition of a patient and guidelines for taking action on said patient;
obtain patient specific data from a medical instrument configured to measure any one of blood pressure, pulse rate, cholesterol level, and HbA1c level, and to automatically store said patient specific data representing at least one physical aspect of said patient measured by said medical instrument;
automatically output at least one branching graphical pathway diagram representing said guideline data, said branching graphical pathway diagram comprising a plurality of diagnosis boxes comprising data elements corresponding to data ranges, the diagnosis boxes connected by decision pathways corresponding to the data ranges, one such data range being highlighted to reflect measured patient data being within the data range, and automatically determine at least one decision for at least one decision pathway based on the stored patient specific data, and to enhance the diagnosis boxes of said branching graphical pathway diagram to represent said general guideline data enhanced with said patient specific data integrated into the determined decision pathway to represent a relationship of at least a portion of said patient specific data to at least a portion of said general guideline data.

22. A non-transitory computer-readable medium as claimed in claim 21, wherein the instructions further cause the computer to output said graphical pathway diagram by displaying said graphical pathway diagram on a display.

23. A non-transitory computer-readable medium as claimed in claim 21, wherein: said patient data represents at least one physical condition of said patient, and said guideline data represents medical information.

24. A non-transitory computer-readable medium as claimed in claim 23, wherein: said physical condition includes a form of diabetes, and said medical information pertains to diabetes.

25. A non-transitory computer-readable medium as claimed in claim 21, further comprising: instructions that cause the computer to generate an output which is separate from said graphical pathway diagram and includes information determined from said relationship of at least a portion of said patient data to at least a portion of said guideline data.

26. A non-transitory computer-readable medium as claimed in claim 25, wherein: said output includes one of a display and a printable document.

27. A non-transitory computer-readable medium as claimed in claim 21, wherein: the instructions further cause the computer to selectably generate a plurality of said graphical pathway diagrams, each of which representing different said guideline data.

28. A non-transitory computer-readable medium as claimed in claim 21, wherein: the instructions further cause the computer to highlight at least a portion of said graphical pathway diagram based on said patient data.

29. A non-transitory computer-readable medium as claimed in claim 21, wherein: said graphical pathway diagram includes at least one component which causes an output device to output information pertaining to said at least one component of said graphical pathway diagram.

30. A non-transitory computer-readable medium as claimed in claim 21, further comprising: instructions that cause the computer to input one of said guideline data and said patient data for storage.

31. The method of claim 1, wherein said patient specific data comprises a blood glucose value measured in said patient.

32. The method of claim 1, wherein said medical instrument is selected from the group consisting of a sphygmomanometer and a blood glucose measuring device.

33. The system of claim 11, wherein said medical instrument is selected from the group consisting of a sphygmomanometer and a blood glucose measuring device.

34. The non-transitory computer-readable medium as claimed in claim 21, wherein said medical instrument is selected from the group consisting of a sphygmomanometer and a blood glucose measuring device.

* * * * *